United States Patent [19]

Kojima et al.

[11] Patent Number: 4,981,872
[45] Date of Patent: Jan. 1, 1991

[54] PROSTAGLANDIN DERIVATIVES, THEIR PREPARATION AND THEIR THERAPEUTIC USE

[75] Inventors: Koichi Kojima; Shigeo Amemiya; Kazuo Koyama; Keiichi Tabata; Nobuyoshi Iwata, all of Tokyo, Japan

[73] Assignee: Sankyo Company Limited, Tokyo, Japan

[21] Appl. No.: 144,878

[22] Filed: Jan. 15, 1988

[30] Foreign Application Priority Data

Jan. 19, 1987 [JP] Japan .................................. 62-9406

[51] Int. Cl.$^5$ .................. C07C 177/00; A61K 31/557
[52] U.S. Cl. ..................................... 514/530; 514/381; 514/570; 514/573; 514/621; 514/613; 514/684; 514/690; 548/253; 560/53; 560/121; 562/463; 562/503; 564/109; 564/189; 568/330; 568/379
[58] Field of Search .................. 560/121, 53; 562/503, 562/463; 548/253; 564/169, 189; 508/330, 379; 514/381, 530, 570, 573, 613, 621, 684, 64

[56] References Cited

U.S. PATENT DOCUMENTS 4,202,822  5/1980  Wissner .............................. 360/121

FOREIGN PATENT DOCUMENTS 170354  7/1988  Japan .................................. 560/121

OTHER PUBLICATIONS

IMI, Tet Letters, 28,3127 (1987).

*Primary Examiner*—Robert Gerstl
*Attorney, Agent, or Firm*—Frishauf, Holtz, Goodman & Woodward

[57] ABSTRACT

Prostaglandin derivatives having an oxo group at specified positions in the α side chain have a variety of physiological effects, notably a strong anti-ulcer activity accompanied by a limited ability to inhibit blood platelet aggregation.

47 Claims, No Drawings

PROSTAGLANDIN DERIVATIVES, THEIR PREPARATION AND THEIR THERAPEUTIC USE

BACKGROUND TO THE INVENTION

The present invention relates to a series of new prostaglandin derivatives, which have a variety of valuable therapeutic activities, and provides processes for preparing these compounds and methods and compositions using them.

The prostaglandins generally are known to have a variety of valuable physiological activities and a variety of prostaglandin derivatives and analogs thereof have been used or proposed to be used for the treatment of many diseases and disorders, including, for example, ulcers and thrombosis or related conditions, as a result of their valuable anti-ulcer activity or their ability to inhibit the aggregation of blood platelets.

However, the very fact of their multiplicity of potentially valuable activities itself leads to problems, as it is often desired to utilise one of these activities without another, and, indeed the possession by a compound of several activities may lead to complications if a particular activity, which in some circumstances, might be useful, in other circumstances, is merely an unwanted or even dangerous side effect.

Certain prostaglandin derivatives having, like the compounds of the present invention, a carbonyl group in the α-side chain are known and are known to have pharacological activities. For example, Japanese Patent Application Kokai No. 83524/77 describes the following 7-oxo derivatives, which have been found to have potentially useful anti-ulcer activity, and which are shown in formula (A):

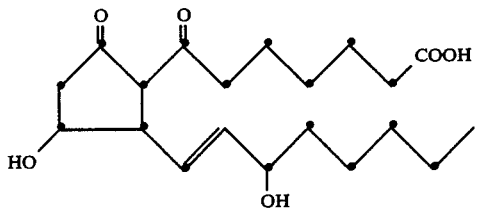

Other prostaglandin compounds having an oxo group at the 6-position are disclosed in U.S. Pat. No. 4,443,478 and are shown in formula (B):

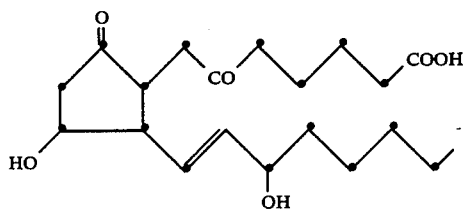

Unfortunately, these compounds have both an anti-ulcer activity and an inhibitory effect against platelet aggregation, without sufficient separation between the two activities.

It is, therefore, an object of the present invention to provide a series of novel prostaglandin derivatives.

It is a further object of the present invention to provide a series of novel prostaglandin derivatives which have valuable anti-ulcer activity.

It is a further object of the present invention to provide a series of novel prostaglandin derivatives which have valuable anti-ulcer activity accompanied by a low or very low inhibitory activity against platelet aggregation.

It is a further object of the invention to provide processes for preparing the compounds of the present invention as well as methods and compositions using them.

BRIEF SUMMARY OF INVENTION

The compounds of the invention are those compounds of formula (I):

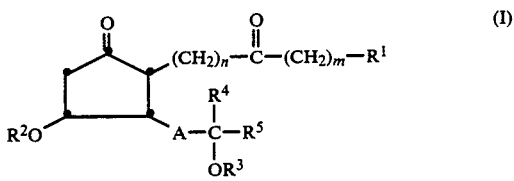

in which:

$R^1$ represents a carboxy group, a protected carboxy group, a tetrazolyl group, a carbamoyl group, a substituted carbamoyl group having one or two substituents selected from the group consisting of substituents (a), a hydroxymethylcarbonyl group, a protected hydroxymethylcarbonyl group, a hydroxymethyl group or a protected hydroxymethyl group;

$R^2$ and $R^3$ are independently selected from the group consisting of hydrogen atoms and hydroxy-protecting groups;

$R^4$ represents a hydrogen atom or a $C_1$-$C_4$ alkyl group;

$R^5$ represents a $C_1$-$C_{12}$ alkyl group, a substituted $C_1$-$C_{12}$ alkyl group having at least one substituent selected from the group consisting of substituents (b) a $C_2$-$C_{12}$ aliphatic hydrocarbon group having at least one ethylenic double bond, a substituted $C_2$-$C_{12}$ aliphatic hydrocarbon group having at least one ethylenic double bond and having at least one substituent selected from the group consisting of substituents (b), a $C_2$-$C_{12}$ alkynyl group, a substituted $C_2$-$C_{12}$ alkynyl group having at least one substituent selected from the group consisting of substituents (b) or a group of formula -B-$R^6$, in which:

B represents a single bond, a $C_1$-$C_6$ alkylene group, a $C_1$-$C_6$ alkylene group in which the carbon chain is interrupted by at least one hetero-atom selected from the group consisting of oxygen atoms and sulfur atoms, or a $C_2$-$C_6$ alkylene group in which at least one of the carbon-carbon single bonds is replaced by a carbon-carbon double bond; and $R^6$ represents a $C_3$-$C_{10}$ cycloalkyl group, a substituted $C_3$-$C_{10}$ cycloalkyl group having at least one substituent selected from the group consisting of $C_1$-$C_6$ alkyl groups, an aryl group, a heterocyclic group having from 5 to 10 ring atoms of which from 1 to 5 are hetero-atoms selected from the group consisting of nitrogen, oxygen and sulfur atoms and being unsubstituted or having at least one substituent selected from the group consisting of substituents (c) and substituents (d);

A represents a group of formula —CH —, —CH=-CH—, —C≡C—, —O—CH$_2$—or —S—CH$_2$—;

m is 0 or an integer from 1 to 5; and n is an integer from 2 to 5;

substituents (a)

$C_1$–$C_4$ alkyl groups, substituted $C_1$–$C_4$ alkyl groups having at least one substituent selected from the group consisting of substituents ($a^1$), aliphatic carboxylic acyl groups, aromatic carboxylic acyl groups. $C_1$–$C_6$ alkanesulfonyl groups, arylsulfonyl groups, phenyl groups and phenyl groups having at least one $C_1$–$C_6$ alkyl substituent;

substituents ($a^1$)

hydroxy groups, carboxy groups, $C_2$–$C_7$ alkoxycarbonyl groups and phenyl groups;

substituents (b)

halogen atoms, $C_1$–$C_4$ alkoxy groups, aliphatic carboxylic acyl groups, aromatic carboxylic acyl groups and groups of formula —$OR^7$ where $R^7$ represents a hydrogen atom, a $C_1$–$C_6$ aliphatic carboxylic acyl group, an aromatic carboxylic acyl group, an aralkyl group, a heterocyclic group having 5 or 6 ring atoms of which 1 or 2 are hetero-atoms selected from the group consisting of oxygen and sulfur atoms, an alkoxyalkyl group in which the alkoxy and alkyl parts are both $C_1$–$C_4$, an alkylthioalkyl group in which each alkyl part is $C_1$–$C_4$, an aralkyloxymethyl group or a tri-substituted silyl group;

said aryl groups and the aromatic parts of said aromatic carboxylic acyl, arylsulfonyl, aralkyl and aralkyloxymethyl groups being $C_6$–$C_{12}$ carbocyclic aryl groups which are unsubstituted or have at least one substituent selected from the group consisting of substituents (c);

substituents (c):

hydroxy groups, $C_1$–$C_6$ alkyl groups, $C_1$–$C_4$ alkoxy groups, $C_1$–$C_4$ alkylthio groups. $C_2$–$C_7$ aliphatic carboxylic acyl groups, $C_2$–$C_7$ aliphatic carboxylic acyloxy groups, aryl groups provided that the aryl substituent is not itself substituted by an aryl group, aromatic carboxylic acyl groups. aromatic carboxylic acyloxy groups, $C_2$–$C_7$ aliphatic carboxylic acylamino groups, aromatic carboxylic acylamino groups, heterocyclic-carbonyl groups, provided that any such heterocyclic-carbonyl substituent is not itself substituted by a heterocyclic or heterocyclic-carbonyl group. arylalkenoyl groups in which the alkenoyl part is $C_3$–$C_7$, trifluoromethyl groups, halogen atoms, nitro groups, cyano groups, amino groups, $C_1$–$C_4$ alkylamino groups, dialkylamino groups in which each alkyl part is $C_1$–$C_4$, carbamoyl groups, alkylcarbamoyl groups in which the alkyl part is $C_1$–$C_4$, dialkylcarbamoyl groups in which each alkyl part is $C_1$–$C_6$, alkoxycarbonyloxy groups in which the alkoxy part is $C_1$–$C_4$, heterocyclic groups, provided that any such heterocyclic substituent is not itself substituted by a heterocyclic or heterocyclic-carbonyl group, carboxy groups and esters and amides of said carboxy groups, said aryl groups and the aromatic parts of said aromatic acyl, acyloxy and acylamino groups being $C_6$–$C_{10}$ carbocyclic aryl groups which are unsubstituted or have at least one substituent selected from the group consisting of $C_1$–$C_4$ alkyl groups, $C_1$–$C_4$ alkoxy groups, hydroxy groups and halogen atoms;

substituents (d):

aryl groups, as defined above, and oxygen atoms; and pharmaceutically acceptable salts and esters thereof.

The invention further provides a pharmaceutical composition comprising at least one compound of formula (I) or a pharmaceutically acceptable salt or ester thereof in admixture with a pharmaceutically acceptable carrier or diluent.

The invention still further provides a method of treating a mammal, which may be human or non-human, to relieve an ulcerative condition by administering thereto an effective amount of at least one compound of formula (I) or a pharmaceutically acceptable salt or ester thereof.

The invention also provides processes for preparing the compounds of the invention, as described in more detail hereafter.

Detailed Description of Invention

In the compounds of the present invention, where $R^1$ represents a protected carboxy group, it is preferably selected from the group consisting of: $C_2$–$C_{11}$ alkoxycarbonyl groups, such as the methoxycarbonyl, ethoxycarbonyl, propoxycarbonyl, isopropoxycarbonyl, butoxycarbonyl, t-butoxycarbonyl, pentyloxycarbonyl, hexyloxycarbonyl, heptyloxycarbonyl, octyloxycarbonyl, nonyloxycarbonyl and decyloxycarbonyl groups; $C_4$–$C_8$ cycloalkyloxycarbonyl groups which are unsubstituted or have at least one substituent selected from the group consisting of $C_1$–$C_6$ alkyl groups, such as the cyclopropyloxycarbonyl, 1-pentylcyclopropyloxycarbonyl, cyclobutyloxycarbonyl, cyclopentyloxycarbonyl 3-ethylcyclopentyloxycarbonyl cyclohexyloxycarbonyl, 4-methylcyclohexyloxycarbonyl and cycloheptyloxycarbonyl groups; aralkyloxycarbonyl groups, such as the benzyloxycarbonyl, p-bromobenzyloxycarbonyl and benzhydryloxycarbonyl groups; aryloxycarbonyl groups, such as the phenoxycarbonyl and naphthyloxycarbonyl groups [the aryl part of said group may be unsubstituted or it may be substituted by one or more of the substituents defined generally above as substituents (c), preferably: a $C_1$–$C_6$ alkyl group, for example a methyl, ethyl, propyl, isopropyl, butyl or t butyl group; a $C_2$–$C_5$ aliphatic acylamino group, such as an acetamido or propionamido group; a benzoylamino group which may be unsubstituted or substituted with a $C_1$–$C_4$ alkyl. $C_1$–$C_4$ alkoxy or hydroxy group, such as a benzoylamino p-methylbenzoylamino m-methoxybenzoylamino, p-methoxybenzoylamino or p-hydroxybenzoylamino group; a carbamoyl group; or a carbamoyl group having one or two substituents selected from the group consisting of $C_1$–$C_4$ alkyl groups, phenyl groups and methanesulfonyl groups]; an alkoxycarbonyl group having at least one substituent selected from the group consisting of substituents (b). defined above, preferably an aromatic carboxylic acyl group, such as a phenacyloxycarbonyl group; or a terpenyloxycarbonyl group, preferably an acyclic terpenyloxycarbonyl group, such as a geranyloxycarbonyl group. The most preferred groups which may be represented by $R^1$ include the $C_2$–$C_{11}$ alkoxycarbonyl groups, substituted and unsubstituted phenoxycarbonyl groups and naphthyloxycarbonyl groups.

Where $R^1$ represents a tetrazolyl group, this is preferably a 1H-tetrazol-5-yl group.

Where $R^1$ represents a carbamoyl group, this may be unsubstituted or may have one or two substituents selected from the group consisting of substituents (a) defined above. Where the substituents are $C_1$–$C_4$ alkyl groups, these may be straight or branched chain groups and examples include the methyl, ethyl, propyl, isopropyl and butyl groups. Where the substituents are substituted alkyl groups, these may be at least one substituent selected from the group consisting of substituents ($a^1$). Where the substituents are aliphatic carboxylic acyl groups, these are preferably groups having from 1 to 6, more preferably from 2 to 4, carbon atoms and are more preferably alkanoyl groups, which may be unsubstituted or have at least one substituent selected from the group consisting of substituents (b). preferably halogen atoms. Examples of such aliphatic carboxylic acyl groups include the acetyl and trifluoroacetyl groups. Where the substituent is an aromatic carboxylic acyl group, this is preferably an arylcarbonyl group in which the aryl part is as defined above and is most preferably a benzoyl group. Where the substituent is a $C_1-C_4$ alkanesulfonyl group, this is preferably a methanesulfonyl or ethanesulfonyl group. Where the substituent is an arylsulfonyl group, the aryl part is preferably as defined above and examples include the benzenesulfonyl and p-toluenesulfonyl groups. Where the substituent is a phenyl group, this may be unsubstituted or may have at least one $C_1-C_4$ alkyl substituent and examples include the phenyl and tolyl groups. Of the carbamoyl groups, We prefer the carbamoyl, mono($C_1-C_4$ alkyl)carbamoyl, mono(substituted $C_1-C_4$ alkyl)carbamoyl, phenylcarbamoyl and methanesulfonylcarbamoyl groups, more preferably the mono($C_1-C_4$ ₁ alkyl)carbamoyl, mono(substituted $C_1-C_4$ alkyl)carbamoyl and methanesulfonylcarbamoyl groups.

Where $R^1$ represents a protected hydroxymethylcarbonyl group or a protected hydroxymethyl group, any protecting group commonly used for protecting hydroxy groups in compounds of this type may equally be employed here. Examples of preferred protecting groups include: the $C_2-C_5$ aliphatic acyl groups, such as the acetyl, propionyl, butyryl, isobutyryl and valeryl groups; the aromatic acyl groups, such as the benzoyl and naphthoyl groups; the aralkyl groups, such as the benzyl, p-nitrobenzyl and p-methoxybenzyl groups; 5 or 6 membered heterocyclic groups containing an oxygen or sulfur atom in the ring and which are unsubstituted or have at least one substituent selected from the group consisting of substituents (c) and (d), defined above, preferably an alkoxy group, such as the 2-tetrahydropyranyl, 2-tetrahydrofuranyl, 4-methoxytetrahydropyran4-yl and 2-tetrahydrothiopyranyl groups; a methyl group having at least one substituent selected from the group consisting of alkoxy groups, alkylthio groups and aralkyloxy groups, such as the methoxymethyl, methylthiomethyl, ethoxymethyl and benzyloxymethyl groups; the 1-alkoxyethyl groups, such as the 1-methoxyethyl and 1-ethoxyethyl groups; the tri-($C_1-C_4$ alkyl)- or diaryl($C_1-C_4$ alkyl)silyl groups, such as the trimethylsilyl, triethylsilyl, tripropylsilyl, t-butyldimethylsilyl and diphenyl-t-butylsilyl groups; add the trityl group. preferred protecting groups, however, for the protection of the hydroxymethylcarbonyl and hydroxymethyl groups represented by $R^1$ are the silyl groups.

$R^1$ and $R^3$ are the same or different and each represents a hydrogen atom or a hydroxy-protecting group. Where one or both represents a hydroxyprotecting group, this may be selected from those hydroxyprotecting groups listed above for use in protecting the hydroxymethylcarbonyl or hydroxymethyl groups represented by $R^1$. However, in the case of the hydroxyprotecting groups represented by $R^2$ and $R^3$, the preferred protecting groups are the 2-tetrahydropyranyl and 2-tetrahydrofuranyl groups.

Most preferably, $R^2$ and $R^3$ are the same and each represents a hydrogen atom.

Where $R^4$ represents a $C_1-C_4$ alkyl group, this may be a straight or branched chain alkyl group and examples include the methyl, ethyl, propyl, isopropyl, butyl, isobutyl, sec-butyl and t-butyl groups, of which the methyl, ethyl, propyl, isopropyl and butyl groups are preferred, and the methyl group is the more preferred. However, it is most preferred that $R^4$ should represent a hydrogen atom.

Where $R^5$ represents an alkyl, ethylenically unsaturated aliphatic or alkynyl group, these may be unsubstituted or may have at least one substituent selected from the group consisting of substituents (b), that is: halogen atoms, for example the fluorine chlorine or bromine atoms; $C_1-C_4$ alkoxy groups, for example the methoxy, ethoxy, propoxy, isopropoxy or butoxy groups; groups of formula —$OR^7$, for example as exemplified below; and acyl groups for example as defined above in relation to the aliphatic and aromatic carboxylic acyl groups which may be substituents on carbamoyl groups, and preferably the acetyl, propionyl or benzoyl groups.

Examples of groups which may be represented by $R^7$ include: $C_2-C_5$ aliphatic carboxylic acyl groups, preferably alkanoyl groups, such as the acetyl, propionyl, butyryl, isobutyryl and valeryl groups; aromatic carboxylic acyl groups, preferably arylcarbonyl groups in which the aryl part is as defined above, preferably benzoyl or naphthoyl groups; aralkyl groups in which the aryl part is preferably as defined above and the alkyl part is preferably a $C_1-C_3$, more preferably $C_1$, alkyl group, for example the p-methoxybenzyl group; 5-or 6-membered heterocyclic groups containing oxygen or sulfur, which may be unsubstituted or have an alkoxy substituent, for example the 2-tetrahydropyranyl. 2-tetrahydrofuranyl, 4-methoxytetrahydropyran-4-yl or 2-tetrahydrothiopyranyl groups; $C_1-C_4$ alkyl groups (preferably methyl groups) having a $C_1-C_4$ alkoxy substituent, for example the methoxymethyl and ethoxymethyl groups: alkylthioalkyl, particularly alkylthiomethyl, groups where each alkyl part is $C_1-C_4$, such as the methylthiomethyl group; methyl groups having an aralkyloxy substituent, in which the aralkyl part is preferably as defined above, for example the benzyloxymethyl group; and trisubstituted silyl groups, in which the three substituents are the same or different and preferably selected from the group consisting of $C_1-C_4$ alkyl groups and aryl groups (the aryl groups preferably being as defined above), for example the trimethylsilyl, triethylsilyl, tripropylsilyl, t-butyldimethylsilyl and diphenyl-t-butylsilyl groups.

Of the substituents listed above for alkyl, ethylenically unsaturated aliphatic or alkynyl groups, the fluorine, chlorine and $C_1-C_4$ alkoxy substituents are preferred, the $C_1-C_4$ alkoxy substituents, especially the methoxy and ethoxy groups, being more preferred Where $R^5$ represents an alkyl group, this may be a straight or branched chain group and may be unsubstituted or have one or more substituents as defined above. Examples of such alkyl groups include the methyl, ethyl, propyl, isopropyl, butyl, isobutyl, t-butyl, pentyl, isopentyl, 1-methylpentyl, 2-methylpentyl, hexyl, heptyl, 1,1-dimethylpentyl, 1,1-dimethylhexyl, 1,1-dimethylheptyl, 1-methylhexyl 2-methylhexyl, 2-ethylpentyl, 2,6-dimethylheptyl 1,1,6-trimethylheptyl, octyl, 2-methyloctyl, nonyl, 2-methylnonyl, 2-ethyloctyl, decyl, undecyl, dodecyl, 2-methyldecyl and 2-ethyldecyl groups. Of these, the $C_1-C_{10}$ alkyl groups are preferred, especially the $C_1-C_{10}$ groups, for example the isopropyl, butyl, isobutyl, t-butyl, pentyl, isopentyl. 1-methylpentyl, 2-methylpentyl, hexyl, heptyl. 1,1-dimethylpentyl, 1.1-dimethylhexyl, 2-methylhexyl, 1,1-dimethylheptyl, 2,6-dimethylheptyl, 1,1,6-trimethylheptyl, octyl, 2-methyloctyl and 2-ethyloctyl groups, and the most preferred groups are the $C_5$–$C_{10}$ alkyl groups, such as the pentyl, 1-methylpentyl, hexyl, 1,1-dimethylpentyl, 1,1-dimethylhexyl, 1,1-dimethylheptyl, 1,1,6-trimethylheptyl and 2-methylhexyl groups.

Where $R^5$ represents an aliphatic hydrocarbon group having at least one ethylenically unsaturated double bond, this is preferably an alkenyl group or an alkadienyl group and may be unsubstituted or substituted as defined above Examples of preferred groups include the 1-butylvinyl, allyl, 2-propylallyl, 2-butenyl, 2-pentenyl, 4-pentenyl, 2-methyl-3-pentenyl, 4-methyl3-pentenyl, 1-methyl-4-pentyl 1,1-dimethylpentenyl, 4-hexenyl, 5-hexenyl, 1,4-dimethylpentenyl, 5-heptenyl, 1-methyl-5-hexenyl, 1,1-dimethyl-5-hexenyl, 6-methyl-5-heptenyl, 6-dimethyl-5-heptenyl. 1,6-dimethyl-5-heptenyl, 1,6-trimethyl-5-heptenyl. 6-methyl-5-octenyl 2.6-dimethyl-5-octenyl. 2,6-ethyl-5-octenyl 2-methyl-6-ethyl-5-octenyl, 2,6-diethyl-5-octenyl and 3,8-dimethyl-nona-3,7-dienyl groups. More preferred groups are the $C_3$–$C_{10}$ alkenyl groups, and the most preferred groups are the $C_5$–$C_{10}$ alkenyl groups such as the 1-butylvinyl 2-propylallyl, 2-pentenyl, 4-pentenyl. 2-methyl-3-pentenyl. 4-methyl-3-pentenyl, 1-methyl-4-pentenyl, 1.1-dimethyl-4-pentenyl, 4-hexenyl, 5-hexenyl, 1.4-dimethyl-3-pentenyl. 5-heptenyl, 1-methyl-5-hexenyl, 1,1-dimethyl-5-hexenyl, 6-methyl-5-heptenyl, 2,6-dimethyl-5-heptenyl, 1,6-dimethyl-5-heptenyl, 1,1,6-trimethyl-5-heptenyl and 3,8-dimethyl-nona-3,7-dienyl groups Where $R^5$ represents an alkynyl group, this is a $C_2$–$C_{12}$, preferably $C_3$–$C_{10}$, alkynyl group, which may be a straight or branched chain group and which may be unsubstituted or substituted as defined above. Examples such alkynyl groups include the propargyl, 2-butynyl 2-pentynyl, 3-pentynyl. 1-methyl-2-butynyl, 2-hexynyl, 1-methyl-2-pentynyl. 1-methyl-3-pentynyl, 1,1-dimethyl-2-pentynyl, 1,1-dimethyl-3-pentynyl, 1,1-dimethyl-2-hexynyl, 1-methyl-3-hexynyl, 1,1-dimethyl-5-hexynyl, and 1,1 dimethyl-3-octynyl groups. More preferred groups are the $C_5$–$C_{10}$ alkynyl groups, such as the 2-pentynyl, 3-pentynyl, 1-methyl-2-pentynyl, 1-methyl-3-hexynyl, 1-methyl-3-pentynyl, 1,1-dimethyl-2-pentynyl, 1,1-dimethyl-3-pentynyl. 1,1-dimethyl-5-hexynyl and 1,1-dimethyl-3-octynyl groups. The most preferred group is the 1-methyl-3-pentynyl group.

Where B represents a $C_1$–$C_6$ alkylene group, this may be a straight or branched chain group and may optionally contain at least one oxygen or sulfur atom in its carbon chain. Any single carbon atom of the alkylene or alkenylene group may be substituted by a $C_2$–$C_6$ alkylene group, so as to form, with that carbon atom of the alkylene or alkenylene chain a $C_3$–$C_7$ gem-cycloalkylene group. Examples of such alkylene and alkenylene groups include the methylene, ethylene, methylmethylene, trimethylene, dimethylmethylene, tetramethylene, 1-methyltrimethylene, 1.1-dimethylethylene, pentamethylene, 1,1-dimethyltrimethylene, hexamethylene, oxymethylene (—$CH_2$—O—), oxyethylidene [—$CH(CH_3)$—O—], thiomethylene (—$CH_2$—S—), methyleneoxymethylene (—$CH_2$—O—$CH_2$—), allylene (—$CH_2$—CH=CH—) and gem-cyclopropylene groups. Of these, we particularly prefer $C_1$–$C_4$ alkylene groups and such groups in which the carbon chain is interrupted by a single oxygen or sulfur atom, for example the methylene, ethylene, methylmethylene, trimethylene, dimethylmethylene, oxymethylene, oxyethylidene and thiomethylene groups, and more particularly we prefer the methylene, oxymethylene and oxyethylidene groups. Alternatively, we prefer that B should represent a single bond.

Where $R^6$ represents a $C_3$–$C_{10}$ cycloalkyl group, this may be unsubstituted or may contain at least one, and preferably only one. $C_1$–$C_6$, more preferably $C_1$–$C_4$, alkyl substituent. The cycloalkyl group may be monocyclic, bicyclic or higher polycyclic. Examples of such groups include the cyclopropyl, 1-pentylcyclopropyl, cyclobutyl, cyclopentyl, 3-ethylcyclopentyl, cyclohexyl, 3-propylcyclohexyl, 4-methylcyclohexyl, cycloheptyl, bicyclo[4.3.0]non-7-yl and adamantyl groups, of which the $C_5$–$C_{10}$ cycloalkyl groups are preferred, and the cyclopentyl and cyclohexyl groups are more preferred.

Where $R^6$ represents an aryl group, this is preferably as defined above in relation to aryl groups generally and is more preferably such a group having from 6 to 10 ring carbon atoms and is most preferably a phenyl group. Such aryl groups may be unsubstituted or may contain at least one, and preferably 1 or 2. substituents selected from the group consisting of substituents (c). defined above, more preferably hydroxy groups, $C_1$–$C_4$ alkyl groups, $C_1$–$C_4$ alkoxy groups, $C_1$–$C_4$ alkylthio groups, halogen atoms, aryl groups (provided that the aryl substituent is not itself substituted by an aryl group), trifluoromethyl groups, amino groups and $C_2$–$C_5$ aliphatic carboxylic acylamino groups. Examples of such aryl groups include the phenyl, p-hydroxyphenyl, o-tolyl, m-tolyl, p-tolyl, p-ethylphenyl, m-propylphenyl, p-propylphenyl, 2,5-dimethylphenyl, m-butylphenyl, o-methoxyphenyl, m-methoxyphenyl, p-methoxyphenyl, o-ethoxyphenyl, m-methylthiophenyl, p-methylthiophenyl, p-ethylthiophenyl, o-fluorophenyl, m-fluorophenyl, p-fluorophenyl, o-chlorophenyl, m-chlorophenyl, p-chlorophenyl, p-bromophenyl, p-trifluoromethylphenyl, 3.4-dimethylphenyl, 3-fluoro-4-methylphenyl, 2,4-ichlorophenyl, 3,4-dichlorophenyl, o-aminophenyl, m-aminophenyl, p-aminophenyl, p-acetamidophenyl m-acetamidophenyl, p-acetamidophenyl 1-naphthyl, 2-naphthyl and biphenyl groups, of which preferred substituted phenyl groups are those substituted by a halogen atom, a $C_1$–$C_4$ alkyl group, a $C_1$–$C_4$ alkoxy group or a trifluoromethyl group, and more preferred groups are those substituted with a methyl group, an ethyl group, a methoxy group, a fluorine atom, a chlorine atom or a trifluoromethyl group; however the unsubstituted phenyl group itself is most preferred.

Where $R^6$ represents a heterocyclic group, this may be an aromatic or non-aromatic group, containing from 5 to 10 ring atoms, of which at least one is a hetero-atom selected from the group consisting of oxygen, sulfur and nitrogen atoms, preferred non-aromatic heterocyclic groups have 5 or 6 of said hetero-atoms and examples include the tetrahydrofuryl, tetrahydropyranyl tetrahydrothienyl, pyrrolidinyl, piperidyl and morpholinyl (e.g. morpholino) groups, of which the more preferred groups are the 2-tetrahydrofuryl and 2-tetrahydropyranyl groups, preferred aromatic heterocyclic groups have 5, 6, 9 or 10 hetero-atoms, and examples include the furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl groups, of which the preferred groups are the 2-thienyl 3-thienyl. 1 imidazolyl and 3-indolyl groups.

A may represent a group of formula —$CH_2CH_2$—(i.e. an ethylene group), —CH=CH—(i.e. a vinylene group), —C≡C—(i.e. an ethynylene group), —O—CH$_2$—(i.e. an oxymethylene group) or —S—CH$_2$—(i.e. a thiomethylene group); however, it preferably represents a vinylene group, and more preferably represents a trans-vinylene group.

m is O or an integer from 1 to 5 and n is an integer from 2 to 5. The more preferred compounds are those in which m is an integer from 2 to 5 and n is the integer 2 or 3.

Of the compounds of the invention, the preferred compounds are those in which R$^5$ represents one of the pentyl, hexyl, 5-chloropentyl, 5-fluoropentyl, 5-methoxypentyl, 5-ethoxypentyl, 1-methylpentyl 1,1-dimethylpentyl, 2-methylpentyl 2 2-dimethylpentyl, 1,1-dimethylhexyl, 5-fluoro-1-methylpentyl, 5-fluoro-1,1-dimethylpentyl, 5-chloro-1,1-dimethylpentyl, 5-methoxy-1,1-dimethylpentyl, 5-ethoxy1,1-dimethylpentyl, 2-ethoxy-1,1-dimethylethyl, 3-ethoxy-1 1-dimethylpropyl 3-methoxy-1,1-dimethylpropyl, 2-methylhexyl, 4-pentenyl, 1-methyl-4-pentenyl, 1,1-dimethyl-4-pentenyl, 1,1-dimethyl-5-hexenyl, 1,1-dimethyl-6-heptenyl, 2-methyl-4-pentenyl, 2-methyl-5-hexenyl, 2,6-dimethyl-5-heptenyl, 4-methyl-3-pentenyl, 6-methyl-5-heptenyl, 1,6-dimethyl5-heptenyl, 1,1,6-trimethyl-5-heptenyl, 1,1,4-trimethyl-3-pentenyl, 1,1,5-trimethyl-4-hexenyl, 1,4-dimethyl 13-pentenyl, phenoxymethyl, phenyl cyclopentyl, cyclohexyl, 2-furyl, 2-thienyl, 3-indolyl p-fluorophenyl, m-fluorophenyl, p-chlorophenyl, p-methoxyphenyl, 3-indolylmethyl, 2-furylmethyl, cyclohexylmethyl, 2-cyclohexylethyl, p-chlorophenoxymethyl, m-chlorophenoxymethyl, p-chlorophenoxymethyl, p-fluorophenoxymethyl, m-fluorophenoxymethyl, m-fluorophenoxymethyl, p-methoxyphenoxymethyl, 3,5-dimethylphenoxymethyl, benzyloxymethyl, 2-phenylethoxymethyl, p-ethylphenoxymethyl, p-methylphenoxymethyl, p-acetamidophenoxymethyl, p-(methylamino)phenoxymethyl, cyclohexyloxymethyl, phenethyl, phenylthiomethyl, p-fluorophenylthiomethyl, m-fluorophenylthiomethyl, p-chlorophenylthiomethyl, 3,4-dichlorophenoxymethyl, 3,4-difluorophenoxymethyl, p-bromophenoxymethyl, m-bromophenoxymethyl, m-trifluoromethylphenoxymethyl, p-trifluoromethylphenoxymethyl, p-propylphenoxymethyl, p-propylphenoxymethyl, p-methylthiophenoxymethyl, 2-(p-chlorophenoxy) ethyl, 2-(m-chlorophenoxy)ethyl, 1-(p-ohlorophenoxy)ethyl, 1-(m-chlorophenoxy)ethyl, 2-(p-fluorophenoxy)ethyl, 1-phenoxyethyl, 1-cyclohexyloxyethyl, 1-(3-indolyl)ethyl, 1-(p-methoxyphenoxy)ethyl, 1-benzyloxyethyl, 1-(p-ethylphenoxy)ethyl, 1-phenylthioethyl, 1-(p-fluorophenylthio)ethyl, 1-methyl-1-phenoxyethyl, 1-methyl-1-(p-chlorophenoxy) ethyl, 5-fluoro-1-methylhexyl, 5-fluoro-1,1-dimethylhexyl, 5-chloro-1,1-dimethylhexyl, 5-methoxy-1,1dimethylhexyl, 5-ethoxy-1,1-dimethylhexyl, 5-fluoro,1-dimethylpentyl, 5-chloro-1,1-dimethylpentyl, 5-methoxy-1,1-dimethylpentyl, 5-ethoxy-1,1-dimethylpentyl, 1,1-dimethylhexyl, 2,6-dimethylheptyl, o-methoxyphenoxymethyl, 3-thienyloxymethyl and 2-phenoxyethyl groups.

Also, of the compounds of the invention, the preferred compounds are those in which R$^1$ represents one of the carboxy, methoxycarbonyl, p-benzamidophenoxycarbonyl, p-acetamidophenoxycarbonyl, p-(p-methoxybenzamido)phenoxycarbonyl, p-carbamoylphenoxycarbonyl, p-N,N-dimethylcarbamoylphenoxycarbonyl, p-(p-hydroxybenzamido)phenoxycarbonyl, carbamoyl, N-(carboxymethyl)carbamoyl, N-(1-carboxyethyl)carbamoyl, N-(1-carboxy2-phenylethyl)carbamoyl, N-(1-carboxy-3-methylbutyl)carbamoyl, N-(methoxycarbonylmethyl)carbamoyl and N-(1-carboxy-2-hydroxyethyl)carbamoyl groups.

Also, particularly preferred compounds of the invention are those compounds of formula (I) in which m is 3 and n is 2 or m is 2 and n is 3.

One class of compounds of the present invention are those compounds of formula (I) in which:

R$^1$ represents a carboxy group, a protected carboxy group, a tetrazolyl group, a carbamoyl group, a substituted carbamoyl group having one or two substituents selected from the group consisting of substituents (a), defined above, a hydroxymethylcarbonyl group, a protected hydroxymethylcarbonyl group, a hydroxymethyl group or a protected hydroxymethyl group;

R$^2$ and R$^1$ are independently selected from the group consisting of hydrogen atoms and hydroxy-protecting groups;

R$^4$ represents a hydrogen atom or a C$_1$—C$_4$ alkyl group;

R$^5$ represents a C$_1$-C$_{12}$ 12 alkyl group, a substituted C$_1$-C$_{12}$ alkyl group having at least one substituent selected from the group consisting of substituents (b$^1$) a C$_2$—C$_{12}$ alkenyl substituted C$_2$-C$_{12}$ alkenyl group having at least one substituent selected from the group consisting of substituents (b$^1$) a C$_2$-C$_{12}$ alkynyl group, a substituted C$_1$-C$_6$ alkynyl group having at least one substituent selected from the group consisting of substituents (b$^1$) or a group of formula —B—R$^6$, in which:

B represents a single bond, a C$_1$-C$_6$ alkylene group, a C$_1$-C$_6$ alkylene group in which the carbon chain is interrupted by at least one hetero-atom selected from the group consisting of oxygen atoms and sulfur atoms, or a C$_2$—C$_6$ alkylene group in which at least one of the carbon-carbon single bonds is replaced by a carbon-carbon double bond: and R$^6$ represents a C$_3$-C$_{10}$ cycloalkyl group, a substituted C$_3$-C$_{10}$ cycloalkyl group having ar least one substituent selected from the group consisting of C$_1$-C$_6$ alkyl groups, an aryl group, a heterocyclic group having 5 or 6 ring atoms of which from 1 to 3 are heteroatoms selected from the group consisting of nitrogen, oxygen and sulfur atoms;

A represents a group of formula —CH$_2$CH$_2$—, —CH=CH—, —C≡C—, —O—CH$_2$—or —S—CH$_2$—;

m is O or an integer from 1 to 3; and n is an integer from 2 to 5;

substituents (b$^1$)

halogen atoms and C$_1$-C$_4$ alkoxy groups;

and pharmaceutically acceptable salts and esters thereof

Preferred classes of compounds of the present invention are those compounds of formula (I), in which:

(1) R$^1$ represents a carboxy group, a C$_2$-C$_{11}$ alkoxycarbonyl group, a phenoxycarbonyl group which is unsubstituted or has at least one substituent selected from the group consisting of substituents (c). a naphthoyloxycarbonyl group, a carbamoyl group, a carbamoyl group having one or two substituents selected from the group consisting of C$_1$-C$_6$ alkyl groups, substituted C$_1$-C$_4$ alkyl groups having at least one substituent selected from the group consisting of substituents (a$^1$) phenyl groups and methanesulfonyl groups, a hydroxymethylcarbonyl group or a hydroxymethyl group.

(2) (R $^2$) and R$^3$ are the same and each represents a hydrogen atom.

(3) R$^4$ represents a hydrogen atom or an alkyl group.

(4) R$^5$ represents a C$_3$-C$_{10}$ alkyl group which is unsubstituted or has at least one substituent selected from the group consisting of fluorine atoms, chlorine atoms and $C_1$-$C_4$ alkoxy groups, a $C_5$-$C_{10}$ alkenyl group, a $C_5$-$C_{10}$ alkynyl group or a group of formula —B—$R^6$, in which:

B represents a single bond, a $C_1$-$C_4$ alkylene group or a $C_1$-$C_4$ alkylene group in which the carbon chain is interrupted by at least one hetero-atom selected from the group consisting of oxygen atoms and sulfur atoms; and $R^6$ represents a $C_3$-$C_{10}$ cycloalkyl group, a phenyl group which is unsubstituted or has at least one substituent selected from the group consisting of $C_1$-$C_4$ alkyl groups, $C_1$-$C_4$ alkoxy groups, $C_2$-$C_5$ aliphatic acylamino groups, trifluoromethyl groups and halogen atoms, or an aromatic heterocyclic group having 5 or 6 ring atoms of which from 1 to 3 are hetero-atoms selected from the group consisting of nitrogen, oxygen and sulfur atoms.

(5) A represents a trans-vinylene group.

(6) m is an integer from 2 to 5 and n is 2 or 3.

(7) m is 3 and n is 2 or m is 2 and n is 3.

(8) $R^1$ is as defined in (1) above, $R^2$ and $R^3$ are as defined in (2) above, $R^1$ is as defined in (3) above, $R^5$ is as defined in (4) above, A is as defined in (5) above and m and n are as defined in (6) above.

(9) $R^1$ is as defined in (1) above, $R^1$ and $R^1$ are as defined in (2) above, $R^4$ is as defined in (3) above, $R^5$ is as defined in (4) above, A is as defined in (5) above, m is 3 or 5 and n is 2.

(9) $R^1$ is as defined in (1) above, $R^2$ and $R^3$ are as defined in (2) above, $R^4$ is as defined in (3) above, $R^5$ is as defined in (4) above, A is as defined in (5) above, m is 3 or 5 and n is 2.

(10) $R^1$ represents a carboxy group, a $C_2$-$C_{11}$ alkoxycarbonyl group, a phenoxycarbonyl group which is unsubstituted or has at least one substituent selected from the group consisting of substituents (c), a carbamoyl group or a carbamoyl group having one substituent selected from the group consisting of $C_1$-$C_4$ alkyl groups, substituted $C_1$-$C_4$ alkyl groups having at least one substituent selected from the group consisting of substituents ($a^1$). phenyl groups and methanesulfonyl groups.

(11) $R^5$ represents a $C_5$-$C_{10}$ alkyl group, a $C_5$-$C_{10}$ alkenyl group, a $C_5$-$C_{10}$ alkynyl group or a group of formula —B—$R^6$, in which:

B represents a single bond, a $C_1$-$C_4$ alkylene group or a $C_1$-$C_4$ alkylene group in which the carbon chain is interrupted by at least one hetero-atom selected from the group consisting of oxygen atoms and sulfur atoms; and $^6$ represents a $C_3$-$C_6$ cycloalkyl group, a phenyl group which is unsubstituted or has at least one substituent Selected from the group consisting of $C_1$-$C_4$ alkyl groups, $C_1$-$C_4$ alkoxy groups, $C_2$-$C_5$ aliphatic acylamino groups, trifluoromethyl groups and halogen atoms, or an aromatic heterocyclic group having 5 or 6 ring atoms of which 1 is a hetero-atom selected from the group consisting of nitrogen, oxygen and sulfur atoms

(12) $R^1$ is as defined in (10) above, $R^2$ and $R^3$ are as defined in (2) above, $R^4$ is as defined in (3) above. $R^5$ is as defined in (11) above. A is as defined in (5) above and m and n are as defined in (7) above.

(13) $R^1$ is as defined in (10) above, $R^2$ and $R^3$ are as defined in (2) above, $R^4$ is as defined in (3) above, $R^5$ is as defined in (11) above, A is as defined in (5) above, m is 3 and n is 2.

(14) $R^1$ represents a carboxy group or a $C_2$-$C_{11}$ alkoxycarbonyl group.

(15) $R^5$ represents a $C_5$-$C_{10}$ alkyl group, a $C_5$-$C_{10}$ alkenyl group or a group of formula —B—$R^6$, in which:

B represents a single bond, a methylene group, an ethylene group or a group of formula —CH$_2$—O— or —CH(CH$_3$)—O—, and $R^6$ represents a $C_3$-$C_6$ cycloalkyl group, a phenyl group, an indolyl group or a substituted phenyl group having at least one substituent selected from the group consisting of $C_1$-$C_4$ alkyl groups, $C_1$-$C_4$ alkoxy groups, halogen atoms and $C_2$-$C_5$ aliphatic carboxylic acylamino groups.

(16) $R^1$ is as defined in (14) above, $R^2$, $R^3$ and $R^4$ are as defined in (12) above $R^5$ is as defined in (15) above A is as defined in (5) above and m and n are as defined in (7) above.

(17) $R^1$ is as defined in (14) above $R^2$, $R_3$, $R^4$, $R^5$ and A are as defined in (16) above, m is 3 is n 2.

(18) Compounds as defined in (1)-(17), above in which $R^4$ represents a hydrogen atom.

Where $R^1$ in the compounds of the invention represents a carboxy group, the resulting compounds are acids and hence can form salts and esters. There is no particular restriction upon the nature of such salts and esters, provided that, where they are intended for therapeutic use, they should be "pharmaceutically acceptable", which, as is well-known to those skilled in the art, means that they should not have a reduced activity (or unacceptably reduced activity) or an increased toxicity (or unacceptably increased toxicity) as compared with the free acids. Where the compounds are intended for non-therapeutic use, for example as intermediates in the preparation of other compounds, even these restrictions do not apply.

Examples of preferred esters of the compounds of the invention include the following:

$C_1$-$C_{10}$ alkyl esters, for example the methyl, ethyl, propyl, isopropyl, butyl, t-butyl, pentyl, hexyl, heptyl, octyl, nonyl and decyl esters;

$C_3$-$C_7$ cycloalkyl esters, for example where the cycloalkyl group is any one of those $C_3$-$C_7$ cycloalkyl groups described herein in relation to $R^6$;

aralkyl esters, in which the aryl part is preferably as defined above and the alkyl part is preferably a $C_1$-$C_3$, more preferably $C_1$ or $C_2$, alkyl group, for example the benzyl and p-bromobenzyl esters;

phenyl or naphthyl esters, in which the phenyl or naphthyl group is unsubstituted or substituted, preferably with at least one $C_1$-$C_4$ alkyl, aromatic acylamino or $C_2$-$C_5$ aliphatic acylamino group, for example the phenyl, tolyl and benzamidophenyl esters;

benzhydryl esters;

phenacyl esters; and geranyl esters.

Of these, the $C_1$-$C_{10}$ alkyl esters are preferred and the methyl esters are more preferred.

The compounds of the invention can likewise form salts which may, where the compounds are intended or therapeutic use, be pharmaceutically acceptable salts. Examples of such salts include:

salts with alkali or alkaline earth metals, such as the sodium, potassium, magnesium or calcium salts;

the ammonium salts; quaternary ammonium salts, for example the tetramethylammonium, tetraethylammonium, benzyltrimethylammonium, benzyltriethylammonium and phenyltriethylammonium salts;

salts with alkylamines, cycloalkylamines or aralkylamines, such as the methylamine, ethylamine, dimethylamine, diethylamine, trimethylamine, triethylamine, N-methyl-N-hexylamine, cyclopentylamine, dicyclohexylamine, benzylamine, dibenzylamine, α-phenylethylamine and ethylenediamine salts;

salts with heterocyclic amines, wherein the heterocyclic group is unsubstituted or has at least one $C_1$–$C_4$ alkyl substituent, for example the piperidine, morpholine, pyrrolidine, piperazine, pyridine, 1-methylpiperazine and 4-ethylmorpholine salts; and salts with amines containing a hydrophilic group, such as the monoethanolamine, ethyldiethanolamine and 2-amino-1-butanol salts.

The compounds of the invention can also, if desired, be employed in the form of an inclusion compound with a host compound, such as α-, β- or Ξ-cyclodextrin.

The compounds of the invention can exist in the form of various optical isomers, due to the presence of asymmetric carbon atoms in the cyclopentane ring and in the side chains or as geometric isomers due to the double bond when $R^5$ represents an alkenyl group. The compounds of the invention may be obtained in the form of mixtures of such isomers, in which case, each individual isomer may be obtained by conventional isolation and resolution techniques, or the compounds may be employed as a mixture of such isomers. Although all of the isomers are represented herein by a single formula, it will be understood that all of the possible isomers are included within the scope of the present invention.

Examples of specific compounds of the invention are given in the following formulae (I-1) and (I-2), in which the substituents are as defined in the corresponding one of Tables 1 and 2 [i.e. Table 1 relates to formula (I-1) and Table 2 relates to formula (I-2)]. In the Tables, the following abbreviations are used:

| Ac | acetyl |
| Boz | benzoyl |
| Bu | butyl |
| Bz | benzyl |
| Car | carbamoyl |
| Et | ethyl |
| Fur | furyl |
| Hep | heptenyl |
| Hex | hexenyl |
| Hp | heptyl |
| Hx | hexyl |
| cHx | cyclohexyl |
| Ind | indolyl |
| Me | methyl |
| Mec | methoxycarbonyl |
| Np | naphthyl |
| Pen | pentenyl |
| Ph | phenyl |
| Pn | pentyl |
| cPn | cyclopentyl |
| Pr | propyl |
| TFM | trifluoromethyl |
| Thi | thienyl |

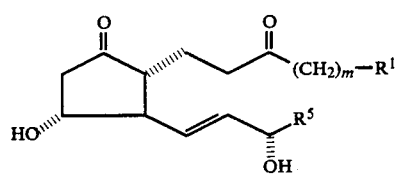

(I-1)

(I-2)

TABLE 1

| Cpd. No. | $R^1$ | $R^5$ | m |
|---|---|---|---|
| 1-1 | —COOH | Pn | 3 |
| 1-2 | —COOH | Hx | 3 |
| 1-3 | —COOH | 5-ClPn | 3 |
| 1-4 | —COOH | 5-FPn | 3 |
| 1-5 | —COOH | 5-MeOPn | 3 |
| 1-6 | —COOH | 5-EtOPn | 3 |
| 1-7 | —COOH | 1-MePn | 3 |
| 1-8 | —COOH | 1,1-diMePn | 3 |
| 1-9 | —COOH | 2-MePn | 3 |
| 1-10 | —COOH | 2,2-diMePn | 3 |
| 1-11 | —COOH | 1,1-diMeHx | 3 |
| 1-12 | —COOH | 5-F-1-MePn | 3 |
| 1-13 | —COOH | 5-F-1,1-diMePn | 3 |
| 1-14 | —COOH | 5-Cl-1,1-diMePn | 3 |
| 1-15 | —COOH | 5-MeO-1,1-diMePn | 3 |
| 1-16 | —COOH | 5-EtO-1,1-diMePn | 3 |
| 1-17 | —COOH | 2-EtO-1,1-diMeEt | 3 |
| 1-18 | —COOH | 3-MeO-1,1-diMePr | 3 |
| 1-19 | —COOH | 2-MeHx | 3 |
| 1-20 | —COOH | 1,1-diMeHp | 3 |
| 1-21 | —COOH | 4-Pen | 3 |
| 1-22 | —COOH | 1-Me-4-Pen | 3 |
| 1-23 | —COOH | 1,1-diMe-4-Pen | 3 |
| 1-24 | —COOH | 1,1-diMe-5-Hex | 3 |
| 1-25 | —COOH | 1,1-diMe-6-Hep | 3 |
| 1-26 | —COOH | 2-Me-4-Pen | 3 |
| 1-27 | —COOH | 2-Me-5-Hex | 3 |
| 1-28 | —COOH | 2,6-diMe-5-Hep | 3 |
| 1-29 | —COOH | 4-Me-3-Pen | 3 |
| 1-30 | —COOH | 6-Me-5-Hep | 3 |
| 1-31 | —COOH | 1,6-diMe-5-Hep | 3 |
| 1-32 | —COOH | 1,1,6-triMe-5-Hep | 3 |
| 1-33 | —COOH | 1,1,4-triMe-3-Pen | 3 |
| 1-34 | —COOH | 1,1,5-triMe-4-Hex | 3 |
| 1-35 | —COOH | 1,4-diMe-3-Pen | 3 |
| 1-36 | —COOH | PhoMe | 3 |
| 1-37 | —COOH | Ph | 3 |
| 1-38 | —COOH | cPn | 3 |
| 1-39 | —COOH | cHx | 3 |
| 1-40 | —COOH | 2-Fur | 3 |
| 1-41 | —COOH | 2-Thi | 3 |
| 1-42 | —COOH | 3-Ind | 3 |
| 1-43 | —COOH | p-FPh | 3 |
| 1-44 | —COOH | m-FPh | 3 |
| 1-45 | —COOH | p-ClPh | 3 |
| 1-46 | —COOH | p-MeOPh | 3 |
| 1-47 | —COOH | 3-IndMe | 3 |
| 1-48 | —COOH | 2-FurMe | 3 |
| 1-49 | —COOH | cHxMe | 3 |
| 1-50 | —COOH | 2-cHxEt | 3 |
| 1-51 | —COOH | p-ClPhOMe | 3 |
| 1-52 | —COOH | m-ClPhOMe | 3 |
| 1-53 | —COOH | o-ClPhOMe | 3 |
| 1-54 | —COOH | p-FPhOMe | 3 |
| 1-55 | —COOH | m-FPhOMe | 3 |
| 1-56 | —COOH | o-FPhOMe | 3 |
| 1-57 | —COOH | p-MeOPhOMe | 3 |
| 1-58 | —COOH | 3,5-diMePhOMe | 3 |
| 1-59 | —COOH | BzOMe | 3 |
| 1-60 | —COOH | 2-PhEtOMe | 3 |
| 1-61 | —COOH | p-EtPhOMe | 3 |
| 1-62 | —COOH | p-MePhOMe | 3 |
| 1-63 | —COOH | p-(AcNH)PhOMe | 3 |
| 1-64 | —COOH | p-(MeNH)PhOMe | 3 |
| 1-65 | —COOH | cHxOMe | 3 |
| 1-66 | —COOH | 2-PhEt | 3 |
| 1-67 | —COOH | PhSMe | 3 |
| 1-68 | —COOH | p-FPhSMe | 3 |

TABLE 1-continued

| Cpd. No. | R¹ | R⁵ | m |
|---|---|---|---|
| 1-69 | —COOH | m-FPhSMe | 3 |
| 1-70 | —COOH | p-ClPhSMe | 3 |
| 1-71 | —COOH | 3,4-diClPhOMe | 3 |
| 1-72 | —COOH | 3,4-diFPhOMe | 3 |
| 1-73 | —COOH | p-BrPhOMe | 3 |
| 1-74 | —COOH | m-BrPhOMe | 3 |
| 1-75 | —COOH | m-TFMPhOMe | 3 |
| 1-76 | —COOH | p-TFMPhOMe | 3 |
| 1-77 | —COOH | p-PrPhOMe | 3 |
| 1-78 | —COOH | m-PrPhOMe | 3 |
| 1-79 | —COOH | p-MeSPhOMe | 3 |
| 1-80 | —COOH | 2-(p-ClPhO)Et | 3 |
| 1-81 | —COOH | 2-(m-ClPhO)Et | 3 |
| 1-82 | —COOH | 1-(p-ClPhO)Et | 3 |
| 1-83 | —COOH | 1-(m-ClPhO)Et | 3 |
| 1-84 | —COOH | 2-(p-FPhO)Et | 3 |
| 1-85 | —COOH | 1-PhOEt | 3 |
| 1-86 | —COOH | 1-cHxOEt | 3 |
| 1-87 | —COOH | 1-(3-Ind)Et | 3 |
| 1-88 | —COOH | 1-(p-MeOPhO)Et | 3 |
| 1-89 | —COOH | 1-BzOEt | 3 |
| 1-90 | —COOH | 1-(p-EtPhO)Et | 3 |
| 1-91 | —COOH | 1-PhSEt | 3 |
| 1-92 | —COOH | 1-(p-FPhS)Et | 3 |
| 1-93 | —COOH | 1-Me-1-PhOEt | 3 |
| 1-94 | —COOH | 1-Me-1-(p-ClPhO)Et | 3 |
| 1-95 | —COOMe | Pn | 3 |
| 1-96 | —COOMe | Hx | 3 |
| 1-97 | —COOMe | 5-ClPn | 3 |
| 1-98 | —COOMe | 5-FPn | 5 |
| 1-99 | —COOMe | 5-MeOPn | 5 |
| 1-100 | —COOMe | 5-EtOPn | 5 |
| 1-101 | —COOMe | 1-MePn | 3 |
| 1-102 | —COOMe | 1,1-diMePn | 3 |
| 1-103 | —COOEt | 1,1-diMePn | 3 |
| 1-104 | —COOMe | 2-MePn | 3 |
| 1-105 | —COOMe | 2,2-diMePn | 3 |
| 1-106 | —COOMe | 1,1-diMeHx | 3 |
| 1-107 | —COOMe | 5-F-1-MeHx | 3 |
| 1-108 | —COOMe | 5-F-1,1-diMePn | 3 |
| 1-109 | —COOMe | 5-Cl-1,1-diMePn | 3 |
| 1-110 | —COOMe | 5-MeO-1,1-diMePn | 3 |
| 1-111 | —COOMe | 5-EtO-1,1-diMePn | 3 |
| 1-112 | —COOMe | 2-EtO-1,1-diMeEt | 3 |
| 1-113 | —COOMe | 3-MeO-1,1-diMePr | 3 |
| 1-114 | —COOMe | 2-MeHx | 3 |
| 1-115 | —COOMe | 1,1-diMeHp | 3 |
| 1-116 | —COOMe | 2,6-diMeHp | 3 |
| 1-117 | —COOMe | 4-Pen | 3 |
| 1-118 | —COOMe | 1-Me-4-Pen | 5 |
| 1-119 | —COOMe | 1,1-diMe-4-Pen | 3 |
| 1-120 | —COOMe | 1,1-diMe-5-Hex | 3 |
| 1-121 | —COOMe | 1,1-diMe-6-Hep | 3 |
| 1-122 | —COOMe | 2-Me-4-Pen | 3 |
| 1-123 | —COOMe | 2-Me-5-Hex | 3 |
| 1-124 | —COOMe | 2,6-diMe-5-Hep | 3 |
| 1-125 | —COOMe | 4-Me-3-Pen | 3 |
| 1-126 | —COOMe | 6-Me-5-Hep | 3 |
| 1-127 | —COOMe | 1,6-diMe-5-Hep | 3 |
| 1-128 | —COOMe | 1,1,6-triMe-5-Hep | 3 |
| 1-129 | —COOMe | 1,1,4-triMe-3-Pen | 3 |
| 1-130 | —COOMe | 1,1,5-triMe-4-Hex | 3 |
| 1-131 | —COOMe | 1,4-diMe-3-Pen | 3 |
| 1-132 | —COOMe | PhOMe | 3 |
| 1-133 | —COOEt | PhOMe | 3 |
| 1-134 | —COOMe | Ph | 3 |
| 1-135 | —COOMe | cPn | 3 |
| 1-136 | —COOMe | cHx | 3 |
| 1-137 | —COOMe | 2-Thi | 3 |
| 1-138 | —COOMe | 2-Fur | 5 |
| 1-139 | —COOMe | 3-Ind | 3 |
| 1-140 | —COOMe | p-FPh | 5 |
| 1-141 | —COOMe | m-FPh | 5 |
| 1-142 | —COOMe | p-ClPh | 3 |
| 1-143 | —COOMe | p-MeOPh | 3 |
| 1-144 | —COOMe | 3-IndMe | 3 |
| 1-145 | —COOMe | 2-FurMe | 3 |
| 1-146 | —COOMe | cHxMe | 3 |
| 1-147 | —COOMe | 2-cHxEt | 3 |
| 1-148 | —COOMe | p-ClPhOMe | 3 |
| 1-149 | —COOMe | m-ClPhOMe | 3 |
| 1-150 | —COOMe | o-ClPhOMe | 3 |
| 1-151 | —COOMe | p-FPhOMe | 3 |
| 1-152 | —COOMe | m-FPhOMe | 3 |
| 1-153 | —COOMe | o-FPhOMe | 3 |
| 1-154 | —COOMe | p-MeOPhOMe | 3 |
| 1-155 | —COOMe | 3,5-diMePhOMe | 3 |
| 1-156 | —COOMe | BzOMe | 3 |
| 1-157 | —COOMe | o-MeOPhOMe | 3 |
| 1-158 | —COOMe | p-EtPhOMe | 3 |
| 1-159 | —COOMe | p-MePhOMe | 3 |
| 1-160 | —COOMe | p-(AcNH)PhOMe | 3 |
| 1-161 | —COOMe | p-(MeNH)PhOMe | 3 |
| 1-162 | —COOMe | cHxOMe | 3 |
| 1-163 | —COOMe | 2-PhEt | 3 |
| 1-164 | —COOMe | PhSMe | 3 |
| 1-165 | —COOMe | p-FPhSMe | 3 |
| 1-166 | —COOMe | m-FPhSMe | 5 |
| 1-167 | —COOMe | p-ClPhSMe | 3 |
| 1-168 | —COOMe | 3,4-diClPhOMe | 3 |
| 1-169 | —COOMe | 3,4-diFPhOMe | 3 |
| 1-170 | —COOMe | p-BrPhOMe | 3 |
| 1-171 | —COOMe | m-BrPhOMe | 3 |
| 1-172 | —COOMe | m-TFMPhOPMe | 3 |
| 1-173 | —COOMe | p-TFMPhOMe | 3 |
| 1-174 | —COOMe | p-PrPhOMe | 3 |
| 1-175 | —COOMe | m-PrPhOMe | 3 |
| 1-176 | —COOMe | p-MeSPhOMe | 3 |
| 1-177 | —COOMe | 2-(p-ClPhO)Et | 3 |
| 1-178 | —COOMe | 2-(m-ClPhO)Et | 3 |
| 1-179 | —COOMe | 1-(p-ClPhO)Et | 3 |
| 1-180 | —COOMe | 1-(m-ClPhO)Et | 3 |
| 1-181 | —COOMe | 2-(p-FPhO)Et | 3 |
| 1-182 | —COOMe | 1-PhOEt | 3 |
| 1-183 | —COOMe | 3-ThiOMe | 3 |
| 1-184 | —COOMe | 1-(3-Ind)Et | 5 |
| 1-185 | —COOMe | 1-(p-MeOPhO)Et | 3 |
| 1-186 | —COOMe | 1-BzOEt | 3 |
| 1-187 | —COOMe | 1-(p-EtPhO)Et | 3 |
| 1-188 | —COOMe | 1-PhSEt | 3 |
| 1-189 | —COOMe | 1-(p-FPhS)Et | 3 |
| 1-190 | —COOMe | 1-Me-1-PhOEt | 3 |
| 1-191 | —COOMe | 1-Me-1-(p-ClPhO)Et | 3 |
| 1-192 | —COOPh | 1,1-diMePn | 3 |
| 1-193 | —COOPh | PhOMe | 3 |
| 1-194 | —COO(2-Np) | 1,1-diMePn | 3 |
| 1-195 | —COO(2-Np) | PhOMe | 3 |
| 1-196 | —COO[p-(BozNH)Ph] | 1,1-diMePn | 3 |
| 1-197 | —COO[p-(BozNH)Ph] | 1,1-diMe-5-Hex | 3 |
| 1-198 | —COO[p-(BozNH)Ph] | PhOMe | 3 |
| 1-199 | —COO[p-(BozNH)Ph] | p-ClPhOMe | 3 |
| 1-200 | —COO[p-(BozNH)Ph] | m-ClPhOMe | 3 |
| 1-201 | —COO[p-(AcNH)Ph] | 1,1-diMePn | 3 |
| 1-202 | —COO[p-(AcNH)Ph] | PhOMe | 3 |
| 1-203 | —COO[p-(p-MeOBoz-NH)Ph] | PhOMe | 3 |
| 1-204 | —COO(p-CarPh) | 1,1-diMePn | 3 |
| 1-205 | —COO(p-CarPh) | PhOMe | 3 |
| 1-206 | —COO[p-(diMeCar)Ph] | PhOMe | 3 |
| 1-207 | —COO[p-(p-HO-BozNH)Ph] | PhOMe | 3 |
| 1-208 | Car | PhOMe | 3 |
| 1-209 | N-(HOOCMe)Car | PhOMe | 3 |
| 1-210 | N-(1-HOOCEt)Car | PhOMe | 3 |
| 1-211 | N-(1-HOOC-2-PhEt)Car | PhOMe | 3 |
| 1-212 | N-(1-HOOC-3-MeBu)Car | PhOMe | 3 |
| 1-213 | N-(MecMe)Car | PhOMe | 3 |
| 1-214 | N-(1-HOOC-2-HOEt)Car | PhOMe | 3 |

TABLE 2

| Cpd. No. | R¹ | R⁵ |
|---|---|---|
| 2-1 | —COOH | 1,1-diMePn |
| 2-2 | —COOH | 1,1-diMe-5-Hex |

TABLE 2-continued

| Cpd. No. | $R^1$ | $R^5$ |
|---|---|---|
| 2-3 | —COOH | PhOMe |
| 2-4 | —COOMe | Pn |
| 2-5 | —COOMe | 2-MeHx |
| 2-6 | —COOMe | 1,1-diMePn |
| 2-7 | —COOMe | 1,1-diMeHx |
| 2-8 | —COOMe | 1,1-diMe-5-Hex |
| 2-9 | —COOMe | 2-EtO-1,1-diMeEt |
| 2-10 | —COOMe | PhOMe |
| 2-11 | —COOMe | 2-PhOEt |
| 2-12 | —COOMe | p-ClPhOMe |
| 2-13 | —COOMe | m-ClPhOMe |
| 2-14 | —COOMe | o-ClPhOMe |
| 2-15 | —COOPh | PhOMe |
| 2-16 | —COO(2-Np) | 1,1-diMePn |
| 2-17 | —COO(2-Np) | PhOMe |
| 2-18 | —COO[p-(BozNH)Ph] | 1,1-diMePn |
| 2-19 | —COO[p-(BozNH)Ph] | PhOMe |
| 2-20 | —COO[p-(AcNH)Ph] | PhOMe |
| 2-21 | —COO(p-CarPh) | PhOMe |
| 2-22 | —COO[p-(p-MeO-BozNH)Ph] | PhOMe |

Of the compounds listed above, the following are preferred: Compounds No. 1-8, 1-11, 1-36, 1-51, 1-52, 1-71, 1-75, 1-85, 1-102, 1-104, 1-106, 1-114, 1-115, 1-120, 1-132, 1-134, 1-144, 1-148, 1-149, 1-151, 1-152, 1-156, 1-162, 1-168, 1-170, 1-179, 1-180, 1-182, 1-183, 1-190, 2-6, 2-7, 2-10, 2-11 and 2-12, and the following are most preferred:

1-36. 5-Oxo-16-phenoxy-17,18,19, 20-tetranorprostaglandin $E_1$;

1-102. 5-Oxo-16,16-dimethylprostaglandin $E_1$ methyl ester;

104. 5-Oxo-17-methylprostaglandin $E_1$ methyl ester;

132. 5-Oxo-16-phenoxy-17,18,19,20-tetranorprostaglandin $E_1$ methyl ester;

1-148, 5-Oxo-16-(p-chlorophenoxy)-17,18,19,20tetranorprostaglandin $E_1$ methyl ester;

1-149. 5-Oxo-16-(m-chlorophenoxy) 17,18,19,20-tetranorprostaglandin $E_1$ methyl ester;

1-151. 5-Oxo-16-(p-fluorophenoxy)-17,18,19-tetranorprostaqlandin $E_1$ methyl ester;

1-152. 5-Oxo-16-(m-fluorophenoxy)-17,18,19,20tetranorprostaglandin $E_1$ methyl ester;

1-182. 5-Oxo-16-methyl-16-phenoxy-17,18,19,20-tetranorprostaglandin $E_1$ methyl ester;

2-6. 4-Oxo-16,16-dimethylprostaglandin $E_1$ methyl ester;

2-10. Methyl 4.9-dioxo-11α,15α-dihydroxy16-phenoxy-17,18,19,20-tetranorprost-13(E)-enoate.

2-12. Methyl 4,9-dioxo-11a,15α-dihydroxy-16-p-chlorophenoxy-17,18,19,20-tetranorprost-13(E)-enoate.

Also most preferred are the corresponding carboxylic acids and pharmaceutically acceptable salts of the above 12 compounds.

The compounds of the invention may be prepared as illustrated by the following reaction schemes:

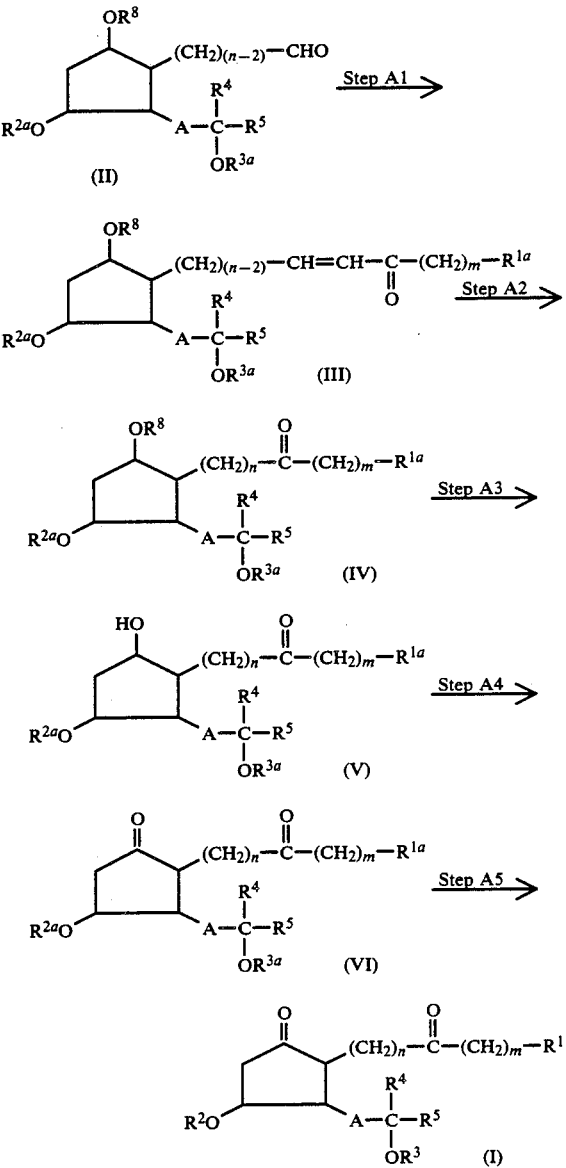

Method A

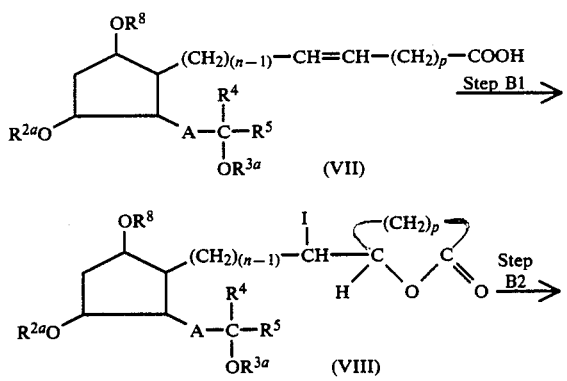

Method B

-continued
Method B
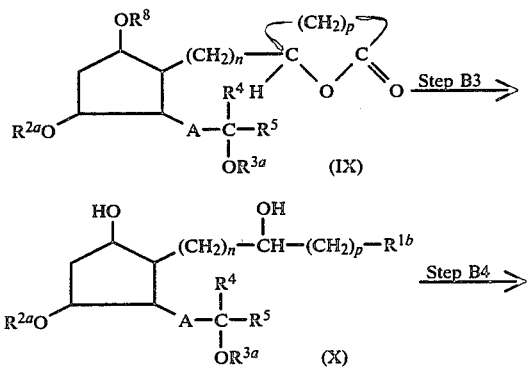
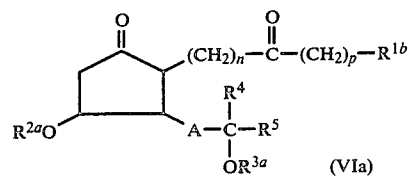
Method C
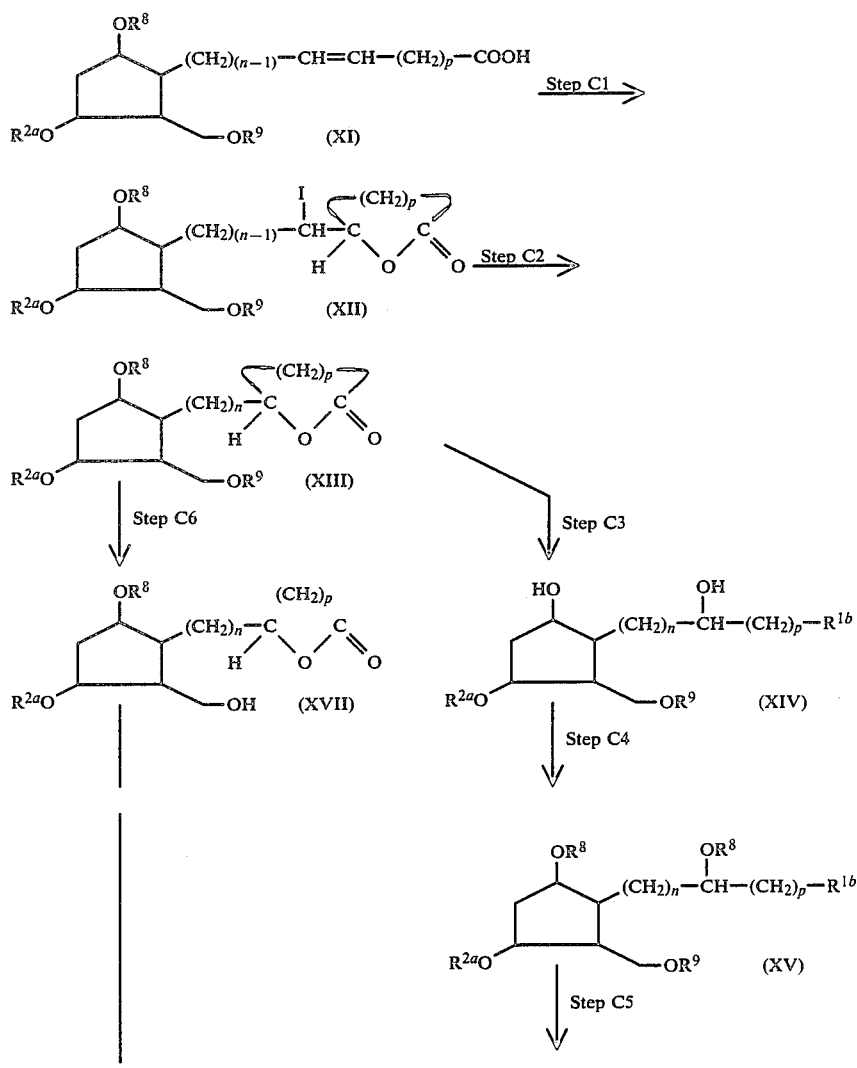

Method C

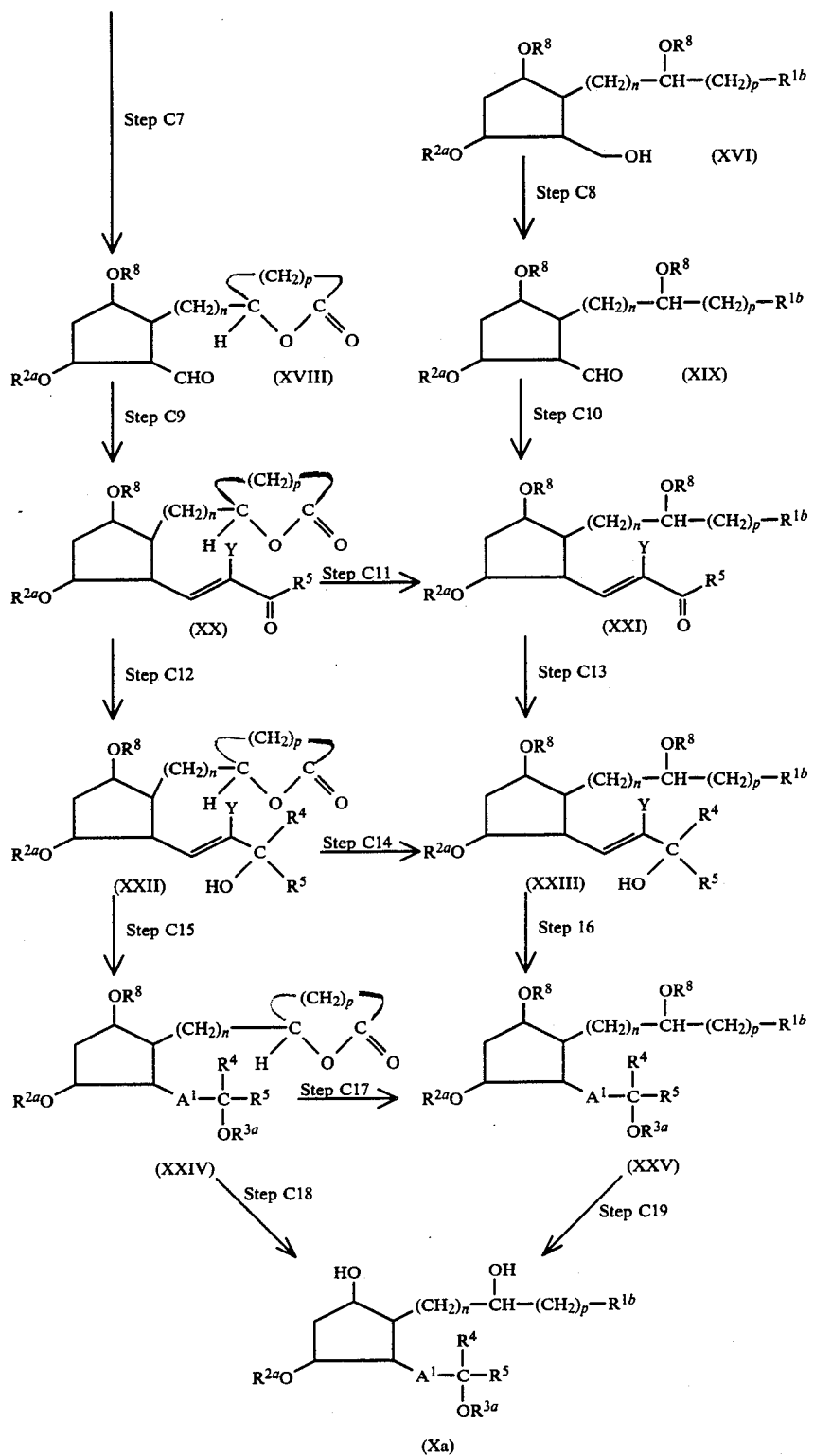

In the above formulae, $R^1$, $R^2$, $R^3$, $R^4$, $R^5$, A, m and n are as defined above, $R^{1a}$ represents a carboxy group, a protected carboxy group, a terrazolyl group, a hydroxymethyl group or a protected hydroxymethyl group, $R^{1b}$ represents a carboxy group or a protected carboxy group, $R^{2a}$, $R^{3a}$, $R^8$ $R^9$ represent hydroxy-protecting groups and, where the compound contains two such groups represented by the same symbol, these groups may be the same or different, $A^1$ represents a vinylene or ethynylene group. Y represents a hydrogen atom or a halogen atom, and p represents the integer 2 or 3.

METHOD A

This comprises Steps A1 to A5.

Step A1

In Step A1 of Method A a compound of general formula (III) is prepared by reacting an aldehyde derivative of formula (II) with a Wittig reagent or modified Wittig reagent of formula (XXVI):

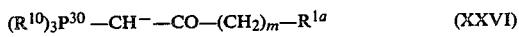
$(R^{10})_3P^{30}—CH^-—CO—(CH_2)_m—R^{1a}$ (XXVI)

or of formula (XXVII):

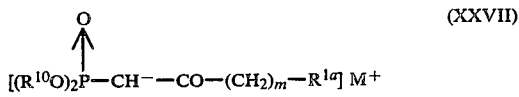
$[(R^{10}O)_2\overset{O}{\overset{\|}{P}}—CH^-—CO—(CH_2)_m—R^{1a}] \ M^+$ (XXVII)

(in the above formulae, $R^{1a}$ and m are as defined above, $R^{10}$ represents a $C_1$–$C_4$ alkyl group, such as a as a methyl or butyl group, or an aryl group, such as a phenyl or tolyl group, and M represents an alkali metal, such as lithium or sodium).

The Wittig reagent or modified Wittig reagent having the aforementioned general formula (XXVI) or (XXVII) and used in this reaction can be obtained in a conventional manner by reacting a compound of formula (XXVI'):

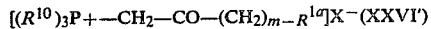
$[(R^{10})_3P^+—CH_2—CO—(CH_2)_m—R^{1a}]X^-$ (XXVI')

or of formula (XXVII'):

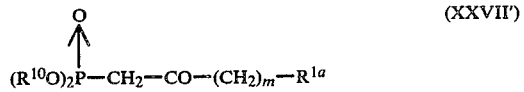
$(R^{10}O)_2\overset{O}{\overset{\|}{P}}—CH_2—CO—(CH_2)_m—R^{1a}$ (XXVII')

(in the above formulae, $R^{1a}$, $R^{10}$ and m are as defined above, and X represents a halogen atom, such as chlorine or bromine), in the presence of a solvent with an alkali metal base. The nature of the base is not critical, provided that it has no adverse effect on other parts of the molecule, and any base commonly used in reactions of this kind may be employed. Examples include: alkali metal hydrides, such as sodium hydride or potassium hydride; alkali metal alkoxides such as sodium methoxide sodium ethoxide or potassium t-butoxide: alkali metal amides, such as sodium amide or potassium amide; alkyl alkali metal compounds, such as butyllithium; alkali metal dimethyl sulfoxide anions, such as the sodium dimethyl sulfoxide anion; alkali metal hydroxides, such as sodium hydroxide or potassium hydroxide; and alkali metal carbonates, such as sodium carbonate or potassium carbonate.

The nature of the solvent employed in the reaction is equally not critical, and any solvent commonly employed in Wittig reactions may also be employed here. Examples of suitable solvents include inert organic solvents such as, for example: ethers, such as diethyl ether, tetrahydrofuran, dioxane or dimethoxyethane; thioethers, such as sulfolane; hydrocarbons, which may be aliphatic or aromatic hydrocarbons, such as benzene, toluene or hexane; dialkyl sulfoxides, such as dimethyl sulfoxide; aliphatic acid dialkylamides, such as dimethylformamide or dimethylacetamide; halogenated hydrocarbons, particularly halogenated aliphatic hydrocarbons, such as methylene chloride or chloroform; phosphoric acid triamides, such as hexamethylphosphoric acid triamide (HMpA); alcohols, such as methanol or ethanol; water; and mixtures of any two or more thereof. The reaction is preferably carried out in an atmosphere of an inert gas, such as nitrogen, argon or helium. The reaction will take place over a wide range of temperatures, and the precise reaction temperature is not particularly critical; we normally find it convenient to carry out the reaction at a temperature in the range from $-10°$ C. to the boiling point of the solvent employed, but the reaction is more preferably carried out at around room temperature The time required for the reaction will vary depending upon many factors, notably the reaction temperature but a period of from 6 to 50 hours will usually suffice.

The compound of formula (II) used as the starting material in this step is a known compound or can be prepared without difficulty by known methods [e.g. R.A. Johnson et al., J. Org. Chem., 45, 1121 (1980)].

After the reaction is complete, the desired compound produced by the Wittig reaction can be recovered from the reaction mixture by conventional means. For example, a suitable recovery procedure comprises: addinq ice-water to the reaction mixture; treating the mixture, if required, with an acid; extracting it with an organic solvent, such as an ether; washing the extract with water; drying it; and then removing the solvent by distillation, if necessary under reduced pressure, to give the desired compound.

Step A2

In Step A2, a compound of formula (IV) is prepared by reducing the ethylenically unsaturated double bond of the compound of formula (III).

Any reaction which can be used for the selective reduction of a double bond of an $\alpha,\beta$-unsaturated carbonyl group may be employed without any particular restriction, but catalytic reduction is preferred.

Any catalyst commonly used in this type of reduction may also be used in this step, but preferred examples include palladium-on-carbon, platinum-on-carbon, rhodium-on-carbon, platinum dioxide or $RhCl(Ph_3P)_3$.

There is no particular restriction on the solvent to be employed, provided that it does not interfere with the reaction, and examples include: alcohols, such as methanol or ethanol; hydrocarbons, which may be aliphatic or aromatic, such as hexane, benzene or toluene; and esters, such as ethyl acetate.

The reaction will take place over a wide range of temperatures, and the precise reaction temperature is not particularly critical; we normally find it convenient to carry out the reaction at a temperature in the range from $-30°$ C. to room temperature. The time required for the reaction will vary depending upon many factors, notably the reaction temperature employed but a period of from 10 minutes to 2 hours will usually suffice.

After the reaction is complete, the desired compound produced by this step can be recovered from the reaction mixture by conventional means. For example, one suitable recovery procedure comprises: separating the catalyst by filtration; removing the solvent by distillation under reduced pressure; and adding ice-water to the residue. The mixture may then be extracted with a water-immiscible organic solvent and the solvent may be removed by distillation under reduced pressure, to give the desired compound.

Step A3

In Step A3, a compound of formula (V) is prepared by removing the hydroxy-protecting group $R^8$ from the compound of formula (IV). The reaction to be used will vary, depending upon the nature of the protecting group.

When the hydroxy-protecting group is a lower aliphatic or aromatic acyl group, it may be removed by a conventional hydrolysis reaction or solvolysis reaction using an acid or base. There is no particular restriction on the nature of the acid or base to be used, and any commonly employed in conventional hydrolysis reactions or solvolysis reactions may also be employed here. The reaction is preferably carried out under basic conditions, using a hydroxide of an alkali metal or of an alkaline earth metal, such as, for example, lithium hydroxide, sodium hydroxide, potassium hydroxide, calcium hydroxide or barium hydroxide, or an alkali metal carbonate, such as potassium carbonate The nature of the solvent to be employed in this reaction is not critical, provided that it has no adverse effect on the reaction, and any solvent commonly employed in hydrolysis reaction may equally be employed here. Examples include; alcohols, such as methanol, ethanol, propanol or isopropanol; ethers, such as diethyl ether, tetrahydrofuran, dioxane or dimethoxyethane; dialkyl sulfoxides, such as dimethyl sulfoxide: or a mixture of any one or more of these organic solvents with water.

The reaction will take place over a wide range of temperatures, and the precise reaction temperature is not particularly critical; we normally find it convenient to carry out the reaction at a temperature in the range from around room temperature to the boiling point of the solvent employed. The time required for the reaction will vary depending upon many factors, notably the reaction temperature employed, but a period of from 1 to 12 hours will usually suffice.

When the protecting group is an aralkyl group, it can be removed by contacting the corresponding compound with a reducing agent in an inert solvent. There is no particular restriction on the nature of the reducing agent to be employed, provided that it does not interfere with the remainder of the molecule. Examples of suitable reducing agents include alkali metals, such as lithium, sodium or potassium. The reaction is preferably carried out in liquid ammonia or in a mixture of liquid ammonia with an ether such as diethyl ether or tetrahydrofuran. The reaction temperature is preferably relatively low in order to avoid side reactions, but is otherwise not critical. A suitable temperature is in the range from $-78°$ C. to $-20°$ C. The time required for the reaction will vary depending upon many factors, notably the reaction temperature employed, but a period of from 20 minutes to 6 hours will usually suffice.

When the protecting group is a 4-methoxybenzyl group, it can be removed by treating the compound with cerium ammonium nitrate at around room temperature in aqueous acetone, or by treating it with an oxidizing agent, such as dichlorodicyanoquinone or sodium persulfate.

When the protecting group is a heterocyclic group, a methyl group which has an alkoxy or aralkyloxy substituent, a 1-alkoxyethyl group or a trityl group, it can be removed with ease by contacting it with an acid. Suitable acids include organic acids (including: carboxylic acids, such as, for example, formic acid, acetic acid, trifluoroacetic acid propionic acid butyric acid, oxalic acid, malonic acid; and sulfonic acids, such as methanesulfonic acid, benzenesulfonic acid, p-toluenesulfonic acid or camphorsulfonic acid) and mineral acids, such as hydrochloric acid hydrobromic acid or sulfuric acid. The reaction may be carried out in the presence or absence of a solvent but the use of a solvent is preferred, in order to enable the reaction to proceed smoothly. The nature of the solvent employed in the reaction is not critical, provided that it does not interfere with the reaction. Suitable solvents include: water; alcohols, such as methanol or ethanol; ethers, such as tetrahydrofuran or dioxane; ketones, such as acetone or methyl ethyl ketone; or a mixture of any one or more of these organic solvent with water.

The reaction will take place over a wide range of temperatures, and the precise reaction temperature chosen is not particularly critical; we normally find it convenient to carry out the reaction at a temperature in the range from around room temperature to the boiling point of the solvent employed. The time required for the reaction will vary depending upon many factors, notably the reaction temperature employed, but a period of from 30 minutes to 10 hours will usually suffice.

When the protecting group is a methylthiomethyl group, this can also be removed by treating the compound with mercuric chloride in aqueous acetonitrile.

When the protecting group is a tri(lower alkyl)-or diaryl(lower alkyl)- silyl group, it can be removed with ease by contacting the compound with water or with water containing an acid or base. There is no particular restriction on the nature of the acid or base to be used, provided that it has no adverse effect on other parts of the molecule, and examples of suitable acids include organic acids (such as formic acid, acetic acid propionic acid. Butyric acid oxalic acid or malonic acid) and mineral acids (such as hydrochloric acid, hydrobromic acid or sulfuric acid): examples of suitable bases include alkali or alkaline earth metal hydroxides (such as potassium hydroxide or calcium hydroxide) and alkali or alkaline earth metal carbonates (such as potaSSium carbonate or calcium carbonate). When the reaction is carried out using water as the solvent, there is no particular need to use any other solvent. However, if another solvent is to be employed, a mixture of water with an organic solvent such as an ether, for example tetrahydrofuran or dioxane, or an alcohol, for example methanol or ethanol, is preferred. The reaction temperature is not critical, but the reaction is usually preferably carried out at about room temperature. The time required for the reaction will vary depending upon many factors, notably the reaction temperature employed, but a period of from 30 minutes to 5 hours will usually suffice.

When the protecting group is a t-butyldimethylsilyl group or a diphenyl-t-butylsilyl group, it may be removed by treating the compound with a compound generating fluoride anions, for example tetrabutylammonium fluoride, in the presence of an ether, such as tetrahydrofuran or dioxane.

After the reaction is complete, the desired compound can be recovered from the reaction mixture by conventional means. For example, one suitable recovery procedure comprises: if necessary, removing the solvent from the mixture by distillation, if necessary under reduced pressure; pouring the residue into ice-water; if required, neutralizing it; and extracting it with a suitable organic solvent. The extract may be washed with water, dried and the solvent removed by distillation to give the desired compound.

It is desirable, in this step, that the protecting group represented by $R^8$ should be so selected as to be removable appropriately under acidic. basic or neutral conditions, and so enable it to be removable selectively, independently from the other hydoxyprotecting groups, i.e., the groups represented by or included in the groups represented by $R^{1a}$, $R^{2a}$ and 3a.

Step A4

In Step A4, a compound of formula (VI) is prepared by oxidizing the compound of formula (V).

There is no particular limitation on the nature of the oxidizing agent employed in this step, provided that it has no adverse effect on other parts of the molecule, and any oxidizing agent commonly used in this type of reaction may equally be employed here. Examples of suitable oxidizing agents include: chromic acid derivatives, such as chromic anhydride, chromic anhydride-pyridine complex (Collins reagent), chromic anhydride-concentrated sulfuric acid water (Jones reagent, sodium bichromate or potassium bichromate, organic active halogen compounds, such as N-bromoacetamide, N-bromosuccinimide, N-bromophthalimids, N-chloro-p-toluenesulfonamide or N-chlorobenzenesulfonamide; aluminum alkoxides, such as aluminum t-butoxide or aluminum isopropoxide; dimethyl sulfoxide-dichlorocarbodiimide; pyridine sulfur trioxide complexes; and mixtures of an activated acyl derivative (e.g. oxalyl dichloride or trifluoroacetic anhydride) with dimethyl sulfoxide and with an organic amine (e.g. triethylamine or pyridine). However, a chromic anhydride-pyridine complex, a pyridine-sulfur trioxide complex or a mixture of oxalyl dichloride with dimethyl sulfoxide and with an organic amine is preferred.

The reaction is preferably carried out in the presence of an inert organic solvent, the nature of which is not critical, provided that it has no adverse effect on the reaction Examples of suitable solvents include: halogenated hydrocarbons, especially halogenated aliphatic hydrocarbons, such as methylene chloride, chloroform or carbon tetrachloride; ethers, such as diethyl ether, tetrahydrofuran or dioxane., ketones, such as acetone or methyl ethyl ketone; and sulfoxides, such as dimethyl sulfoxide.

The reaction will take place over a wide range of temperatures, and the precise reaction temperature chosen is not critical to the invention. In general, we find it convenient to carry out the reaction at a temperature in the range of from $-70°$ C. to room temperature. The time required for the reaction may likewise vary widely, depending on many factors, notably the reaction temperature and the nature of the reagents. However, in most cases, a period of from 30 minutes to 3 hours will normally suffice.

After the reaction is complete, the desired compound can be recovered from the reaction mixture by conventional means. For example, one suitable recovery procedure comprises: filtering the reaction mixture if the mixture contains insoluble materials; pouring the mixture into ice-water; appropriately neutralizing the mixture, if necessary; extracting the mixture with a water-immiscible organic solvent; and finally removing the solvent by distillation, if necessary, under reduced pressure, to give the desired compound.

In the reaction in this step, depending on the nature of the protecting groups, it may be that one or more of the hydroxy-protecting groups is removed at the same time.

Step A5

Step A5 which is optional consists of anY one or more of the followinq reactions the removal of the hydroxy-protecting group included in the group represented by $R^{1a}$; oxidation of the hydroxymethyl group thus obtained to a formyl group, followed by further oxidation to a carboxy group, or direct oxidation to a carboxy group; esterification of the carboxy group thus obtained; conversion of the carboxy group or the ester group to an optionally substituted carbamoyl group; conversion of the ester to a free carboxylic acid; removal of the hydroxy-protecting group represented by $R^{2a}$ and/or $R^{3a}$; and conversion of the hydroxymethyl group to a hydroxymethylcarbonyl group (involving a protecting reaction of a hydroxy group). These reactions may be carried out in any appropriate order. Also, this step may also be carried out before or after Steps A3 and A4.

The removal of the hydroxy-protecting group is the same reaction as and may be carried out in the same way as described in the aforementioned Step A3.

The conversion of the hydroxymethyl group to a carboxy group can be carried out by conventional methods of oxidizing a primary alcohol into a carboxylic acid In this case, it is necessary that $R^{2a}$ and $R^{3a}$ should both be hydroxy-protecting groups.

The reaction may be carried out using an oxidizing agent, the nature of which is not critical, provided that it has no adverse effect on other parts of the molecule. Examples to suitable oxidizing agents include: chromic anhydride-concentrated sulfuric acid-water (Jones reagent), chromic anhydride, a mixture of potassium permanganate with sodium hydroxide or with sodium carbonate, silver oxide, or potassium bichromate-sulfuric acid.

The reaction is usually carried out in the presence of a solvent, the nature of which is not critical, provided that it has no adverse effect upon the reaction. Examples of suitable solvents include: ketones, such as acetone; water; a mixture of water with an alcohol such as methanol or ethanol; or a mixture of water with pyridine.

The reaction will take place over a wide range of temperatures, and the precise reaction temperature chosen is not critical to the invention. In general, we find it convenient to carry out the reaction at a temperature in the range of from $-30°$ C. to $100°$ C. The time required for the reaction may likewise vary widely, depending on many factors, notably the reaction temperature and the nature of the reagents However, in most cases, a period of from 30 minutes to 50 hours will normally suffice.

The same reaction may also be used to prepare a carboxy compound by oxidation of a formyl compound. The formyl compound may be prepared by oxidizing a hydroxymethyl compound in the same way as described above for Step A1.

After the reaction is complete, the desired carboxy compound can be recovered from the reaction mixture by conventional means. For example, one suitable recovery procedure comprises pouring the reaction mixture into ice-water; when the mixture is alkaline, acidifying it with a dilute acid; extracting it with a waterimmiscible organic solvent; and finally removing the solvent by distillation, if necessary, under reduced pressure, to give the desired compound.

The esterification of the carboxy group can be carried out by contacting the free carboxylic acid or a reactive derivative thereof with an esterifying agent in the presence or absence of a solvent. There is no particular restriction on the nature of the esterifying agent, provided that it has no adverse effect on other parts of the molecule. Examples of suitable esterifying agents include any of those commonly used for converting a carboxylic acid into an ester. For example, preferred esterifying agents include: diazoalkanes, such as diazomethane, diazoethane, diazopropane, diazoisopropane or diazobutane; ester-forming alcohols, such as methanol, ethanol, propanol, isopropanol, butanol, hexanol, decanol, cyclopentanol, cyclohexanol, benzyl alcohol or geraniol, employed in association with a mineral acid (such as hydrochloric acid, hydrobromic acid or sulfuric acid) or with an organic acid, preferably a sulfonic acid (such as methanesulfonic acid, benzenesulfonic acid or p-toluenesulfonic acid); or an alkyl halide such as methyl bromide, ethyl bromide or butyl bromide, employed in association with a base, such as sodium hydroxide, potassium hydroxide or sodium carbonate.

When a diazoalkane is employed the reaction is preferably carried out in the presence of a solvent. There is no particular restriction on the nature of the solvent, provided that it has no adverse effect on the reaction. Examples of suitable solvents include: ethers, such as diethyl ether or dioxane. The reaction will take place over a wide range of temperatures, and the precise reaction temperature chosen is not critical to the invention. In general, we find it convenient to carry out the reaction at a relatively low temperature in order to reduce side reactions and to avoid decomposition of the diazoalkane: the reaction is therefore preferably carried out under ice-cooling. The time required for the reaction may likewise vary widely, depending on many factors, notably the reaction temperature and the nature of the reagents. However, in most cases, a period of from 1 hour to 2 days will normally suffice.

When an alcohol is used in the presence of an acid, an excess of the alcohol is usually employed to serve simultaneously as the solvent and as a reagent. The reaction will take place over a wide range of temperatures, and the precise reaction temperature chosen is not critical to the invention. In general, we find it convenient to carry out the reaction at a temperature in the range of from room temperature to the boiling point of the alcohol employed. The time required for the reaction may likewise vary widely depending on many factors notably the reaction temperature and the nature of the reagents, especially the nature of the alcohol. However, in most cases, a period of from 1 hour to 2 days will normally suffice.

When a sodium salt of a carboxylic acid is treated in the conventional way with an halide, such as benzyl bromide. 4-methoxybenzyl chloride, methyl iodide. phenacyl bromide or benzhydryl chloride, in the presence of a base, such as triethylamine, pyridine or 4-(N,N-dimethylamino)- pyridine, the corresponding aralkyl, phenacyl or benzhydryl ester can also be prepared. The corresponding ester compound can also be prepared by first converting the carboxylic acid to a corresponding reactive derivative, such as an acyl halide or acid anhydride, using a halogenatinq agent, such as thionyl chloride or phosphorous pentachloride or an acyl halide, such as pivaloyl chloride or ethyl chloroformate, and by subsequently reacting the resulting reactive derivative with an optionally substituted phenol or the above-mentioned alcohol in an inert solvent. There is no particular restriction on the nature of the inert solvent, provided that it has no adverse effect on the reaction. Examples of suitable inert solvents include: ethers, such as diethyl ether; amides, such as dimethylformamide; and nitriles, such as acetonitrile. The reaction is preferably carried out in the presence of a base (for example, an organic amine such as triethylamine or 1,8-diazabicyclo[5.4.0]undec-7-ene).

The reaction will take place over a wide range of temperatures, and the precise reaction temperature chosen is not critical to the invention. In general, we find it convenient to carry out the reaction at about room temperature. The time required for the reaction may likewise vary widely, depending on many factors, notably the reaction temperature and the nature of the reagents. However, in most cases, a period of from 30 minutes to 3 hours will normally suffice.

After the reaction is complete, the desired ester compound can be recovered from the reaction mixture by conventional means. For example, one suitable recovery procedure comprises: removing the solvent from the reaction mixture, e.g. by distillation, if necessary under reduced pressure; if necessary, dissolving the residue in an organic solvent; washing the organic layer with an aqueous solution of an alkali metal carbonate or bicarbonate, such as sodium bicarbonate or sodium carbonate; drying the mixture; and removing the solvent by distillation, if necessary under reduced pressure, to give the desired compound.

The conversion of the acid or ester group into a carbamoyl group, which may be substituted, is carried out by reacting the acid with an amine compound in the presence of a mixed acid anhydride or of dicyclohexylcarbodiimide (DCC) or by reacting the ester with such an amino compound whilst heating.

The method using an mixed acid anhydride may be carried out, for example, by reacting the acid with an acyl halide (e.g. pivaloyl halide, tosyl halide, mesyl halide or oxalyl halide) or with an active ester, especially a chloroformate (e.g. ethyl chloroformate or isobutyl chloroformate) in the presence of a tertiary amine (e.g. pyridine, triethylamine, N,N-dimethylaminopyridine or picoline) and in an inert organic solvent the nature of which is not critical, provided that it has no adverse effect upon the reaction. Examples of suitable solvents include halogenated hydrocarbons, especially halogenated aliphatic hydrocarbons, such as chloroform or methylene chloride; and ethers, such as diethyl ether, tetrahydrofuran or dioxane. This reaction gives a mixed acid anhydride, which is then reacted with the amine compound, preferably in any of the above-mentioned inert organic solvents. The amine chosen will, of course, depend on the carbamoyl compound which it is desired to prepare. Examples of such amines include: ammonia; primary and secondary organic amines, such as methylamine, ethylamine, propylamine, isopropylamine, butylamine, aniline, 4-methylaniline, N,N-dimethylamine, methylethylamine, diethylamine, N-methylaniline, N-ethylaniline or 3,N-dimethylaniline; and amino acids and esters thereof, such as glycine, alanine, phenylalanine, serine or leucine.

The reaction will take place over a wide range of temperatures, and the precise reaction temperature chosen is not critical to the invention. In general, we find it convenient to carry out the reaction at a temperature in the range of from 0° C. to 100° C. The time required for the reaction may likewise vary widely depending on many factors, notably the reaction temperature and the nature of the reagents. However in mot cases, a period of from 1 hour to 24 hours will normally suffice.

The method using DCC is carried out by reacting the acid with the amine compound in the presence of DCC and in the presence or absence of one or more of the abovementioned tertiary amines and/or inert organic solvents, preferably at a temperature in the range from 0° C. to 100° C. These reactions are preferably carried out in an atmosphere of an inert gas, such as argon or nitrogen.

The conversion of the carboxy group into an N-acylcarbamoyl group may be carried out by contacting the free carboxylic acid or a reactive derivative thereof with an acyl isocyanate, such as acetyl isocyanate, trifluoroacetyl isocyanate or benzoyl isocyanate, in an inert solvent, the nature of which is not critical, provided that it has no adverse effect upon the reaction. Examples of suitable solvents include: hydrocarbons, especially aromatic hydrocarbons, such as benzene, toluene or xylene; and ethers, such as diethyl ether, tetrahydrofuran or dimethoxyethane.

The reaction will take place over a wide range of temperatures, and the precise reaction temperature chosen is not critical to the invention. In general, we find it convenient to carry out the reaction at about room temperature. The time required for the reaction may likewise vary widely, depending on many factors, notably the reaction temperature and the nature of the reagents. However, in most cases, a period of from 30 minutes to 10 hours will normally suffice.

The conversion of the carboxy group into an N-sulfonylcarbamoyl group may be carried out by first preparing a reactive ester derivative of the said carboxy group, which is subsequently reacted with a sulfonic acid amide. Such as methanesulfonamide, benzenesulfonamide or p-toluenesulfonamide in the presence of a solvent. The reactive ester derivative can be prepared by reacting the free carboxylic acid or a reactive derivative thereof with an N-hydroxyimide, such as N-hydroxysuccinimide or N-hydroxyphthalimide, in the presence of a condensing agent, such as dicyclohexylcarbodiimide, for a suitable period, e.g. from 30 minutes to 10 hours, and at a suitable temperature. e.g. around room temperature. The reaction of the reactive ester derivative with the sulfonic acid amide may be carried out for example at around room temperature for a suitable period, e.g. from 30 minutes to 15 hours, in the presence of a base, such as sodium methoxide, sodium ethoxide or potassium t-butoxide.

Both of the above reactions are preferably carried out in an inert solvent, the nature of which is not critical, provided that it has no adverse effect upon the reaction. Examples of suitable solvents include: hydrocarbons, especially aromatic hydrocarbons, such as benzene, toluene or xylene; ethers, such as diethyl ether, tetrahydrofuran or dimethoxyethane; amides, such as dimethylformamide or dimethylacetamide; and sulfoxides, such as dimethyl sulfoxide.

After the reaction is complete, the desired amide compound can be recovered from the reaction mixture by conventional means. For example, one suitable recovery procedure comprises: pouring the reaction mixture into ice-water; if necessary, neutralizing it; extracting it with a water-immiscible organic solvent; and finally removing the solvent from the extract. e.g. by distillation, if necessary, under reduced pressure, to give the desired compound. The product may, if required, be further purified by various conventional techniques such as recrystallization or the various chromatography techniques. e.g. silica gel chromatography.

The conversion of an ester group to a carboxy group is preferably carried out enzymatically. For example, the ester compound may be dissolved in a mixture of a water-miscible organic solvent, such as acetone, and a buffer such as a phosphoric acid buffer, after which an esterase is added to the mixture. The time and temperature required for the reaction will, of course, depend on the requirements of the esterase, but, in general, the reaction is usually carried out at around room temperature for a period of from 30 minutes to hours.

Conversion of the hydroxymethyl group to a hydroxymethylcarbonyl group may be carried out by the following sequence of reactions: the hydroxymethyl group is first oxidized to a formyl group in the same manner as described in Step A4; the formyl group is then reacted with an anion of a protected hydroxymethyl tin compound to give a 1,2-dihydroxyethyl group in which the 2-hydroxy group is protected; the product is then oxidized; and finally the protecting group is removed.

In this sequence of reactions, the carbonyl group of the compound of formula (VI) is preferably first protected. The protection is preferably effected by conversion of the carbonyl group to a group of formula:

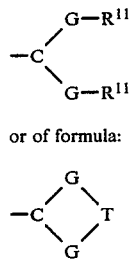

or of formula:

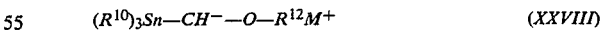

(in which $R^{11}$ represents a $C_1$–$C_4$ alkyl group, T represents a $C_2$–$C_5$ alkylene group, such as an ethylene, propylene, trimethylene, butylene, tetramethylene or 2,2-dimethyltrimethylene group, and G represents an oxygen atom or a sulfur atom). The protecting reaction and deprotecting reaction may be carried out by conventional methods.

The conversion of the formyl compound to a 1,2-dihydroxyethyl compound in which the 2-hydroxy group is protected may be carried out by reacting the formyl compound with an anion of formula (XXVIII):

$$(R^{10})_3Sn-CH^--O-R^{12}M^+ \qquad (XXVIII)$$

in which $R^{10}$ and M are as defined above, and $R^{12}$ represents a $C_2$–$C_4$ alkyl group having a 1-($C_1$–$C_4$ alkoxy) substituent, such as a 1-methoxyethyl or 1-ethoxyethyl group. The reaction preferably takes place in an inert solvent.

The compound of formula (XXVIII) can be prepared in the reaction mixture by a known method, as described, for example, in the Journal of the American Chemical Society, 100, 1481 (1978).

There is no particular restriction on the nature of the inert solvent used in this reaction, provided that it has no adverse effect on the reaction. Examples of suitable inert solvents include: ethers, such as diethyl ether, tetrahydrofuran or dimethoxyethane; and amides, such as hexamethylphosphoric triamide.

The reaction will take place over a wide range of temperatures, and the precise reaction temperature chosen is not critical to the invention. In general, we find it convenient to carry out the reaction at a temperature in the range of from $-78°$ C. to $0°$ C. The time required for the reaction may likewise vary widely, depending on many factors, notably the reaction temperature and the nature of the reagents. However, in most cases, a period of from 5 minutes to 2 hours will normally suffice.

The oxidation the 1,2-dihydroxyethyl compound in which the 2-hydroxy group is protected may be carried out in a conventional manner by treating the 1.2-dihydroxyethyl compound with the aforementioned Collins reagent, and the deprotection of the hydroxy group may be carried out by the same method as in the above-described deprotection reaction for the corresponding hydroxy group. When required, the deprotection of the carbonyl group may also be carried out.

The desired hydroxymethylcarbonyl compound can be recovered from the reaction mixture by conventional means. For example, one suitable recovery procedure comprises: pouring the reaction mixture into ice-water; neutralizing it appropriately; extracting it with a water-immiscible organic solvent; and finally removing the solvent from the extract, e.g. by distillation, if necessary under reduced pressure, to give the desired compound. The product may, if desired, be further purified by conventional techniques such as recrystallization or the various chromatography techniques, for example, column chromatography.

METHOD B

Method B is an alternative method of preparing a compound of formula (VIa), in which $R^{1a}$ is an optionally protected carboxy group ($R^{1b}$) and m is 2 or 3 (p) in the compound of formula (VI), after which the compound of formula (VIa) may be treated as described in Step A5.

Step B1

In Step B1 of Method B a compound of formula (VIII) is prepared by iodo-lactonization of a compound of formula (VII).

The reaction may be carried out by treating the compound of formula (VII) with a mixture of iodine and an alkali metal iodide (for example, sodium iodide or potassium iodide) in an inert solvent and in the presence of a base.

There is no particular restriction on the nature of the base, provided that it has no adverse effect on other parts of the molecule. Examples of suitable bases include: alkali metal carbonates and bicarbonates, such as sodium carbonate, sodium bicarbonate, potassium carbonate and potassium bicarbonate.

The nature of the inert solvent to be used is likewise not critical, and examples include: alcohols, such as methanol, ethanol or isopropanol; ethers, such as diethyl ether, tetrahydrofuran or dioxane; amides, such as dimethylformamide or dimethylacetamide; water; and mixtures of any two or more of these solvents.

The reaction will take place over a wide range of temperatures, and the precise reaction temperature chosen is not critical to the invention. In general, we find it convenient to carry out the reaction at a temperature in the range of from $0°$ C. to $50°$ C. The time required for the reaction may likewise vary widely, depending on many factors, notably the reaction temperature and the nature of the reagents. However, in most cases, a period of from 30 minutes to 5 hours will normally suffice.

After the reaction is complete, the desired compound produced in this step can be recovered from the reaction mixture by conventional means. For example, one suitable recovery procedure comprises: removing the solvent from the reaction mixture by distillation, if necessary under reduced pressure; adding ice-water to the residue; extracting the residue with a water-immiscible organic solvent; and finally removing the solvent by distillation, if necessary under reduced pressure, to give the desired compound.

Step B2

In step B2, a compound of formula (IX) is prepared by treating the compound of formula (VIII) with a reducing agent in an inert solvent There is no particular restriction on the nature of the reducing agent, provided that it has no adverse effect on other parts of the molecule. Examples of suitable reducing agents include any conventionally used for reducing an iodine atom to a hydrogen atom; the preferred reducing agent is a trialkyltin hydride (in which the alkyl group is a lower alkyl group, e.g. a $C_1$–$C_6$, preferably $C_1$–$C_4$, alkyl group), such as trimethyltin hydride or tributyltin hydride.

There is also no particular restriction on the nature of the inert solvent, provided that it has no adverse effect on the reaction. Examples of suitable inert solvents include; hydrocarbons, which may be aliphatic or aromatic, such as hexane, benzene or toluene; and ethers, such as diethyl ether or tetrahydrofuran.

This reaction can also preferably be carried out using a free radical reaction initiator, such as azobisisobutyronitrile or benzoyl peroxide, as a catalyst.

The reaction will take place over a wide range of temperatures, and the precise reaction temperature chosen is not critical to the invention. In general, we find it convenient to carry out the reaction at a temperature in the range of from $0°$ C. to $60°$ C. The time required for the reaction may likewise vary widely, depending on many factors, notably the reaction temperature and the nature of the reagents. However, in most cases, a period of from 10 minutes to 2 hours will normally suffice.

After the reaction is complete, the desired compound can be recovered from the reaction mixture by conventional means. For example, one suitable recovery procedure comprises: adding a dilute alkali solution, preferably a dilute aqueous alkali solution, to the reaction mixture; extracting the mixture with a water-immiscible organic solvent; and finally removing the solvent from the extract, e.g. by distillation, if necessary under reduced pressure, to give the desired compound.

Step B3

In Step B3, a compound of formula (X) is prepared by subjecting the compound of formula (IX) to hydrolysis or alcoholysis and, if required removing the protecting group $R^8$ from the hydroxy group.

The hydrolysis reaction may be carried out in the same manner as in the reaction conducted described above in Step A3 when the hydroxy-protecting group was an acyl group.

The alcoholysis reaction may be carried out in an inert solvent in the presence of a base by reacting the compound of formula (IX) with a compound of formula (XXIX):

$$R^{13}OH \qquad (XXIX)$$

(in which, $R^{13}$ represents a $C_1$–$C_{10}$ alkyl group, a $C_3$–$C_7$ cycloalkyl group, an aralkyl group, a phenacyl group or geranyl group).

There is no particular restriction on the nature of the base to be used, provided that it has no adverse effect on other parts of the molecule. Examples of suitable bases include: alkali metal hydroxides, such as sodium hydroxide or potassium hydroxide; alkali metal carbonates, such as sodium carbonate or potassium carbonate; and alkali metal alkoxides such as sodium methoxide or potassium t-butoxide.

There is also no particular restriction on the nature of the inert solvent provided that it has no adverse effect on the reaction. Examples of suitable inert solvents include: aromatic hydrocarbons such as benzene or toluene; and ethers, such as diethyl ether or tetrahydrofuran. Alternatively, the reaction may preferably proceed using a large excess of the alcohol of formula (XXIX) as the solvent as well as a reagent.

The reaction will take place over a wide range of temperatures, and the precise reaction temperature chosen is not critical to the invention. In general, we find it convenient to carry out the reaction at a temperature in the range of from 0° C. to 50° C. The time required for the reaction may likewise vary widely, depending on many factors, notably the reaction temperature and the nature of the reagents. However, in most cases, a period of from 1 to 24 hours will normally suffice.

After the reaction is complete, the desired compound produced in this step can be recovered by conventional means. For example, one suitable recovery procedure comprises: adding ice-water to the reaction mixture; extracting the mixture with a water-immiscible organic solvent; and finally removing the solvent from the extract, e.g. by distillation, if necessary under reduced pressure, to give the desired compound.

In the compound obtained in the above reaction, if the hydroxy-protecting group $R^8$ has not been removed, it can be removed by the same method as described in Step A3 of Method A. Also, when $R^{1b}$ represents a carboxy group, the hydroxy group, if required, can be protected by the method described later in Step C4 of Method C; esterification of the carboxy group may then be performed in a similar manner to that described in the aforementioned Step A5 of Method A, and the protecting group is finally removed from the hydroxy group by the method described in the aforementioned Step A3 of Method A. Moreover, after the carboxy group has been protected with a group such as a silyl group or the like followed by protecting the hydroxy groups and deprotecting the carboxy group, esterification of the carboxy group and deprotection of the hydroxy group may be performed to give the desired compound.

Step B4

In Step B4 a compound of formula (VIa) is prepared by oxidizing the compound of formula (X). This may be carried out by the same method as in the aforementioned Step A4 of Method A.

METHOD C

Method C is an alternative method of preparing the compound of formula (Xa) in which A represents a vinylene or ethynylene group ($A^1$) in the compound of formula (X).

Step C1

In Step C1 of Method C, a compound of formula (XII) is prepared by iodo-lactonization of a compound of formula (XI). This reaction can be carried out by the same method as described in the aforementioned Step B1 of Method B.

The starting compound of formula (XI) in Step C1 is a known compound or can be prepared without difficulty by a known method [for example, Ogawa et al., Tetrahedron Letters. 25, 1067 (1984)].

Step C2

In Step C2, a compound of formula (XIII) is prepared by reducing the compound of formula (XII). This reaction can be carried out by the same method as described in the aforementioned Step B2 of Method B.

Step C3

In Step C3, a compound of formula (XIV) is prepared by subjecting the compound of formula (XIII) to a hydrolysis or alcoholysis reaction. These reactions may be carried out by the same methods as described in the aforementioned Step B3 of Method B.

Step C4

In Step C4, a compound of formula (XV) is prepared by protecting a hydroxy group in the compound of formula (XIV).

The reaction for protecting this hydroxy group may be carried out in a conventional manner by contacting the compound of formula (XIV) with a compound which forms a protecting group. There is no particular limitation on the compound to be used for the protection, and examples include: carboxylic acids, such as acetic acid, propionic acid, butyric acid, benzoic acid or naphthalenecarboxylic acid and reactive derivatives thereof; aralkyl halides, such as benzyl chloride, benzyl bromide, 4-nitrobenzyl bromide or 4-methoxybenzyl bromide; trityl halides, such as trityl chloride or trityl bromide; 5- or 6-membered heterocyclic compounds, such as dihydropyran, dihydrothiopyran, dihydrothiophene or 4-methoxy-5,6-dihydro-(2H)-pyran; alkoxy-, alkylthio and aralkyloxy- substituted alkyl halides, such as methoxymethyl chloride, methylthiomethyl chloride, ethoxyethyl chloride or benzyloxymethyl chloride; unsaturated ethers, such as methyl vinyl ether or ethyl vinyl ether; and silyl compounds. Such as hexamethyldisilazane, trimethylsilyl chloride, tripropylsilyl chloride, t-butyldimethylsilyl chloride or diphenyl-t-butylsilyl chloride.

When a carboxylic acid compound is employed, the reaction is preferably carried out in the presence of a condensing agent such as dicyclohexylcarbodiimide.

Examples of suitable reactive derivatives of the carboxylic acid include, for example: acid halides, such as acetyl chloride, acetyl bromide, benzoyl chloride, benzoyl bromide or naphthoyl chloride and acid anhydrides. Such as acetic anhydride, propionic anhydride or benzoic anhydride. When such a reactive derivative is employed, the reaction is preferably carried out in the presence of an organic base, such as triethylamine, pyridine, 4-N,N-dimethylaminopyridine, quinoline or N,N-dimethylaniline.

The reaction is normally carried out in the presence of a solvent, the nature of which is not critical, provided that it has no adverse effect upon the reaction. Examples of suitable solvents include: hydrocarbons, which may be aliphatic or aromatic, such as benzene, toluene, xylene or hexane; halogenated hydrocarbons, particularly halogenated aliphatic or aromatic hydrocarbons, such as methylene chloride. chloroform, carbon tetrachloride or chlorobenzene; ethers, such as diethyl ether, tetrahydrofuran or dioxane; and ketones, such as acetone or methyl ethyl ketone. The hydrocarbons are preferred.

The reaction will take place over a wide range of temperatures, and the precise reaction temperature chosen is not critical to the invention. In general, we find it convenient to carry out the reaction at a temperature in the range of from 0° C. to 100° C. The time required for the reaction may likewise vary widely, depending on many factors, notably the reaction temperature and the nature of the reagents and reaction solvents However, in most cases, a period of from 30 minutes to 6 hours will normally suffice.

When an aralkyl halide, a trityl halide, an alkoxy-, alkylthio-or aralkyloxy-substituted aralkyl halide, or a silyl compound is employed, the compound of formula (XIV) is first converted into an alkali metal salt by reacting it with an alkali metal hydride, such as sodium hydride or potassium hydride, and the salt thus prepared is then reacted with the corresponding halide or silyl compound (such as disilazane) in an inert solvent to give the desired compound.

There is no particular restriction on the nature of the solvent to be employed, provided that it has no adverse effect on the reaction. Examples of suitable solvents include: ethers, such as diethyl ether, tetrahydrofuran or dioxane; amides, such as dimethylformamide, dimethylacetamide or hexamethylphosphoric triamide: nitriles such as acetonitrile or benzonitrile; and sulfoxides, such as dimethyl sulfoxide. However, of these, the amides are preferred.

The reaction will take place over a wide range of temperatures, and the precise reaction temperature chosen is not critical to the invention. In general, we find it convenient to carry out the reaction at a temperature in the range of from 0° C. to 100° C. The time required for the reaction may likewise vary widely, depending on many factors, notably the reaction temperature and the nature of the reagents However, in most cases, a period of from 10 minutes to 3 hours will normally suffice.

The compound of formula (XIV) may be also reacted with the corresponding halide compound in the presence of an organic base, such as triethylamine, pyridine. 4-N,N-dimethylaminopyridine or imidazole, or of an inorganic base, such as sodium hydroxide, potassium hydroxide or potassium carbonate.

When a 5-and 6-membered heterocyclic compound or an unsaturated ether compound is employed, the reaction may be carried out in the presence or absence of an inert solvent using a small amount of an acid such as, for example, a mineral acid (e.g. hydrochloric acid or hydrobromic acid) or an organic acid (e.g. picric acid. trifluoroacetic acid, benzenesulfonic acid, p-toluenesulfonic acid or camphorsulfonic acid).

There is no particular restriction on the nature of the solvent to be employed, provided that it has no adverse effect on the reaction. Examples of suitable solvents include: ethers, such as diethyl ether tetrahydrofuran or dioxane: halogenated hydrocarbons, particularly halogenated aliphatic hydrocarbons, such as methylene chloride, chloroform or carbon tetrachloride; and aromatic hydrocarbons, such as benzene, toluene or xylene. However, of these, the halogenated hydrocarbons are preferred.

The reaction may be carried out in the absence of an inert solvent by using an excess of the heterocyclic compound or of the vinyl ether compound, which then serves as the solvent as well as as a reagent.

The reaction will take place over a wide range of temperatures, and the precise reaction temperature chosen is not critical to the invention. In general, we find it convenient to carry out the reaction at a temperature in the range of from 0° C. to 50° C. The time required for the reaction may likewise vary widely, depending on many factors, notably the reaction temperature and the nature of the reagents. However, in most cases, a period of from 30 minutes to 3 hours will normally suffice.

After each of the above reactions is complete, the desired compound in which the hydroxy group is protected can be recovered from the reaction mixture by conventional means. For example, one suitable recovery procedure comprises: pouring the reaction mixture into ice-water; when insoluble materials are present, filtering the mixture to remove them; neutralizing the mixture appropriately when it is acidic or alkaline; extracting it with a water-immiscible organic solvent; and finally removing the solvent by distillation, if necessary under reduced pressure, to give the desired compound. The product may, if required, b ⓇFurther purified by such conventional techniques as recrystallization or the various chromatography techniques, such as, for example, column chromatography or thin layer chromatography.

When $R^{1b}$ represents a carboxy group, esterification may be carried out according to the method described in the aforementioned Step A5 of Method A.

Step C5

In Step C5, a compound of formula (XVI) is prepared by removing the protecting group $R^9$ from the compound of formula (XV). This reaction can be carried out by the same method as described in the aforementioned Step A3 of Method A.

In the present step removal of the group $R^9$ may be achieved selectively by appropriate selection of the protecting groups $R^8$ and $R^{2a}$ used to protect the other hydroxy groups. In such a case, $R^{2a}$, $R^8$ and $R^9$ should be groups which are removable under acidic, basic and neutral conditions, respectively. An example of such a combination is a compound where: $R^8$ represents a group such as an acyl group, which can be removed under basic conditions; $R^{2a}$ represents a group such as a heterocyclic group, a substituted methyl group, a 1-alkoxyethyl group or a trityl group, which can be removed under acidic conditions, and $R^9$ represents a group such as a tri-substituted silyl group (e.g. dimethyl-t-butylsilyl, diphenyl-t-butylsilyl or the like) or an aralkyl group. which can be removed under neutral conditions.

Step C6

In Step C6, a compound of formula (XVII) is prepared by removing the protecting group $R^9$ from the compound of formula (XIII). This reaction can be carried out by the same method as described in the aforementioned Step A3 of Method A.

Step C7

In Step C7, a compound of formula (XVIII) is prepared by oxidizing the compound of formula (XVII). This reaction may be carried out by the same method as described in the aforementioned Step B4 of Method B.

Step C8

In Step C8, a compound of formula (XIX) is prepared by oxidizing the compound of formula (XVI). This reaction may be carried out by the same method as described in the aforementioned Step B4 of Method B.

Step C9

In Step C9, a compound of formula (XX) is prepared by reacting the compound of formula (XVIII) with a Wittig reagent of formula (XXX):

or a modified Wittig reagent of formula (XXXI):

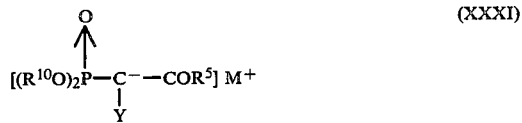

(in which $R^5$, $R^{10}$, M and y are as defined above). This reaction may be carried out by the same method as described in the aforementioned Step A1 of Method A.

Step C10

In Step C10, a compound of formula (XXI) is prepared by reacting the compound of formula (XIX) with a Wittig reagent or modified Wittig reagent of formula (XXX) or (XXXI). This reaction may be carried out by the same method as described in the aforementioned Step C9 of Method C.

Step C11

In Step C11, a compound of formula (XXI) is prepared by subjecting the compound of formula (XX) to hydrolysis or alcoholysis, followed by protecting the hydroxy group. This Step can be carried out by the same methods as described in the aforementioned Steps C3 and C4 of Method C.

Step C12

In Step C12, a compound of formula (XXII) is prepared by treating the compound of formula (XX) with a reducing agent or with a Grignard compound of formula (XXXII):

$$R^{4a}-Mg-X \qquad (XXXII)$$

(in which X is as defined above, and $R^{4a}$ represents a $C_1$-$C_4$ alkyl group). The reaction with the reducing agent is usually carried out in an inert solvent.

There is no particular restriction on the nature of the reducing agent, provided that it has no adverse effect on other parts of the molecule, and any reducing agent commonly used for converting a carbonyl group to a hydroxy group without affecting other parts of the molecule may equally be used in this reaction. Examples of suitable reducing agents include: metal hydride compounds, such as sodium borohydride, potassium borohydride, lithium borohydride, zinc borohydride, lithium tri-t-butoxyaluminum hydride, lithium trimethoxyaluminum hydride or sodium cyanoborohydrIde; and aluminum compounds, such as aluminum isopcopoxide or diisobutyl-(2,6-di-t-butyl-4-methylphenoxy)aluminum. However, of these, sodium borohydride is preferred. In order to suppress the reduction of the double bond' cerium chloride or the like may be added to the reaction mixture.

There is likewise no particular restriction on the nature of the inert solvent, provided that it has no adverse effect on the reaction, and any solvent commonly used in reactions with a reducing agent may equally be used here. Examples of suitable inert solvents include: alcohols, such as methanol, ethanol, propanol, butanol or t-butanol; ethers, such as diethyl ether, tetrahydrofuran or dioxane; and mixtures of any two or more of these solvents. In the reaction with a reducing agent an alcohol is preferably used, methanol being more preferred, and, in the reaction with the compound of formula (XXXII), an ether is preferably employed.

The reaction will take place over a wide range of temperatures, and the precise reaction temperature chosen is not critical to the invention. In general, we find it convenient to carry out the reaction at a temperature in the range of from 0° C. to room temperature. The time required for the reaction may likewise vary widely, depending on many factors, notably the reaction temperature and the nature of the reagents. However, in most cases, a period of from lo minutes to 2 hours will normally suffice.

After the reaction is complete, the desired compound produced in the present step can be recovered from the reaction mixture by conventional means. For example, one suitable recovery procedure comprises: removing the solvent by distillation, if necessary under reduced pressure, from the reaction mixture; adding ice-water to the residue; extracting the mixture with a water-immiscible organic solvent: and finally removing the solvent by distillation, if necessary under reduced pressure, from the extract to give the desired compound.

Step C13

In Step C13, a compound of formula (XXIII) is prepared by treating the compound of formula (XXI) with a reducing agent or with a Grignard compound of formula (XXXII), as shown in Step C12. This step can be carried out by the same method as described in the aforementioned Step C12 of Method C.

Step C14

In Step C14, a compound of formula (XXIII) is prepared by subjecting the compound of formula (XXII) to a hydrolysis or alcoholysis reaction and then protecting the hydroxy group. This step can be carried out by the same method as described in the aforementioned Steps C3 and C1 of Method C.

Step C15

In Step C15, a compound of formula (XXIV) is prepared by protecting the hydroxy group of the corresponding compound of formula (XXII). When y represents a halogen atom, the halovinylene group may, if desired, be converted into an ethynylene group before protecting the hydroxy group.

The reaction for converting the halovinylene group into an ethynyl group, which is an optional step may be carried out by treating the corresponding compound of formula (XXII) with a base in an inert solvent. There is no particular restriction on the nature of the base, provided that it has no adverse effect on other parts of the molecule. Examples of suitable bases include: alkali metal alkoxides, such as sodium methoxide, potassium ethoxide, potassium t-butoxide or sodium t-pentoxide; and alkali metal hydroxides, such as sodium hydroxide or potassium hydroxide. However, we preferably use a strong base, such as potassium t-butoxide sodium t-pentoxide or potassium hydroxide.

There is likewise no particular restriction on the nature of the solvent, provided that it has no adverse effect on the reaction. Examples of suitable solvents include: alcohols, such as methanol, ethanol or t-butanol; and ethers, such as diethyl ether or tetrahydrofuran.

The reaction will take place over a wide range of temperatures, and the precise reaction temperature chosen is not critical to the invention. In general, we find it convenient to carry out the reaction at a temperature in the range of from room temperature to the boiling point of the solvent employed. The time required for the reaction may likewise vary widely, depending on many factors, notably the reaction temperature and the nature of the reagents. However, in most cases, a period of from 30 minutes to 5 hours will normally suffice.

After the reaction is complete, the desired compound can be recovered from the reaction mixture by conventional means. For example, one suitable recovery procedure comprises: if required, removing the solvent by distillation, if necessary under reduced pressure, from the reaction mixture; pouring the reaction mixture into ice-water; if required, neutralizing the mixture; extracting it with a suitable organic solvent; washing the extract with water; drying it; and finally removing the solvent by distillation, if necessary under reduced pressure, to give the desired compound. The product may, if required, be further purified by such conventional techniques as the various chromatography techniques, notably silica gel chromatography.

The protection of the hydroxy group can be carried out by the same method as described in the aforementioned Step C4 of method C.

When $R^{1b}$ represents a carboxy group, the group can be protected by esterification using a reaction corresponding to that in the aforementioned Step A5 of Method A, and, when $R^{1b}$ represents a protected carboxy group, the protecting group may first be removed by hydrolysis or the like reaction and the group may be protected with another protecting group by esterification.

Step C16

In Step C16, compound of formula (XXV) is prepared by protecting the hydroxy group of the corresponding compound of formula (XXIII). When Y represents a halogen atom, the halovinylene group may, if desired, be converted into an ethynylene group before protecting the hydroxy group. This step can be carried out by the same method as described in the aforementioned Step C15 of Method C.

Step C17

In Step C17, a compound of formula (XXV) is prepared by subjecting the compound of formula (XXIV) to hydrolysis or alcoholysis and protecting the hydroxy group. This step can be carried out by the same method as described in the aforementioned Steps C3 and C4 of Method C.

Step C18

In Step C18, compound of formula (Xa) is prepared by removing the hydroxy-protecting group $R^8$ from the compound of formula (XXIV) and subjecting the deprotected compound of formula (XXIV) to hydrolysis or alcoholysis. Alternatively, the removal of the hydroxy-protecting group $R^8$ and the hydrolysis or alcoholysis reaction may be carried out simultaneously. This step can be carried out by the same methods as described in the aforementioned Step A3 of Method A and/or Step C3 of Method C.

Step C19

In Step C19, compound of formula (Xa) is prepared by removing the hydroxy-protecting group $R^8$ from the compound of formula (XXV). This reaction may be carried out by the same method as described in the aforementioned Step A3 of Method A.

When the desired compounds prepared by these methods are obtained as a mixture of various kinds of geometrical and optical isomers, the iSomers can be separated and resolved in an appropriate synthetic step as is well known in the art. Alternatively, stereospecific synthesis steps may be employed to prepare the individual isomers directly.

The compounds of the present invention have surprisingly been found to possess an excellent anti-ulcer effect associated with a weak or very weak inhibitory effect against platelet aggregation. The compounds of the present invention are thus extremely useful for both the therapy and the prophylaxis of ulcers. The compounds may be administered orally or parenterally, and the formulation used will depend on the route of administration. For example, for oral administration, the compounds of the present invention may be formulated as tablets, capsules, granules. powders, syrups or fatty emulsions (liposome preparations). For intravenous injections, they may be formulated with appropriate injectible media. The dose will depend upon the route of administration, as well as upon the symptoms, age and body weight of the patient, but the preferred dose for an adult human would normally be from 0.0001 mg to 100 mg, more preferably from 0.001 mg to 10 mg, per day, which may be administered in a single dose or in divided doses.

The preparation of various compounds of the present invention is illustrated by the following non-limiting Examples. M&C FOLIO: 55539/FP-8801 WANG-DOC: 0864H

EXAMPLE 1

5-Oxo-16-phenoxy-17,18,19,20-tetranorprostaglandin $E_1$ methyl ester

1(a)

α-Hydroxy-2α-[6-carboxy-2(Z)-hexenyl]-3β-(dimethyl-t-butylsilyloxymethyl)-4α-(2-tetrahydropyranyloxy)cyclopentane A mixture of 500 ml of a methanolic solution containing 10.0 g of 1α-hydroxy-2α-[6-methoxycarbonyl-2(Z)-hexenyl]-3β-dimethyl-t-butylsilyloxymethyl 4α-(tetrahydropyran-2-yloxy)cyclopentane and 250 ml of a 5% v/v aqueous solution of sodium hydroxide was stirred at room temperature for 1.5 hours. At the end of this time the reaction mixture was neutralized. whilst cooling, by the addition of concentrated hydrochloric acid, and the solvent was removed by distillation under reduced pressure. Ice-water was added to the residue, after which it was weakly acidified by the addition of concentrated hydrochloric acid and extracted with ethyl acetate. The extract was washed with a saturated aqueous solution of sodium chloride and dried over anhydrous sodium sulfate. The solvent was then removed by distillation under reduced pressure, to give 8.67 g of the title compound as an oily substance.

Infrared Absorption Spectrum (liquid film) $v_{max}$ cm$^{-1}$: 3450, 1708, 1030.

Nuclear Magnetic Resonance Spectrum (CDCl$_3$), δppm:
 0.89 (9H, singlet):
 4.70 (1H, broad singlet);
 5 45 (2H, multiplet).

1(b)

1α-Acetoxy-2α-[6-carboxy-2(Z)-hexenyl]-3β-(dimethyl-t-butylsilyloxymethyl)-4α-(2-tetrahydropyranyloxy)cyclopentane 10 ml of acetic anhydride were added to 20 ml of a pyridine solution containing 8.64 g of 1α-hydroxy 2α-[6 carboxy 2(Z)-hexenyl]-3β-(dimethyl-t-butylsilyloxymethyl)-4α-(2-tetrahydropyranyloxy)cyclopentane [prepared as described in Example 1(a)], a catalytic amount of 4-dimethylaminopyridine was then added to the resulting mixture, and the mixture was allowed to stand at 0° C. for 100 hours. At the end of this time, 10 ml of water were added to the reaction mixture, and the mixture was stirred at room temperature for 30 minutes. It was then poured onto ice-water, acidified with 3% w/v aqueous hydrochloric acid, and then extracted with ethyl acetate. The extract was washed with a saturated aqueous solution of sodium chloride and dried over anhydrous sodium sulfate; the solvent was then removed by distillation under reduced pressure The residue was purified by silica gel column chromatography, to give 8.23 g of the title compound as an oily substance from those fractions eluted by hexane containing ethyl acetate in proportions ranging from 20-45% by volume Infrared Absorption Spectrum (liquid film) $v_{max}$ cm$^{-1}$: 1742, 1718, 1252, 1022.

Nuclear Magnetic Resonance Spectrum (CDCl$_3$), δppm:
 0.90 (9H, singlet);
 2.02 (3H, singlet);
 4.65 (1H, broad singlet):
 5.08 (1H, multiplet):
 5.45 (2H, multiplet).

1(c)

1α-Acetoxy-2α-[2-iodo-2-(6-oxotetrahydropyran-2-yl)ethyl]-3β-(dimethyl-t-butylsilyloxymethyl)-4α-(tetrahydropyran-2-yloxy)cyclopentane 47.6 ml of a 0.5N aqueous solution of sodium bicarbonate were added at room temperature to 47.6 ml of an isopropanol solution containing 7.21 g of 1α-acetoxy 2α-[6-carboxy-2(Z)-hexenyl]3β(dimethyl-t-butylsilyloxymethyl)-4α-(2-tetrahydropyranyloxy)cyclopentane [prepared as described in Example 1 (b)], and the mixture was stirred for 10 minutes. At the end of this time, a solution of iodine and potassium iodide (prepared by dissolving 11.01 g of iodine and 21.60 g of potassium iodide in 65.0 ml of water) was added to the mixture, and the mixture was stirred at 30-38° C. for 2 hours. The reaction mixture was then poured onto 700 ml of a 10% w/v aqueous solution of sodium thiosulfate, and extracted with ethyl acetate. The extract was washed with a saturated aqueous solution of sodium chloride and dried over anhydrous sodium sulfate, and the solvent was removed by distillation under reduced pressure, to give 8.97 g of the title compound as an oily mixture of two isomers Infrared Absorption Spectrum (liquid film) $v_{max}$ cm$^{-1}$: 1740, 1242, 1022.

Nuclear Magnetic Resonance Spectrum (CDCl$_3$), δppm:
 0.91 (9H, singlet);
 2.09 (3H, singlet);
 4.60 (1H, broad singlet);
 5.18 (1H, multiplet).

1(d)

1α-Acetoxy-2α-[2-(6-oxotetrahydrooyran-2-yl)ethyl]-3β-(dimethyl-t-butylsilyloxymethyl)-4-α(tetrahydropyran-2-yloxy)cyclopentane 5.70 ml of tributyltin hydride and a catalytic amount of α,α'-azobisisobutyronitrile were added to 180 ml of a benzene solution containing 8.94 g of 1α-acetoxy 2α-(2-iodo 2-(6-oxotetrahydropyran-2-yl)ethyl]-3β-(dimethyl-t-butylsilyloxymethyl)-4α-(tetrahydropyran-2-yloxy)cyclopentane [prepared as described in Example 1(c)], and the mixture was then warmed to 40° C. and stirred for 20 minutes. At the end of this time, the reaction mixture was diluted with a saturated aqueous solution of sodium bicarbonate, and extracted with ethyl acetate. The extract was washed with a saturated aqueous solution of sodium chloride and dried over anhydrous sodium sulfate, and the solvent was then removed by distillation under reduced pressure. The residue was purified by silica gel column chromatography, to give 5.83 g of the title compound as an oily substance from the fractions eluted with hexane containing ethyl acetate in proportions ranging from 25-35% by volume.

Infrared Absorption Spectrum (liquid film) δmax cm$^{-1}$:
 1740, 1250, 1024.

Nuclear Magnetic Resonance Spectrum (CDCl$_3$), δppm:
 0.90 (9H, singlet);
 4.62 (1H, broad singlet);
 5.15 (1H, multiplet).

1(e)
1α-Hydroxy-2α-(3-hydroxy-6-methoxycarbonylhexyl)-3β-(dimethyl-t-butylsilyloxymethyl)-4α-(tetrahydropyran-2-yloxy)cyclopentane 3.80 g of anhydrous potassium carbonate were added to 200 ml of a methanolic solution containing 6.67 g of 1α-acetoxy-2α-[2-(6-oxotetrahydropyran-2-yl)ethyl]3β-(dimethyl-t-butylsilyloxymethyl)-4α-(tetrahydropyran-2-yloxy)cyclopentane [prepared as described in Example 1(d)], and the mixture was then stirred at room temperature for 20 hours. At the end of this time the reaction mixture was poured onto ice-water acidified with hydrochloric acid and extracted with ethyl acetate. The extract was washed with a saturated aqueous solution of sodium chloride, and then the solvent was removed by distillation under reduced pressure. The residue was dissolved in diethyl ether and the resulting partially hydrolyzed product was esterified with diazomethane. The solvent was then removed by evaporation under reduced pressure, and the residue was purified by silica gel column chromatography. Those fractions eluted with hexane containing ethyl acetate in proportions ranging from 45–90% by volume afforded 5.15 g of the title compound as an oily mixture of two isomers.

Infrared Absorption Spectrum (liquid film) $\delta_{max}$ cm$^{-1}$: 3450, 1746, 1258, 1022.

Nuclear Magnetic Resonance Spectrum (CDCl$_3$). $\delta$ ppm:
 0.90 (9H, singlet);
 3.68 (3H, singlet);
 4.70 (1H, broad singlet).

1(f)
1α-Acetoxy-2α-(3-acetoxy-6-methoxycarbonylhexyl)-3β-(dimethyl-t-butylsilyloxymethyl)-4α-(tetrahydropyran-2-yloxy)cyclopentane 12 ml of acetic anhydride were added to 12 ml of a pyridine solution containing 5.14 g of 1α-hydroxy 2α-(3-hydroxy-6-methoxycarbonylhexyl)-3β-(dimethyl t-butylsilyloxymethyl) 4α-(tetrahydropyran-2-yloxy) cyclopentane [prepared as described in Example 1(e)]. and the mixture was allowed to stand at room temperature for 7 hours and then at 0° C. for 15 hours. At the end of this time, water and ice-cooled aqueous hydrochloric acid were added, in that order, to the reaction mixture, and the mixture was extracted with ethyl acetate. The extract was washed with a saturated aqueous solution of sodium chloride and dried over anhydrous sodium sulfate, and then the solvent was removed by distillation under reduced pressure, to give a residue, which was purified by silica gel column chromatography. 5.49 g of the title compound were obtained as an oily substance from those fractions eluted with hexane containing ethyl acetate in proportions ranging from 18–26% by volume.

Infrared Absorption Spectrum (liquid film) $\delta$ cm$^{-1}$: 1742, 1248, 1020.

Nuclear Magnetic Resonance Spectrum (CDCl$_3$) $\delta$ ppm:
 0.90 (9H, singlet);
 2.04 (6H, singlet);
 3.68 (3H, singlet);
 4.62 (1H, broad singlet);
 4.85 (1H, multiplet);
 5.10 (1H, multiplet).

1(g)
1α-Acetoxy-2α-(3-acetoxy-6-methoxycarbonyl hexyl)-3β-hydroxymethyl-4α-(tetrahydropyran-2-yloxy)cyclopentane 23.9 ml of a 1 M tetrahydrofuran solution of tetrabutylammonium fluoride were added to 110 ml of a tetrahydrofuran solution containing 5.47 g of 1α-acetoxy-2α-(3-acetoxy-6 methoxycarbonylhexyl) 3β-(dimethyl t-butylsilyloxymethyl)-4ζ (tetrahydropyran-2-yloxy)cyclopentane [prepared as described in Example 1(f)], and the mixture was stirred at room temperature for 3 hours. At the end of this time, the reaction mixture was poured onto a saturated aqueous solution of sodium chloride and extracted with ethyl acetate. The extract was washed with a saturated aqueous solution of sodium chloride and dried over anhydrous sodium sulfate, and the solvent was removed by distillation under reduced pressure. The residue was purified by silica gel column chromatography, to give 4.29 g of the title compound as an oily substance from those fractions eluted with hexane containing ethyl acetate in proportions ranging from 50–80% by volume.

Infrared Absorption Spectrum (liquid film) $\delta_{max}$ cm$^{-1}$: 3450, 1732, 1374, 1240, 1018.

Nuclear Magnetic Resonance Spectrum (CDCl$_3$), $\delta$ ppm:
 2.06 (6H, singlet);
 3.68 (3H, singlet);
 4.4–5.0 (2H, multiplet);
 5.10 (1H, multiplet).

1(h)
1α-Acetoxy-2α-(3-acetoxy-6-methoxycarbonylhexyl)-3β-formyl-4α-(tetrahydropyran-2-yloxy)cyclopentane 6.1 ml of triethylamine were added to a solution of 1.0 g of 1α-acetoxy 2-(3-acetoxy-6-methoxycarbonylhexyl)-3β-hydroxymethyl-4α-(tetrahydropyran 2-yloxy)-cyclopentane [prepared as described in Example 1(g)]in 10 ml of dimethyl sulfoxide, and then 5 ml of a dimethyl sulfoxide solution containing 7.4 g of a pyridine sulfuric anhydride complex were added thereto at room temperature. The mixture was stirred for 20 minutes at room temperature, after which it was poured onto ice water and extracted with ethyl acetate. The extract was washed with a saturated aqueous solution of sodium chloride, with 2% w/v aqueous hydrochloric acid containing ice and with a saturated aqueous solution of sodium chloride, in that order, and dried over anhydrous sodium sulfate. The solvent was then removed by distillation under reduced pressure, to give 1.03 g of the crude title compound as an oily substance.

Infrared Absorption Spectrum (liquid film) $\delta_{max}$ cm$^{-1}$: 2700, 1730, 1240, 1020 cm$^{-1}$ Nuclear Magnetic Resonance Spectrum (CDCl$_3$), $\delta$ ppm:
 2.03 (3H, singlet);
 2.07 (3H, singlet);
 3.68 (3H, singlet);
 5.15 (1H, multiplet);
 9.82 (1H, multiplet).

1(i) Methyl
5,9α-diacetoxy-11α-(tetrahydropyran-2-yloxy)-15-oxo-16-phenoxy-17,18,19,20-tetranorprost-13(E)-enoate 0.29 g of sodium hydride (as a 55% w/w dispersion in mineral oil, and which had been washed with hexane) was suspended in 45 ml of tetrahydrofuran, and 2.54 g of dimethyl 2-oxo-3-phenoxypropylphosphonate was added to the resulting suspension, whilst ice-cooling; the mixture was then stirred at room temperature for 1 hour. At the end of this time, 15 ml of a tetrahydrofuran solution containing 1.34 g of 1α-acetoxy-2α-(3-acetoxy-6-methoxycarbonylhexyl)3β-formyl-4α-(tetrahydropyran-2-yloxy)cyclopentane [prepared as described in Example 1(h)] was added, whilst ice-cooling, and the mixture was heated under reflux for 2 hours. The reaction mixture was then cooled, diluted with ice-water, acidified with concentrated hydrochloric acid, and extracted with ethyl acetate. The extract was washed with a saturated aqueous solution of sodium chloride and dried over anhydrous sodium sulfate, and the solvent was then removed by distillation under reduced pressure The residue was purified by silica gel column chromatography, to give 1.35 g of the title compound as an oily substance from those fractions eluted with hexane containing ethyl acetate in proportions ranging from 30–40% by volume.

Infrared Absorption Spectrum (liquid film) $\delta_{max}$ cm$^{-1}$:
1738, 1696, 1624, 1602, 1592, 1242.

Nuclear Magnetic Resonance Spectrum (CDCl$_3$), δ ppm:
2.00 (3H, singlet);
2.07 (3H, singlet);
3.67 (3H, singlet);
4.3–5.3 (5H, multiplet).
6.3–7.5 (7H, multiplet).

1(j) Methyl 5,9α-diacetoxy-11α-(tetrahydropyran2-yloxy)-15αhydroxy-16-phenoxy-17,18,19,20-tetranorprost-13(E)-enoate and its 15β-isomer 12.0 ml of a methanolic solution containing 1.33 q methyl 5.9α-diacetoxy 11c-(tetrahydropyran 2yloxy) 15-oxo-16-phenoxy-17,18,19,20-tetranorprost 13(E)enoate [prepared as described in Example 1(i)]. followed by 85 mg of sodium borohydride, were added, whilst ice-cooling, to 8 ml of a methanolic solution containing 850 mg of cerium chloride heptahydrate at an internal temperature of 5° C. to 1° C. and the mixture was stirred at that temperature for 15 minutes. At the end of this time, the reaction mixture was diluted with ice-water and extracted with ethyl acetate. The extract was washed with water and dried over anhydrous sodium sulfate, and the solvent was removed by distillation under reduced pressure. The residue was purified by silica gel column chromatography to give 520 mg of the 15β-isomer as a substance of low polarity, and 420 mg of the 15α-isomer as a substance of higher polarity.

15α-isomer:

Infrared Absorption Spectrum (liquid film) $\delta_{max}$ cm$^{-1}$: 3460, 1734, 1600, 1588, 1242.

Nuclear Magnetic Resonance Spectrum (CDCl$_3$) δ ppm:
2.00 (3H, singlet);
2.06 (3H, singlet);
3.67 (3H, singlet);
5.12 (1H, multiplet);
5.72 (2H, multiplet);
6.8–7.5 (5H, multiplet).

15β-isomer

Infrared Absorption Spectrum (liquid film) $\nu_{max}$ cm$^{-1}$: 3460, 1736, 1602, 1588, 1242.

Nuclear Magnetic Resonance Spectrum (CDCl$_3$) δ ppm:
2.01 (3H, singlet):
2.05 (3H, singlet):
3.68 (3H, singlet):
13 (1H, multiplet):
63 (2H, multiplet):
6.8 7.5 (1H, multiplet).

1(k) Methyl 5,9α-diacetoxy-11α,15α-di(tetrahydropyran-2-yloxy)-16 phenoxy-17,18,19,20-tetranorprost-13(E)-enoate 0.1 ml of dihydropyran and a catalytic amount of p-toluenesulfonic acid were added to 2 ml of a methylene chloride solution containing 400 mg of methyl 5.9α-diacetoxy,11α-(tetrahydropyran-2 yloxy)15α-hydroxy-16-phenoxy-17,18,19,20tetranorprost-13(E)-enoate [prepared as described in Example 1(j)], and the mixture was allowed to stand at room temperature for 20 minutes. At the end of this time, ethyl acetate was added to the reaction mixture and the mixture was washed with water. The resulting solution was dried over anhydrous sodium sulfate, and the solvent was removed by evaporation under reduced pressure, to give 0.48 g of the title compound as an oily substance.

Infrared Absorption Spectrum (liquid film) $\nu_{max}$ cm$^{-1}$: 1738, 1600, 1588, 1242, 1033.

Nuclear Magnetic Resonance Spectrum (CDCl$_3$), δ ppm:
1.95, 1.97 (3H, 2 peaks);
2.03 (3H, singlet)
3.65 (3H, singlet);
5.15 (1H, multiplet);
5.65 (2H, multiplet);
6.8–7.5 (5H, multiplet).

1(l) Methyl 5,9α-dihydroxy-11α,15α-di(tetrahydropyran-2-yloxy)-16-phenoxy-17 18,19,20-tetranorprost13(E)-enoate 190 mg of anhydrous potassium carbonate were added to 9.2 ml of a methanolic solution containing 460 mg of methyl 5.9α-diacetoxy-11α,15α-di(tetrahydropyran-2-yloxy) 16-phenoxy-17,18,19,20-tetranorprost-13(E) enoate [prepared as described in Example 1(k)], and the mixture was warmed to 40° C., whilst stirring. After 2 hours at this temperature, the reaction mixture was diluted with ice-water, neutralized by the addition of concentrated hydrochloric acid and extracted with ethyl acetate. The extract was washed with a saturated aqueous solution of sodium chloride and dried over anhydrous sodium sulfate, and the solvent was then removed by distillation under reduced pressure. The residue was purified by silica gel column chromatography, to give 337 mg of the title compound as an oily substance from those fractions eluted with hexane containing ethyl acetate in proportions ranging from 60–90% by volume.

Infrared Absorption Spectrum (liquid film) $\nu_{max}$ cm$^{-1}$: 3450, 1738, 1600, 1588, 1018.

Nuclear Magnetic Resonance Spectrum (CDCl$_3$), δ ppm:
3.66 (3H, singlet);
5.2–5.9 (2H, multiplet);
6.8–7.5 (5H, multiplet).

1(m)

5-Oxo-16-phenoxy-17,18,19,20-tetranororostaglandin E₁ 11,15-di(tetrahydropyran-2-yl) ether methyl ester A mixture of 0.85 ml of dimethyl sulfoxide and 1.6 ml of methylene chloride was added at −65° C. to a solution of 0.52 ml of oxalyl chloride in 8 ml of methylene chloride. A solution of 320 mg of methyl 5,9α-dihydroxy-11α15α-di(tetrahydropyran-2-yloxy)16-phenoxy-17,18,19,20-tetranorprost-13(E)-enoate [prepared as described in Example 1(l)]in 3.2 ml of methylene chloride was then added to the resulting mixture at −65° C. to −55° C., and the mixture was stirred for 15 minutes. At the end of this time, 3.77 ml of triethylamine were added at −70° C. to −60° C. to the reaction mixture. The mixture was then stirred at room temperature for about 30 minutes, after which it was diluted with a saturated aqueous solution of sodium chloride and extracted with ethyl acetate. The extract was washed with a saturated aqueous solution of sodium chloride with cooled 2% v/v aqueous hydrochloric acid and with a saturated aqueous solution of sodium chloride, in that order, and dried over anhydrous sodium sulfate, after which the solvent was removed by distillation under reduced pressure. The residue was purified by silica gel column chromatography, to give 264 mg of the title compound as an oily substance from those fractions eluted with hexane containing ethyl acetate in proportions ranging from 24–40% by volume Infrared Absorption Spectrum (liquid film) $\nu_{max}$ cm⁻¹: 1738, 1712, 1600, 1583, 1028.

Nuclear Magnetic Resonance Spectrum (CDC₃) δ ppm:
 3.65 (3H, singlet);
 5.6–6.1 (2H, multiplet);
 6.8–7.5 (5H, multiplet).

1(n)

5-Oxo-16-phenoxy-17,18,19,20-tetranorprostaglandin E₁ methyl ester 2.5ml of acetic acid and 6.8 ml of water were added to 1.0 ml of a tetrahydrofuran solution containing 250 mg of 5-oxo-16-phenoxy-17,18,19,20-tetranorprostaglandin E₁ 11,15-di(tetrahydropyran-2-yl) e ester [prepared as described in Example 1(m)], and the mixture was warmed to 40° C. and stirred for 3 hours, during which time a further 33 ml of water was added. At the end of this time, the reaction mixture was diluted with a saturated aqueous solution of sodium chloride and extracted with ethyl acetate. The extract was washed with a saturated aqueous solution of sodium chloride and dried over anhydrous sodium sulfate, and the solvent was then removed by distillation under reduced pressure. The residue was purified by silica gel column chromatography, to give 134 mg of the title compound as an oily substance from those fractions eluted with hexane containing ethyl acetate in proportions ranging from 65–90% by volume.

Infrared Absorption Spectrum (liquid film) $\nu_{max}$⁻¹: 3400, 1736, 1720 (shoulder), 1598, 1584 1240, 970.

Nuclear Magnetic Resonance Spectrum (CDCl₃), δ ppm:
 3.63 (3H, singlet);
 5.77 (2H, multiplet);
 6.714 7.5 (5H, multiplet).
 $[\alpha]_D^{25} = -50.7°$ (c=1, methanol).

EXAMPLE 2

5-Oxo-16,16-dimethylprostaglandin E₁ methyl ester and its 15R-isomer

2(a) Methyl 5,9α-diacetoxy-11α-(tetrahydropyran-2-yloxy)-15-oxo-16,16-dimethylprost-13(E)-enoate 0.12 g of sodium hydride (as a 55% w/w dispersion in mineral oil, and which had been washed with hexane) was suspended in 30 ml of tetrahydrofuran. 820 mg of dimethyl 2-oxo 3,3-dimethylheptylphosphonate were then added, whilst ice cooling, to the resulting suspension, and the mixture was stirred at room temperature for 1 hour. At the end of this time, a solution of 960 mg of 1α-acetoxy-2α-(3-acetoxy-2-methoxycarbonylhexyl)3β-formyl-4α-(tetrahydropyran 2-yloxy)cyclopentane [prepared as described in Example 1(h)]in 10 ml of tetrahydrofuran was then added, whilst ice-cooling, and the mixture was stirred at 10° C. for 3 hours. The reaction mixture was then treated in the same manner as described in Example 1(i), to give 1.12 g of the title compound as an oily substance.

Infrared Absorption Spectrum (liquid film) $\nu_{max}$ cm⁻¹: 1738, 1692, 1626, 1240, 1020.

Nuclear Magnetic Resonance Spectrum (CDCl₃) δ ppm:
 1.13 (6H, singlet);
 2.01 (3H, singlet);
 2.07 (3H, singlet);
 3.68 (3H, singlet);
 4.55 (1H, multiplet);
 4.70 (1H, multiplet);
 5.15 (1H, multiplet);
 6.72 (2H, multiplet).

(b) Methyl 5,9α-diacetoxy-11α-(tetrahydropyran-2-yloxy)-15-hydroxy-16,16-dimethylprost-13(E)-enoate Following a procedure similar to that described in Example 1(j), but reacting 1.10 g of methyl 5,9α-diacetoxy-11α-(tetrahydropyran-2-yloxy)-15-α16,16-dimethylprost-13(E)-enoate [prepared as described in Example 2(a)] with the sodium borohydride, 1.03 g of the title compound was obtained as an oily substance.

Infrared Absorption Spectrum (liquid film) $\nu_{max}$ cm⁻¹: 3530, 1740, 1242, 1020.

Nuclear Magnetic Resonance Spectrum (CDCl₃), δ ppm:
 0.82 (3H, singlet);
 0.86 (3H, singlet);
 2.00 (3H, singlet);
 2.05 (3H, singlet);
 3.66 (3H, singlet);
 5.15 (1H, multiplet);
 5.62 (2H, multiplet).

2(c) Methyl 5.9α-diacetoxy-11α,15-di(tetrahydropyran2-yloxy)-16.16-dimethylprost-13(E)-enoate Following a procedure similar to that described in Example 1(k), but reacting 1.01 g of methyl 5,9α-diacetoxy-11α-(tetrahydropyran-2 yloxy) 15-hydroxy-16,16-dimethylprost-13(E)-enoate [prepared as described in Example 2(b)]with the dihydropyran, 1.22 g of the title compound was obtained as an oily substance.

Infrared Absorption Spectrum (liquid film) $\nu_{max}$ cm⁻¹: 1740, 1242, 1020.

Nuclear Magnetic Resonance Spectrum (CDCl$_3$), δ ppm:
0.85 (3H, singlet);
0.90 (3H, singlet):
2.01 (3H, singlet);
2.05 (3H, singlet);
3.66 (3H, singlet);
5.45 (2H, multiplet).

2(d) Methyl 5,9α-dihydroxy-11α15-di(tetrahydropyran-2-yloxy)-16 16-dimethylprost-13(E)-enoate Following a procedure similar to that described in Example 1(l), but reacting 1.20 g of methyl 5,9α-diacetoxy 11α15-di(tetrahydropyran-2-yloxy)-16,16-dimethylprost-13(E)-enoate [prepared as described in Example 2(c)] with the potassium carbonate, 872 mg of the title compound were obtained as an oily substance.

Infrared Absorption Spectrum (liquid film) $v_{max}$ $^{-1}$: 3420, 1740, 1016.

Nuclear Magnetic Resonance Spectrum (CDCl$_3$), δ ppm:
3.67 (3H, singlet);
4.68 (2H, broad singlet);
5.45 (2H, multiplet).

2(e) A mixture of 5-oxo-16,16-dimethylprostaglandin E 11,15-di(tetrahydropyran-2-yl) ether methyl ester and its 15R-isomer Following a procedure similar to that described in Example 1(m), but reacting 850 mg of methyl 5,9α-dihydroxy 11α15-di(tetrahydropyran-2 yloxy)16,16-dimethylprost-13(E)-enoate [prepared as described in Example 2(d)] with oxalyl chloride and dimethyl sulfoxide, 526 mg of the title compound were obtained as an oily substance.

Infrared Absorption Spectrum (liquid film) $v_{max}$ cm$^{-1}$: 1746, 1718, 1022, 978.

Nuclear Magnetic Resonance Spectrum (CDCl$_3$) δ ppm:
0.7–1.1 (9H, multiplet);
3.67 (3H, singlet);
4.68 (2H, broad singlet)
5.55 (2H, multiplet).

2(f) 5-Oxo-16,16-dimethylprostaglandin E$_1$ methyl ester and its 15R-isomer Following a procedure similar to that described in Example 1(n), but reacting 520 mg of the mixture of 5-oxo-16,16-dimethylprostaglandin E$_1$ 11,15 di(tetrahydropyran-2-yl) ether methyl ester and its 15R-isomer [prepared as described in Example 2(e)] and acetic acid. 72 mg of the title compound, melting at 60–65° C., were obtained as the substance of higher polarity and 64 mg of the 15R-isomer were obtained as the substance of lower polarity.

Title Compound;
Infrared Absorption Spectrum (liquid film) $v_{max}$ cm$^{-1}$: 3410, 1738, 972.

Nuclear Magnetic Resonance Spectrum (CDCl$_3$) δ ppm:
0.7–1.05 (9H, multiplet);
3.66 (3H, singlet);
5.67 (2H, multiplet).
$[α]_D \cong -35.3°$ (c=1, methanol).

15R-isomer:
Infrared Absorption Spectrum (liquid film) $v_{max}$ cm$^{-1}$: 3450, 1740, 975.

EXAMPLE 3

5-Oxoprostaglandin E$_1$ methyl ester

3(a) 5-Oxoprostaglandin E$_1$ 11,15-di(tetrahydropyran2-yl) ether methyl ester Following a procedure similar to that described in Examples 2(a)–(e), and in the same order, but reacting 1.09 g of 1α-acetoxy-2α-(3-acetoxy-δ methoxycarbonylhexyl)-3β-formyl 4α-(tetrahydropyran-2-yloxy)-cyclopentane [prepared as described in Example 1h)] and 800 mg of dimethyl 2-oxoheptylphosphonate, 342 mg of the title compound were obtained as an oily substance.

Infrared Absorption Spectrum (liquid film) $v_{max}$ cm$^{-1}$: 1740, 1716 (shoulder), 1018, 970.

Nuclear Magnetic Resonance Spectrum (CDCl$_3$), δ ppm:
3.68 (3H, singlet);
3 72 (2H, multiplet);
5.60 (2H, multiplet).

3(b) 5-Oxoprostaglandin E$_1$ methyl ester

Following a procedure similar to that described in Example 2(f), but reacting 330 mg of 5-oxoprostaglandin E$_1$ 11,15-di(tetrahydropyran-2-yl) ether methyl ester [prepared as described in Example 3(a)] and acetic acid, 199 mg of the title compound were obtained as an oily substance.

Infrared Absorption Spectrum (liquid film) $v_{max}$ $^{-1}$: 3400, 1738, 970.

Nuclear Magnetic Resonance Spectrum (CDCl$_3$), δ ppm:
0.88 (3H, broad triplet);
3.66 (3H, singlet):
5.60 (2H, multiplet).

EXAMPLE 4

5-Oxo-17(S)-methyl-20-isopropylideneprostaglandin E$_1$ methyl ester

4(a) 5-Oxo-17(S)-methyl-20-isopropylideneprostaglandin

E$_1$ 11,15-di(tetrahydropyran-2-yl) ether methyl ester

Following a procedure similar to that described in Examples 2(a)–(e), and in the same order, but reacting 1.01 g of 1α-acetoxy-2α-(3-acetoxy-6-methoxy-carbonylhexyl)-3α-formyl-4α-(tetrahydropyran-2-yloxy)-cyclopentane [prepared as described in Example 1(h)] and 0.92 g of dimethyl 2-oxo-4(S),8-dimethylnonylphosphate, 356 mg of the title compound were obtained as an oily substance.

Infrared Absorption Spectrum (liquid film) $v_{max}$ cm$^{-1}$: 1740, 1019, 970.

Nuclear Magnetic Resonance Spectrum (CDCl$_3$), δ ppm:
3.66 (3H, singlet);
4.70 (2H, broad singlet);
5.60 (2H, multiplet).

4(b)

5-Oxo-17(S)-methyl-20-isopropylideneprostaglandin E$_1$ methyl ester

Following a procedure similar to that described in Example 2(f), but reacting 350 mg of 5-oxo-17(S)-methyl-20-isopropylideneprostaglandin E$_1$ 11,15-di(tetrahydropyran-2-yl) ether methyl ester [prepared as described in Example 4(a)]and acetic acid, 193 mg of the title compound were obtained as an oily substance.

Infrared Absorption Spectrum (liquid film) $\nu_{max}$ $^{-1}$: 3400, 1738, 970.

Nuclear Magnetic Resonance Spectrum (CDCl$_3$), $\delta$ ppm:
 0.7–1.1 (3H, multiplet);
 1.60 (3H, singlet);
 1.68 (3H, singlet);
 3.68 (3H, singlet);
 5.08 (1H, broad triplet);
 5.60 (2H, multiplet).

EXAMPLE 5

5-Oxo-17(S),20-dimethylprostaglandin E$_1$ methyl ester (a) 5-Oxo-17(S),20-dimethylprostalandin E$_1$ 11,15-di(tetrahydropyran-2-yl) ether methyl ester Following a procedure similar to that described in Examples 2(a)–(e), and in the same order, but reacting 1.03 g of 1α-acetoxy-2α-(3-acetoxy-6-methoxycarbonylhexyl) 3μ-formyl-4α-(tetrahydropyran 2-yloxy)-cyclopentane [prepared as described in Example 1(h)] and 820 mg of dimethyl 2-oxo-4(S)-methyloctylphosphonate, 324 mg of the title compound were obtained as an oily substance.

Infrared Absorption Spectrum (liquid film) $\nu_{max}$ cm$^{-1}$: 1739, 1020, 970.

Nuclear Magnetic Resonance Spectrum (CDCl$_3$), $\delta$ ppm:
 3.66 (3H, singlet);
 4.67 (2H, broad singlet);
 5.57 (2H, multiplet).

5(b) 5-Oxo-17(S),20-dimethylprostaglandin E$_1$ methyl ester

Following a procedure similar to that described in Example 2(f), but reacting 310 mg of 5-oxo-17(S),20 dimethylprostaglandin E$_1$ 11,15-di(tetrahydropyran2-yl) ether methyl ester [prepared as described in Example 5(a)]and acetic acid, 166 mg of the title compound were obtained as an oily substance.

Infrared Absorption Spectrum (liquid film) $\nu_{cm}$$^{-1}$: 3400, 1738, 1716 (shoulder), 970.

Nuclear Magnetic Resonance Spectrum (CDCl$_3$), $\delta$ ppm:
 0.16–1.05 (6H, multiplet);
 3.68 (2H, singlet);
 5.62 (2H, multiplet).

EXAMPLE 6

5-Oxo-17(R)-methyl-20-isopropylideneprostaglandin E$_1$ methyl ester

Following a procedure similar to that described in Examples 2(a)–(f). and in the same order, but reacting 1.05 g of 1α-acetoxy 2α-(3-acetoxy-6-methoxycarbonylhexyl)-3β-formyl-4α-(tetrahydropyran-2-yloxy)cyclopentane [prepared as described in Example 1(h)]and 980 mg of dimethyl 2-oxo-4(R),8-dimethyl 7-nonenylphosphonate, 111 mg of the title compound were obtained as an oily substance.

Infrared Absorption Spectrum (liquid film) $\nu_{max}$ cm$^{-1}$:
 3400, 1740, 1716 (shoulder), 972.

Nuclear Magnetic Resonance Spectrum (CDCl$_3$). $\delta$ ppm:
 0.90 (3H, doublet. J=6 Hz).
 1.57 (3H, singlet);
 1.64 (3H, singlet);
 3.62 (3H, singlet);
 5.04 (1H, broad triplet);
 5.56 (2H, multiplet).

This methyl ester can be converted into the carboxylic acid by reaction with an esterase under conventional conditions.

EXAMPLE 7

5-Oxo-16,16-dimethyl 17-ethoxy 18,19,20-trinorprostaglandin E$_1$ methyl ester

7(a) A mixture of 5-oxo-16,16-dimethyl-17-ethoxy18,19,20-trinorprostaglandin E$_1$ 11,15-di(tetrahydropyran-2-yl) ether methyl ester and its 15R-isomer Following a procedure similar to that described in Examples 1(i)–(m). and in the same order but reacting 990 mg of 1α-acetoxy-2α-(3-acetoxy-6-methoxycarbonylhexyl)-3β-formyl-4α-(tetrahydropyran-2-yloxy)-cyclopentane [prepared as described in Example 1(h)]and 1.65 g of dimethyl 2-oxo-3,3-dimethyl 4 ethoxybutylphosphonate, 690 mg of the title compound were obtained as an oily substance.

Infrared Absorption Spectrum (liquid film) $\nu_{max}$ cm$^{-1}$: 1740, 1716, 1030.

Nuclear Magnetic Resonance Spectrum (CDCl$_3$), $\delta$ ppm:
 3.67 (3H, singlet);
 4.68 (2H, broad singlet);
 5.55 (2H, multiplet).

7(b) 5-Oxo-16,16-dimethyl-17-ethoxy-18,19,20-trinorprostaglandin E$_1$ methyl ester Following a procedure similar to that described in Example 1(n). but reacting 930 mg of the mixture of 5-oxo-16,16-dimethyl-17-ethoxy-18,19,20-trinorprostaglandin E$_1$ 11,15-di(tetrahydropyran-2-yl) ether methyl ester and its 15R-isomer [prepared as described in Example 7(a)] and acetic acid, 144 mg of the title compound were obtained as an oily substance.

Infrared Absorption Spectrum (liquid film) $\nu_{max}$ cm$^{-1}$: 3125, 1740, 1718 (shoulder). 972.

Magnetic Resonance Spectrum (CDCl$_3$), $\delta$ ppm:
 0.91 (6H, singlet);
 3H, singlet);
 5.68 (2H, multiplet).

EXAMPLE 8

5-Oxo-16,16-dimethyl-20-methyleneprostaglandin E$_1$ methyl ester

8(a) A mixture of 5-oxo-16,16-dimethyl-20-methyleneprostaglandin E$_1$ 11,15-di(tetrahydrofuran-2-yl) ether methyl ester and its 15R-isomer Following a procedure similar to that described in Examples 2(a)–(e), and in the same order, but reacting 990 mg of 1α-acetoxy-2α-(3-acetoxy-6-methoxycarbonylhexyl)-3β-formyl-4-α-(tetrahydropyran-2-yloxy)-cyclopentane [prepared as described in Example 1(h)] and 820 mg of dimethyl 2-oxo-3,3-dimethyl 6-heptenylphosphonate, 830 mg of the title compound were obtained as an oily substance.

Infrared Absorption Spectrum (liquid film) $\nu_{max}$ cm$^{-1}$: 1740, 1714 (shoulder), 1640, 1020.

Nuclear Magnetic Resonance Spectrum (CDCl$_3$), δ ppm:
 0.90 (3H, singlet);
 0.93 (3H, singlet):
 3.67 (3H, multiplet);
 4.6–6.1 (7H, multiplet).

8(b) 5-Oxo-16,16-dimethyl-20-methyleneprostaglandin E$_1$ methyl ester

Following a procedure similar to that described in Example 2(f), but reacting 820 mg of the mixture of 5-oxo-16,16-dimethyl-20-methyleneprostaglandin E$_1$ 11,15-di(tetrahydropyran-2-yl) ether methyl ester and its 15R-isomer [prepared as described in Example 8(a)] and acetic acid, 173 mg of the title compound were obtained as an oily substance.

Infrared Absorption Spectrum (liquid film) ν$_{max}$ cm$^{-1}$: 3425, 1740, 1718 (shoulder), 1640, 970.

Nuclear Magnetic Resonance Spectrum (CDCl$_3$), δ ppm
 0.88 (3H, singlet);
 0.90 (3H, singlet);
 3.68 (3H, singlet);
 4.7–6.1 (5H, multiplet).

EXAMPLE$_1$ 9

5-Oxo-15-cvclopentyl-16,17,18,19,20-pentanorprostaglandin E$_1$ methyl ester

9(a) 5-Oxo-15-cyclopentyl-16,17,18,19,20-pentanorprostaglandin E$_1$ 11,15-di(tetrahydropyran-2-yl) ether methyl ester Following a procedure similar to that described in Examples 2(a)–(e). and in the same order, but reacting 1.18 g of 1α-acetoxy-2α-(3-acetoxy-6-methoxycarbonylhexyl)3μ-formyl-4α-(tetrahydropyran-2-yloxy)cyclopentane [prepared as described in Example 1(h)] and 800 mg of dimethyl 2-oxo-2-cyclopentylethylphosphonate, 305 mg of the title compound were obtained as an oily substance.

Infrared Absorption Spectrum (liquid film) ν$_{max}$ cm$^{-1}$:1 1740, 1712 (shoulder), 1020.

Nuclear Magnetic Resonance Spectrum (CDCl$_3$). δ ppm:
 3.70 (3H, singlet);
 4.71 (2H, broad singlet);
 5.58 (2H, multiplet).

9(b) 5-Oxo-15-cyclopentyl-16,17,1,19,20-pentanorprostaglandin E$_1$ methyl ester Following a procedure similar to that described in Example 2(f). but reacting 300 mg of 5-oxo-15-cycla--pentyl-16,17,18,19,20-pentanorprostaglandin E$_1$ b 11,15-di(tetrahydropyran-2-yl) ether methyl ester [prepared as described in Example 9(a)] and acetic acid, 169 mg of the title compound were obtained as an oily substance, which was crystallized, whilst cooling.

Infrared Absorption Spectrum (liquid film) ν$_{max}$ cm$^{-1}$: 3410, 1740, 1720 (shoulder), 975.

Nuclear Magnetic Resonance Spectrum (CDCl$_3$), δ ppm:
 3.68 (3H, singlet);
 5.62 (2H, multiplet). [α]$_D^{24}$= −48.2° (c=1, methanol).

EXAMPLE 10

5-Oxo-16-m-chlorophenoxy-17,18,19,20-tetranorprostaglandin E$_1$ methyl ester

10(a) A mixture of 5-oxo-16-m-chlorophenoxy-17,18,19,20tetranorprostaglandin E$_1$ 11,15-di(tetrahydropyran-2-yl) ether methyl ester and its 15R-isomer Following a procedure similar to that described in Examples 1(i)–(m). and in the same order, but reacting 1.50 g of 1α-acetoxy 2α-(3-acetoxy6-methoxycarbonylhexyl)-3β-formyl-4α-(tetrahydropyran-2-yloxy)cyclopentane [prepared as described in Example 1(h)] and 2.88 g of dimethyl 2-oxo-3 m-chlorophenoxypropylphosphonate. 939 mg of the title compound were obtained as an oily substance.

Infrared Absorption Spectrum (liquid film) ν$_{max}$ cm$^{-1}$: 1740, 1714 (shoulder), 1596, 1580, 1020.

Nuclear Magnetic Resonance Spectrum (CDCl$_3$), δ ppm:
 3.68 (3H, singlet);
 5.80 (2H, multiplet);
 6.7–7.4 (5H, multiplet).

10(b) 5-Oxo-16-m-chlorophenoxy-17,18,19,20-tetranorprostaglandin E$_1$ methyl ester Following a procedure similar to that described in Example 1(n), but reacting 920 mg of the mixture of 5-oxo-16-m-chlorophenoxy-17,18,19,20-tetranorprostaglandin E$_1$ 11,15-di(tetrahydropyran-2-yl) ether methyl ester and its 15R-isomer [prepared as described in Example 10(a)] and acetic acid, 260 mg of the title compound were obtained as an oily substance, together with 310 mg of its 15S-isomer.

Title Compound

Infrared Absorption Spectrum (liquid film) ν$_{max}$ cm$^{-1}$: 3425, 1735, 1715 (shoulder), 1594, 1580, 970.

Nuclear Magnetic Resonance Spectrum (CDCl$_3$), δ ppm: 3.66 (3H, singlet); 5.84 (2H, multiplet); 6.8–7.5 (5H, multiplet). [α]$_D^{24}$= −47.8° (c=1, methanol).

15S-isomer:

Infrared Absorption Spectrum (liquid film) ν$_{max}$ cm$^{-1}$: 3425, 1735, 1595, 1580, 971.

EXAMPLE 11

5-Oxo-16-p-chlorophenoxy-17,18,19,20-tetranorprostaglandin E$_1$ methyl ester

Following a procedure similar to that described in Examples 1(i)–(n), and in the same order, but reacting 990 mg of 1α-acetoxy 2α-(3-acetoxy6-methoxycarbonylhexyl)-3β-formyl-4α-(tetrahydropyran-2yloxy)-cyclopentane [prepared as described in Example 1(h)] and 1.92 g of dimethyl 2-oxo-3-p-chlorophenoxypropylphosphonate, 180 g of the title compound and 190 mg of its 15S-isomer were obtained, both as oily substances.

Title Compound:

Infrared Absorption Spectrum (liquid film) ν$_{max}$ cm$^{-1}$: 3425, 1736, 1718 (shoulder), 1598, 1582, 970.

Nuclear Magnetic Resonance Spectrum (CDCl$_3$), δ ppm:
 3.64 (3H, singlet);
 5.82 (2H, multiplet);
 6.7–7.5 (5H, multiplet).
 [α]$_D^{24}$= −47.1° (c=1, methanol), 15S-isomer:

Infrared Absorption Spectrum (liquid film) $\nu_{max}$ cm$^{-1}$:
3425, 1738, 1598, 1582, 970.

EXAMPLE 12

5-Oxo-16-α-chlorophenoxy-17,18,19,20-tetranorprostaglandin E$_1$ methyl ester

Following a procedure similar to that described in Examples 1(i)–(n). and in the same order, but reacting 1.02 g of 1α-acetoxy-2α-(3-acetoxy-6-methoxy carbonylhexyl)-3β-formyl-4α-(tetrahydropyran-2-yloxy)-cyclopentane [prepared as described in Example 1(h)] and 1.92 g of dimethyl 2-oxo-3-o-chlorophenoxypropylphosphonate, 161 mg of the title compound and 190 mg of its 15S-isomer were obtained as oily substances.
Title Compound:
Infrared Absorption Spectrum (liquid film) $\nu_{max}$ cm$^{-1}$: 3425, 1738, 1718 (shoulder), 1592, 972.
Nuclear Magnetic Resonance Spectrum (CDCl$_3$) δ ppm:
3.63 (3H, singlet);
5.82 (2H, multiplet);
6.7-7.5 (5H, multiplet).
$[\alpha]_D^{24} = -37.1°$ (c=1, methanol).
15S-isomer:
Infrared Absorption Spectrum (liquid film) $\nu_{max}$ cm$^{-1}$: 3425, 1738, 1592, 972.

EXAMPLE 13

5-Oxo-16,16,20-trimethylprostaglandin E$_1$ methyl ester

Following a procedure similar to that described in Examples 2(a)–(f), and in the same order, but reacting 1.00 g of 1α-acetoxy-2α-(3-acetoxy-6-methoxycarbonylhexyl)-3β-formyl-4α-(tetrahydropyran-2-yloxy)-cyclopentane [prepared as described in Example 1(h)] and 900 mg of dimethyl 2-oxo-3,3 dimethyloctylphosphonate, 78 mg of the title compound were obtained as an oily substance.
Infrared Absorption Spectrum (liquid film) $\nu_{max}$ cm$^{-1}$: 3420, 1738, 1717 (shoulder), 972.
Nuclear Magnetic Resonance Spectrum (CDCl$_3$), δ ppm: 0.7-1.05 (9H, multiplet); 3.67 (3H, singlet); 5.66 (2H, multiplet).

EXAMPLE 14

5-Oxo-16,16-dimethyl-20-ethylprostaglandin E$_1$ methyl ester

Following a procedure similar to that described in Examples 2(a)–(f). and in the same order, but reacting 1.00 g of 1α-acetoxy 2α-(3-acetoxy-6-methoxycarbonylhexyl)-38-formyl-4α-(tetrahydropyran-2-yloxy)cyclopentane [prepared as described in Example 1(h)] and 950 mg of dimethyl 2-oxo-3,3-dimethylnonylphosphate, 67 mg of the title compound were obtained as an oily substance.
Infrared Absorption Spectrum (liquid film) $\nu_{max}$ cm$^{-1}$: 3410, 1738, 1719 (shoulder), 972.
Nuclear Magnetic Resonance Spectrum (CDCl$_3$), δ ppm:
0.7-1.05 (9H, multiplet);
3.66 (3H, singlet);
5.65 (2H, multiplet).

EXAMPLE 15

5-Oxo-16-methylprostaglandin E$_1$ methyl ester

Following a procedure similar to that described in Examples 2(a)–(f), and in the same order, but reacting 980 mg of 1α-acetoxy-2α-(3-acetoxy6-methoxycarbonylhexyl)-3β-formyl-4α-(tetrahydropyran 2-yloxy)-cyclopentane [prepared as described in Example 1(h)] and 920 mg of dimethyl 2-oxo-3-methylheptylphosphate, 61 mg of the title compound were obtained as an oily substance.
Infrared Absorption Spectrum (liquid film) $\nu_{max}$ cm$^{-1}$: 3420, 1738, 1718 (shoulder), 971.
Nuclear Magnetic Resonance Spectrum (CDCl$_3$), δ ppm:
0.7-1.05 (6H, multiplet)
3.66 (3H, singlet);
5.66 (2H, multiplet).

EXAMPLE 16

5-Oxo-16-methyl-20-isopropylideneprostaglandin E$_1$ methyl ester

Following a procedure similar to that described in Examples 2(a)–(f), and in the same order, but reacting 980 mg of 1α-acetoxy-2u-(3-acetoxy-6-methoxy carbonylhexyl) 3μ-formyl-4α-(tetrahydropyran-2-yloxy)-cyclopentane [prepared as described in Example 1(h)] and 910 mg of dimethyl 2-oxo-3,8-dimethyloctylphosphonate, 251 mg of the title compound were obtained as an oily substance.
Infrared Absorption Spectrum (liquid film) $\nu_{max}$ cm$^{-1}$: 3460, 1742, 1724 (shoulder), 971.
Nuclear Magnetic Resonance Spectrum (CDCl$_3$), δ ppm:
0.90 (3H, doublet);
1.59 (3H, singlet);
1.67 (3H, singlet);
3.67 (3H, singlet);
5.10 (1H, broad triplet):
5.68 (2H, multiplet).

EXAMPLE 17

5-Oxo-16,19-dimethyl-18,19-didehydroprostaglandin E$_1$ methyl ester

Following a procedure similar to that described in Examples 2(a)–(f). and in the same order, but reacting 1.01 q of 1a-acetoxy 2α-(3-acetoxy δ methoxycarbonylhexyl)-b 38-formyl-4α-(tetrahydropyran-2-yloxy)cyclopentane [prepared as described in Example 1(h)] and 820 mg of dimethyl 2-oxo 3,6-dimethyl-5-heptenylphosphonate, 235 mg of the title compound were obtained as an oily substance.
Infrared Absorption Spectrum (liquid film) $\nu_{max}$ cm$^{-1}$: 3425, 1740, 1720 (shoulder), 972.
Nuclear Magnetic Resonance Spectrum (CDCl$_3$), δ ppm:
0.89 (3H, multiplet);
1.62 (3H, singlet);
1.70 (3H, singlet);
3.66 (3H, singlet);
5.16 (1H, broad multiplet);
5.67 (2H, multiplet).

EXAMPLE 18

5-Oxo-16-methyl-16-phenoxy-17,18,19,20-tetranorprostaglandin E$_1$ methyl ester

Following a procedure similar to that described in Examples 1(i)–(n). and in the same order, but reacting 1.01 g of 1α-acetoxy-2α-(3-acetoxy 6-methoxycarbonylhexyl)-3β-formyl-4α-(tetrahydropyran 2-yloxy)cyclopentane [prepared as described in Example 1(h)] and 890 mg of dimethyl 2 oxo-3-methyl 3 phenoxypropylphosphonate, propylphosphonate, 165 mg of the title compound were obtained as an oily substance.

Infrared Absorption Spectrum (liquid film) $\nu_{max}$ cm$^{-1}$: 3430, 1740, 1710 (shoulder), 971.

Nuclear Magnetic Resonance Spectrum (CDCl$_3$), δ ppm: 1.28 (3H, doublet); 3.66 (3H, singlet); 5.78 (2H, multiplet); 6.8–7.5 (5H, multiplet).

EXAMPLE 19

5-Oxo-16-p-fluorophenoxy-17,18,19,20-tetranorprostaglandin E$_1$ methyl ester

Following a procedure similar to that described in Examples 1(i)–(n), and in the same order, but reacting 1.00 g of 1α-acetoxy-2α-(3-acetoxy-6-methoxycarbonylhexyl)-3β-formyl-4α-(tetrahydropyran-2-yloxy)-cyclopentane [prepared as described in Example 1(h)] and 910 mg of dimethyl 2-oxo-3-p-fluorophenoxypropylphosphonate, 210 mg of the title compound were obtained as an oily substance.

Infrared Absorption Spectrum (liquid film) $\nu_{max}$ cm$^{-1}$: 3420, 1738, 1720 (shoulder), 1602, 972.

Nuclear Magnetic Resonance Spectrum (CDCl$_3$), δ ppm:
3.64 (3H, singlet);
5.80 (2H, multiplet);
6.7–7.1 (4H, multiplet). $[\alpha]_D^{24} = -46.1°$ (c=1, methanol).

EXAMPLE 20

5-Oxo-16-m-fluorophenoxy-17,18,19,20-tetranorprostaglandin E$_1$ methyl ester

Following a procedure similar to that described in Examples 1(i)–(n). and in the same order, but reacting 1.00 g of 1α-acetoxy-2o (3-acetoxy 6-methoxy carbonylhexyl) 3β-formyl-4u-(tetrahydropyran-2 yloxy)-cyclopentane [prepared as described in Example 1(h)] and 910 mg of dimethyl 2-oxo-3-m-fluorophenoxypropylphosphonate, 213 mg of the title compound were obtained as an oily substance.

Infrared Absorption Spectrum (liquid film) $\nu_{max}$ cm$^{-1}$: 3425, 1740, 1722 (shoulder), 971.

Nuclear Magnetic Resonance Spectrum (CDCl$_3$) δ ppm:
3.63 (3H, singlet);
5.81 (2H, multiplet);
6.68 (3H, multiplet). $[\alpha]_D^{24}$48.1° (c=1, methanol).

EXAMPLE 21

5-Oxo-16-α-fluorophenoxy-17,18,19,20-tetranorprostaglandin E$_1$ methyl ester

Following a procedure similar to that described in Examples 1(i)–(n), and in the same order, but reacting 1.00 g of 1α-acetoxy-2α-(3-acetoxy-6-methoxycarbonylhexyl)-3β-formyl-4α-(tetrahydropyran-2-yloxy)-cyclopentane [prepared as described in Example 1(h)] and 1.34 g of dimethyl 2-oxo-3-o-fluorophenoxy propylphosphonate. 147 mg of the title compound were obtained as an oily substance.

Infrared Absorption Spectrum (liquid film) $\nu_{max}$ cm$^{-1}$:
3410, 1737, 1720 (shoulder), 971.

Nuclear Magnetic Resonance Spectrum (CDCl$_3$). δ ppm:
3.65 (3H, singlet);
5.82 (2H, multiplet);
6.8–7.3 (4H, multiplet). $[\alpha]_D^{24} = -37.7°$ (c=1, methanol).

EXAMPLE 22

5-Oxo-16-α-methoxyphenoxy-17,18,19,20-tetranorprostaglandin E$_1$ methyl ester

Following a procedure similar to that described in Examples 1(i)–(n). and in the same order, but reacting 2.00 g of 1α-acetoxy-2α-(3-acetoxy-6-methoxycarbonylhexyl)-3μ-formyl-4α-(tetrahydropyran.2-yloxy)-cyclopentane [prepared as described in Example 1(h)] and 1.9 g of dimethyl 2-oxo-3-p-methoxyphenoxypropylphosphonate, 232 mg of the title compound were obtained as an oily substance.

Infrared Absorption Spectrum (liquid film) $\nu_{max}$ cm$^{-1}$: 3430, 1736, 1716 (shoulder), 972.

Nuclear Magnetic Resonance Spectrum (CDCl$_3$), δ ppm:
3.65 (3H, singlet);
3.77 (3H, singlet);
5.81 (2H, multiplet);
6.88 (4H, singlet).

EXAMPLE 23

5-Oxo-16-(3,5-dimethylphenoxy)-17,18,19,20-tetranorprostaglandin E$_1$ methyl ester Following a procedure similar to that described in Examples 1(i)–(n), and in the same order, but reacting 1.00 g of 1α-acetoxy-2α-(3-acetoxy 6-methoxycarbonylhexyl)-3β-formyl-4α-(tetrahydropyran 2-yloxy)cyclopentane [prepared as described in Example 1(h)] and 950 mg of dimethyl 2-oxo-3 (3,5 dimethylphenoxy)-propylphosphonate, 251 mg of the title compound were obtained as an oily substance.

Infrared Absorption Spectrum (liquid film) $\nu_{max}$ cm$^{-1}$: 3416, 1738, 1718 (shoulder), 971.

Nuclear Magnetic Resonance Spectrum (CDCl$_3$), δ ppm:
2.28 (6H, singlet);
3.65 (3H, singlet);
5.82 (2H, multiplet);
6.66 (2H, singlet);
6.65 (1H, singlet).

EXAMPLE 24

5-Oxo-16-benzyloxy-17,18,19,20-tetranorprostaglandin E$_1$ methyl ester

Following a procedure similar to that described in Examples 1(i)–(n), and in the same order, but reacting 1.00 g of 1α-acetoxy-2α-(3-acetoxy-6-methoxycarbonylhexyl)-3β-formyl-4α-(tetrahydropyran-2yloxy)-cyclopentane [prepared as described in Example 1(h)] and 1.20 g of dimethyl 2-oxo-3-benzyloxypropylphosphonate, 230 mg of the title compound as an oily substance.

Infrared Absorption Spectrum (liquid film) $\nu_{max}$ cm$^{-1}$: 3420, 1737, 1712 (shoulder), 972.

Nuclear Magnetic Resonance Spectrum (CDCl$_3$), δ ppm:
3.65 (3H, singlet);
4.58 (2H, singlet);
5.81 (2H, multiplet);
7.37 (5H, singlet).

EXAMPLE 25

5-Oxo-16-(3,4-dichlorophenoxy)-17,18,19,20-tetranorprostaglandin $E_1$ methyl ester Following a procedure similar to that described in Examples 1(i)–(n). and in the same order, but reacting 2.00 g of 1α-acetoxy-2α-(3-acetoxy 6-methoxycarbonylhexyl)-3β-formyl-4α-(tetrahydropyran-2yloxy)cyclopentane [prepared as described in Example 1(h)]and 2.18 g of dimethyl 2-oxo 3-(3,4-dichloro phenoxy)-propylphosphonate, 79 mg of the title compound were obtained as an oily substance.

Infrared Absorption Spectrum (liquid film) $\nu_{max}$ cm$^{-1}$:
3400, 1741, 1718 (shoulder), 971.

Nuclear Magnetic Resonance Spectrum (CDCl$_3$), δ ppm:
3.67 (3H, singlet);
5.82 (2H, multiplet);
6.7 - 7.3 (3H. multiplet). $[\alpha]_{D-} = -43.7°$ (c=1. methanol).

EXAMPLE 26

5-Oxo-16-p-ethylphenoxy-17,18,19,20-tetranorprostaglandin $E_1$ methyl ester

Following a procedure similar to that described in Examples 1(i)14 (n). and in the same order but reacting 1.00 g of 1α-acetoxy-2o-(3-acetoxy 6-methoxy carbonylhexyl) 3(-formyl-4u-(tetrahydropyran-2yloxy)cyclopentane [prepared as described in Example 1(h)]and 1.1 g of dimethyl 2-oxo-3 p-ethylphenoxy propylphosphonate. 210 mg of the title compound were obtained as an oily substance. Infrared Absorption Spectrum (liquid film) ν cm$^{-1}$-1 3420, 1740, 1710 (shoulder). 972. Nuclear Magnetic Resonance Spectrum (CDCl$_3$), δ ppm:
1.23 (3H, triplet);
3.64 (3H. singlet);
5.79 (2H, multiplet);
6.75 - 7.3 (4H, multiplet). $[\alpha]_D^{24}$ 44.7° (c =1, methanol).

EXAMPLE 27

5-Oxo-16-p-acetamidophenoxy-17,18,19,20-tetranorprostaglandin $E_1$ methyl ester Following a procedure similar to that described in Examples 1(i)–(n). and in the same order, but reacting 2.00 g of 1α-acetoxy 2°-(3-acetoxy-6 methoxycarbonylhexyl)-3β-formyl-4α-(tetrahydropyran- 2yloxy)cyclopentane [prepared as described in Example 1(h)]and 2.6 g of dimethyl 2-oxo-3-p-acetamidophenoxypropylphosphonate, 71 mg of the title compound were obtained as an oily substance. However, in the step corresponding to the step of Example 1(i), the suspension of sodium hydride was added to the phosphonate compound, rather than vice versa.

Infrared Absorption Spectrum (CHCl$_3$)$\nu_{max}$ cm$^{-1}$:
3450, 3420, 1738, 1720 (shoulder) 1680, 1600, 972.

Nuclear Magnetic Resonance Spectrum (CDCl$_3$) δ ppm:
2.18 (3H, singlet);
3.65 (3H, singlet);
5.80 (2H, multiplet);
6.8-7.5 (4H, multiplet).

EXAMPLE 28

5-Oxo-16-(β-indolyl)-17,18,19,20-tetranorprostaglandin $E_1$ methyl ester

Following a procedure similar to that described in Examples 1(i)–(n). and in the same order, but reacting 2.00 g of 1α-acetoxy-2α-(3-acetoxy-6-methoxycarbonylhexyl)-3μ-formyl-4α-(tetrahydropyran 2yloxy)-cyclopentane [prepared as described in Example 1(h)]and 2.8 g of dimethyl 2-oxo-3-(β-indolyl)propylphosphonate, 59 mg of the title compound were obtained as an oily substance. However, in the step corresponding to the step of Example 1(i), the suspension of sodium hydride was added to the phosphonate compound, rather than vice versa.

Infrared Absorption Spectrum (CHCl$_3$)$\nu_{max}$ cm$^{-1}$: 3350, 1730, 972.

Nuclear Magnetic Resonance Spectrum (CDCl$_3$), δ ppm:
3.65(3H, singlet);
5.6 (2H, multiplet);
6.7-7.6 (5H, multiplet);
9.4 (1H, broad singlet).

EXAMPLE 29

Methyl 4,9-dioxo-11a,15o-dihydroxyprost-13(E)-enoate

29(a)

1-Decarboxy-1-hydroxymethyl-4-oxo-9α-hydroxy-11α, 15α-di(tetrahydropyran-2-yloxy)prost5(E),13(E)-dienoic acid di(dimethyl-t-butyl silyl) ether Following a procedure similar to that described in Example 2(a). but reacting 500 mg of 1α-(tetrahydro pyran-2-yloxy) 2β-(3α-tetrahydropyran-2-yloxy 1-octenyl)-3α-(2-oxoethyl)-4α-(dimethyl-t-butylsilyloxy)-cyclopentane and 470 mg of dimethyl 2-oxo 5-(dimethyl-t-butylsilyloxy)pentyl-phosphonate, 637 mg of the title compound were obtained as an oily substance.

Infrared Absorption Spectrum (liquid film)$\nu_{max}$ cm$^{-1}$: 1692. 1668. 1626.

Nuclear Magnetic Resonance Spectrum (CDCl$_3$) δ ppm:
0.91 (18H, singlet);
4.66 (2H, broad singlet):
45 (2H, multiplet):
8-7.2 (2H multiplet).

29(b)

1-Decarboxy-1-hydroxymethyl-4-oxo-9α-hydroxyl-1a, 15a-di(tetrahydropyran-2-yloxy)prost-13(E) enoic acid di(dimethyl-t-butylsilyl) ether 200 mg of chloro-tris(triphenylphosphine)rhodium (I) were added to a solution of 100 mg of 1-decarboxy 1-hydroxymethyl-4-oxo-9α-hydroxy-11α,15α-di(tetrahydropyran-2-yloxy)prost-5(E),13(E)-dienoic acid di(dimethyl-t-butylsilyl) ether [prepared as described in Example 29(a)]in 5 ml of benzene, and the mixture was stirred under an atmosphere of hydrogen for 15 hours. At the end of this time, the precipitate was removed from the reaction mixture by filtration and washed with ethyl acetate. The filtrate was combined with the washings, and the mixture was then freed from the solvent by evaporation under reduced pressure, to give 210 mg of a residue. This residue was purified by silica gel column chromatography, to give 78 mg of the title compound as an oily substance from the fractions eluted with hexane containing ethyl acetate in proportions ranging from 7–11% by volume.

Infrared Absorption Spectrum (liquid film)$\nu_{max}$ cm$^{-1}$: 1714.

Nuclear Magnetic Resonance Spectrum (CDCl$_3$) δ ppm:
0.90 (18H, singlet);
4.64 (2H, broad singlet);
5.38 (2H, multiplet). 29(c) 1-Decarboxy-1-hydroxymethyl-4-oxo-9α-hydroxy11α,15α-di(tetrahydropyran-2-yloxy)prost-13(E)enoic acid 0.93 ml of a 1M solution of tetrabutylammonium fluoride in tetrahydrofuran was added to a solution of 70 mg of 1 decarboxy-1-hydroxymethyl-4-oxo-9α-hydroxy,11α15α-di(tetrahydropyran-2-yloxy)prost 13(E) enoic acid di(dimethyl-t-butylsilyl) ether [prepared as described in Example 29(b)]in 1.4 ml of tetrahydrofuran, and the mixture was stirred at room temperature for 16 hours. At the end of this time, the reaction mixture was poured onto a saturated aqueous solution of sodium chloride, and the mixture was extracted with ethyl acetate. The extract was washed with a saturated aqueous solution of sodium chloride and dried over anhydrous sodium sulfate; the solvent was then removed by distillation under reduced pressure. The residue was purified by silica gel column chromatography, to give 44 mg of the title compound as an oily substance from the fractions eluted with hexane containing ethyl acetate in proportions ranging from 70–100% by volume.

Infrared Absorption Spectrum (liquid film) $\nu_{max}$cm$^{-1}$3450, 1708.

Nuclear Magnetic Resonance Spectrum (CDCl$_3$) δ ppm:

0.89 (3H, broad triplet);
4.68 (2H, broad singlet);
5.42 (2H, multiplet).

29(d) Methyl 4,9-dioxo-11α,15o-di(tetrahydropyran2-yloxy)prost-13(E)-enoate

A solution of 310 mg of 1-decarboxy-1-hydroxymethyl4-oxo 9c-hydroxy-11α15α-di(tetrahydropyran 2-yloxy)prost-13(E)-enoic acid [prepared as described in Example 29 (c)]in 5 ml of methylene chloride was added, whilst ice-coolinq, to a Collins reagent prepared from 1.18 g of chromic anhydride 1.90 ml of pyridine and 11 ml of methylene chloride, whilst ice-cooling, and the mixture was stirred for 30 minutes. At the end of this time, the reaction mixture was poured onto diethyl ether, the materials deposited were removed by filtration, and the ethereal layer was washed with water and dried; the solvent was then removed by distillation under reduced presSure. The residue was dissolved in 8.1 ml of acetone, and the resulting solution was added to a solution of 0.58 ml of Jones reagent in 5.4 ml of acetone at −10° C. to 30° C. The mixture was then stirred at this temperature for 30 minutes. At the end of this time, isopropanol was added to the reaction mixture, and the solution was poured onto ice-water and extracted with diethyl ether. The extract was washed with water and dried and the solvent was removed by distillation under reduced pressure. The residue was esterified with diazomethane and purified by silica gel column chromatography to give 240 mg of the title compound as an oily substance from the fractions eluted with hexane containing ethyl acetate in proportions ranging from 20–36% by volume.

Infrared Absorption Spectrum (liquid film)$\nu_{max}$ cm$^{-1}$: 1735, 1714.

Nuclear Magnetic Resonance Spectrum (CDCl$_3$) δ ppm:
0.87 (3H, broad triplet);
3.64 (3H, singlet);
4.69 (2H, broad singlet);
5.55 (2H, multiplet).

29(e) Methyl 4,9-dioxo-11α,15α-dihydroxyprost13(E)-enoate 5.1 ml of water were added to a solution of 230 mg of methyl 4,9-dioxo-11α,15α-di(tetrahydropyran2-yloxy)-prost-13(E)-enoate [prepared as described in Example 29(d)]in a mixture of 1 ml of tetrahydrofuran and 2.4 ml of acetic acid, and the mixture was stirred at 40° C. for 3 hours, during which time a further 13 ml of water were added. At the end of this time, the reaction mixture was poured onto ice-water and extracted with ethyl acetate. The extract was washed with a saturated aqueous solution of sodium chloride and dried, after which the solvent was removed by distillation under reduced pressure. The residue was purified by silica gel column chromatography, to give 134 mg of the title compound as an oily substance from the fractions eluted with hexane containing ethyl acetate in proportions ranging from 60 to 100% by volume.

Infrared Absorption Spectrum (liquid film) $\nu_{max}$ cm$^{-1}$:
3330, 1752, 1740, 1708.

Nuclear Magnetic Resonance Spectrum (CDCl$_3$) δ ppm:
0.90 (3H, broad triplet)
3.68 (3H, singlet):
5.66 (2H, multiplet). $[\alpha]_D^{24}=-52.9°$ (c=1. methanol).

EXAMPLE 30

Methyl 4,9-dioxo-11α,15α-dihydroxy-16-phenoxy17,18,19,20-tetranprprost 13(E)-enoate Following a procedure similar to that described in Example 29, but using 1.97 g of 1α-(tetrahydropyran2-yloxy) 2β-[(3α-tetrahydropyran-2-yloxy)-4-phenoxy1-butenyl]-3u-(2-oxoethyl)-4α-(dimethyl-t-butylsilyloxy)-cyclopentane. 139 mg of the title compound were obtained as an oily substance.

Infrared Absorption Spectrum (liquid film)$\nu_{max}$ cm$^{-1}$:
3400, 1740, 1718 (shoulder), 972.

Nuclear Magnetic Resonance Spectrum (CDCl$_3$) δ ppm:
3.66 (3H, singlet);
5.82 (2H, multiplet);
6.8–7.5 (5H, multiplet). $[\alpha]_D^{24}=-56.9°$ (c=1. methanol).

EXAMPLE 31

Methyl 4,9-dioxo-11α,15α-dihydroxy-16,16-dimethylprost 13(E) enoate

Following a procedure similar to that described in Example 29, but using 0.60 g of 1α-(tetrahydropyran 2-yloxy)-2β-[(3α-tetrahydropyran-2yl)oxy-4,4 dimethyl-1-octenyl-3α-(2-oxoethyl)-4α-(dimethyl t-butylsilyloxy)cyclopentane. 134 mg of the title compound were obtained as an oily substance.

Infrared Absorption Spectrum (liquid film) $\nu_{max}$ cm$^{-1}$: 1738, 1714 (shoulder), 972.

Nuclear Magnetic Resonance Spectrum (CDCl$_3$) δ ppm: 0.85 (3H, singlet); 0.87 (3H, singlet); 3.68 (3H, singlet); 5.7 (2H, multiplet). $[\alpha]_D^{24}$ D = $-34.8°$ (c=1, methanol).

EXAMPLE 32

Methyl 4,9-dioxo-11α,15α-dihydroxy-16-p-chlorophenoxy-17,18,19,20-tetranorprost-13(E)-enoate Following a procedure similar to that described in Example 29, but using 2.23 g of lo-(tetrahydropyran-yloxy)-2β-[(3α-tetrahydropyran 2yloxy)-4-p-chlorophenoxy-1-butenyl]-3α-(2-oxoethyl) 4α(dimethyl-t-butylsilyloxy)cyclopentane, 273 mg of the title compound were obtained as an oily substance.

Infrared Absorption Spectrum (liquid film) $\nu_{max}$ cm$^{-1}$: 3430, 1738, 1714 (shoulder), 971.

Nuclear Magnetic Resonance Spectrum (CDCl$_3$) δ ppm: 3.65 (3H, singlet); 5.82 (2H, multiplet); 6.88 (1H, doublet); 7.28 (1H, doublet). $[\alpha]_D^{24}$ = $-54.0°$ (c=1, methanol).

EXAMPLE 33

Methyl 5-oxo-16-o-methoxyphenoxy-17,18,19,20-tetranorprostaglandin E$_1$

Following a procedure similar to that described in Examples 1(i)–(n), but reacting 1.0 g of 1α-acetoxy 2α-(3-acetoxy-6-methoxycarbonylhexyl)-3β-formyl 4α(tetrahydropyran 2-yloxy)cyclopentane [prepared as described in Example 1(h)) and 1.27 g of dimethyl 2-oxo3-o-methoxyphenoxypropylphosphonate. 170 mg of the title compound were obtained as an oily substance.

Infrared Absorption Spectrum (liquid film) $\nu_{max}$ cm$^{-1}$: 3450, 1737, 1712 (shoulder), 1584, 976.

Nuclear Magnetic Resonance Spectrum (CDCl$_3$), δ ppm:
3.65 (3H, singlet);
3.85 (3H, singlet):
5.78 (2H, multiplet);
6.95 (4H, singlet). $[\alpha]_D^{24}$= $-41.4°$ (c=1, methanol).

EXAMPLE 34

Methyl 5-oxo-17-cyclohexyl-18,19,20-trinorprostaglandin E$_1$

Following a similar procedure to that described in Examples 2(a)–(f). but reacting 980 mg of la-acetoxy 2a-(3-acetoxy-6 methoxycarbonylhexyl)3β-formyl-4α-(tetrahydropyran-2-yloxy)cyclopentane [prepared as described in Example 1(h)]and 820 mg of dimethyl 2-oxo-4 cyclohexylbutylphosphonate, 152 mg of the title compound were obtained as an oily substance.

Infrared Absorption Spectrum (liquid film)$\nu_{max}$ cm$^{-1}$: 3420, 1740, 1720 (shoulder), 972.

Nuclear Maqnetic Resonance Spectrum (CDCl$_3$) δ ppm: 3.66 (3H, singlet); 5.67 (2H, multiplet).

EXAMPLE 35

Methyl 5-oxo-15-phenyl-16,17,18,19,20-pentanorprostaglandin E$_1$

Following a similar procedure to that described in Examples 1(i)–(n), but reacting 1.0 g of 1α-acetoxy2α(3-acetoxy-6-methoxycarbonylhexyl)-3β-formyl4α(tetrahydropyran-2-yloxy)cyclopentane [prepared as described in Example 1(h)]and 1.1 g of dimethyl 2-oxo-2-phenethylphosphonate, 79 mg of the title compound were obtained as an oily substance.

Infrared Absorption Spectrum (liquid film) $\nu_{max}$ cm$^{-1}$: 3400, 1738, 1718 (shoulder), 972.

Nuclear Magnetic Resonance Spectrum (CDCl$_3$), δ ppm: 3.67 (3H, singlet); 5.77 (2H, multiplet).

EXAMPLE 36

5-Oxoprostaglandin E$_1$ 4 ml of a phosphate buffer (of pH 8) were added to a solution of 30 mg of 5-oxoprostaglandin E$_1$ methyl ester prepared as described in Example 3) in 0.4 ml of acetone, and then 0.27 ml of an esterase (No. E-3128. available from Sigma Chemical Co. U.S.A.) were added to the resulting mixture, and the mixture was stirred at room temperature for 2hours. At the end of this time, the reaction mixture was mixed with a saturated aqueous solution of sodium chloride, acidified by adding dilute aqueous hydrochloric acid, whilst cooling, and then extracted with ethyl acetate. The extract was washed with a saturated aqueous solution of sodium chloride and dried over anhydrous sodium sulphate; the solvent was then removed by distillation under reduced pressure. The resulting residue was purified by silica gel column chromatography, to give 27 mg of the title compound as an oily substance :rom those fractions eluted with ethyl acetate.

Infrared Absorption Spectrum (liquid film) u cm$^{-1}$: 3380, 1738, 1700 (shoulder), 972.

Nuclear Magnetic Resonance Spectrum (CDCl$_3$), δ ppm:
0 89 (3H, broad triplet);
5 62 (2H, multiplet).

EXAMPLE 37

N-[5,9-Dioxo-11,15-dihydroxy-16-phenoxy-17,18,19,20-tetranorprost-13(E)-enoyl] glycine methyl ester Following a similar procedure to that described in Example 36, 720 mg of 5-oxo-16-phenoxy-17,18,19,20tetranorprostaglandin E$_1$ 11,15-di(tetrahydropyran-2-yl)ether methyl ester [prepared as described in Example 1(m)]were hydrolysed with the esterase, to give 580 mg of 5.9-dioxo 11.15 dihydroxy-16-phenoxy17,18,19,20-tetranorprost 13(E)-enoic acid 11,15-di(-tetrahydropyran-2-yl) ether.

101 mg of triethylamine, followed by 122 mg of isopropyl chloroformate were added to a solution of the whole of the 5,9-dioxo-11,15-dihydroxy-16-phenoxy17, 18, 19, 20-tetranorprost-b 13(E) enoic acid 11,15di(-tetrahydropyran-2-yl) ether (prepared as described above) in 7 ml of acetone, whilst ice-cooling. The resulting mixture was stirred for 15 minutes at the temperature of ice-cooling, and then a further 110 mg of triethylamine were added, followed by 115 mg of glycine methyl ester. The resulting mixture was stirred at room temperature for 1 hour. At the end of this time, the reaction mixture was diluted with ethyl acetate, washed with water and then dried over anhydrous sodium sulfate. The solvent was then removed by distillation under reduced pressure, and the residue was purified by silica gel column chromatography, to give 89 mg of the amide of the title compound as an oily substance, from those fractions eluted with hexane containing ethyl acetate in proportions ranging from 40-100% by volume.

This amide was then treated in the same way as described in Example 1(n). to give 15 mg of the title compound as an oily substance.

Infrared Absorption Spectrum (liquid film) $\nu_{max}$ cm$^{-1}$: 3400, 1740, 1710 (shoulder), 1660, 1598, 972.

Nuclear Magnetic Resonance Spectrum (CDCl$_3$) $\delta$ ppm:
3.79 (3H, singlet);
4.01 (2H, doublet);
5.78 (2H, multiplet);
6.7-7.5 (5H, multiplet).

EXAMPLE 38

5-Oxo-16,16-dimethyl-20-methyleneprostaglandin E$_1$

Following a similar procedure to that described in Example 36, but treating 13 mg of 5-oxo-16,16-dimethyl20-methyleneprostaglandin E$_1$ methyl ester (prepared as described in Example 8) with the esterase, 8 mg of the title compound were obtained, as an oily substance.

Infrared Absorption Spectrum (liquid film)$\nu_{max}$ cm$^{-1}$: 1730, 1710 (shoulder), 1640, 972.

Nuclear Magnetic Resonance Spectrum (CDCl$_3$) $\delta$ ppm: 0.89 (3H×2, 2peaks); 4.4-6.1 (8H, multiplet).

EXAMPLE 39

5-Oxo-17(S)-methyl-20-isopropylprostaglandin E$_1$ methyl ester

Following a similar procedure to that described in Examples 2(a)(f), but reacting 1.00 g of 1$\alpha$-acetoxy-2$\alpha$-(3-acetoxy-6-methoxycarbonylhexyl)3$\alpha$-formyl 4$\alpha$-(tetrahydropyran-2-yloxy)cyclopentane and 1.00 g of dimethyl 2-oxo-4,8-dimethylnonyl phosphonate, 161 mg of the title compound were obtained, as an oily substance.

Infrared Absorption Spectrum (liquid film)$\nu_{max}$ cm$^{-1}$: 3400, 1738, 1710 (shoulder), 970.

Nuclear Magnetic Resonance Spectrum (CDCl$_3$3), $\delta$ ppm:
0.7-1.0 (9H, multiplet);
3.68 (3H, singlet);
5.60 (2H, multiplet).

PHARMACOLOGICAL ACTIVITY

The compounds of the present invention have shown excellent anti-ulcer activity, accompanied by a blood platelet aggregation inhibitary activity which is so low as to be insignificant. These activities were determined as described below.

Effects on ethanol-induced qastric ulcers

The test animals used were male rats of the Sprague-Dawley strain each having a body weiqht of about 180-200 g, prior to use in this experiment they were starved for about 42 hours. At the end of this time, each animal was orally administered one of the test compounds shown in the following Table 3. in which the compounds are identified by the number of the foregoing Example in which they were prepared. One hour after administration, gastric mucosal lesions were induced by the oral administration of 1 ml of absolute ethanol. One hour after this administration, the animals were sacrificed with dry ice, and their stomachs were removed and fixed with formalin. The area (mm$^2$) of the mucosal lesions induced on the gastric mucosa by the ethanol was measured by a video image processor and the inhibition of gastric mucosal lesions by each test compound was calculated in terms of the ID$_{50}$, by comparison with the results achieved from control animals which had been treated as described above, except that no anti ulcer compound was administered and from the results achieved from the test compounds at various levels of administration. The results in terms of $\mu$g/kg body weight are shown in the following Table 3.

As a control, there was used the following prior art 6-oxo compound (ORNOPROSTIL):

(C)

Inhibition of blood platelet aggregation in vitro

One part by volume of blood from a Japanese white rabbit was mixed immediately after removal with one tenth of its volume of a 3.8% w/v aqueous solution of sodium citrate. The mixture was then centrifuged at 95×G for 15 minutes at room temperature to obtain a platelet-rich plasma (PRP) as the upper layer. The remaining blood sample was then centrifuged for a further 15 minutes at 1000×G to obtain a platelet poor plasma (PPP). By mixing appropriate amounts of the PRP and the PPP, the final platelet count of the mixture was adjusted to 6×10$^5$ per $\mu$, platelet aggregation was determined by Born's method [G. V. R. Born: J. Physiol. 62, 67-68 (1962)] by increases in transparency of the test liquid using a platelet aggregometer 25 $\mu$l of a solution of the test compound were added to 250 $\mu$of the mixture of PRP and PPP and then two minutes after mixing the solutions 25 $\mu$l of a liquid containing adenosine diphosphate at a concentration of 5$\mu$M were added.

The inhibition of platelet aggregation was assessed by comparing the increase in the amount of light transmitted through the test sample treated platelet-rich plasma with a control platelet-rich plasma which had been treated in the same way, except that the test compound was replaced by physiological saline. The IC$_{50}$ values were calculated from the dose-response curve and are shown in the following Table 3.

TABLE 3

| Test Cpd. | Anti-ulcer activity (ID$_{50}$, p.o. $\mu$g/kg) | Blood platelet aggregation inhibition (IC$_{50}$, ng/ml) |
|---|---|---|
| Cpd. of Ex. 1 | 2.94 | >10,000 |
| Cpd. of Ex. 11 | 0.49 | >10,000 |
| Cpd. of Ex. 30 | 3.70 | >10,000 |
| Cpd. of Ex. 31 | 4.91 | >10,000 |

TABLE 3-continued

| Test Cpd. | Anti-ulcer activity ($ID_{50}$, p.o. µg/kg) | Blood platelet aggregation inhibition ($IC_{50}$, ng/ml) |
|---|---|---|
| Control | 0.20 | 1.9 |

As is apparent from the results shown in the above Table, the compounds of the invention have excellent anti-ulcer activity and are characterised by an extremely weak inhibitory activity against blood platelet aggregation, this activity being undesirable for an anti-ulcer agent, as compared with the prior art compounds.

We claim:

1. A compound of formula (I):

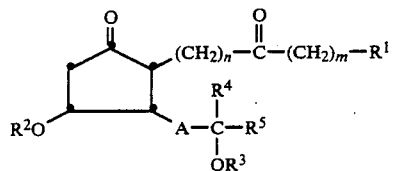

wherein:
- $R^1$ represents a carboxy group, a tetrazolyl group, a carbamoyl group, a substituted carbamoyl group having one or two substituents selected from the group consisting of substituents (a), a hydroxymethylcarbonyl group, a protected hydroxymethylcarbonyl group, a hydroxymethyl group or a protected hydroxymethyl group;
- $R^2$ and $R^3$ are independently selected from the group consisting of hydrogen atoms and hydroxy-protecting groups;
- $R^4$ represents a hydrogen atom or a $C_1$-$C_4$ alkyl group;
- $R^5$ represents a $C_1$-$C_{12}$ alkyl group, a substituted $C_1$-$C_{12}$ alkyl group having at least one substituent selected from the group consisting of substituents ($b^1$), a $C_2$-$C_{12}$ alkenyl group a substituted $C_2$-$C_{12}$ alkenyl group having at least one substituent selected from the group consisting of substituents ($b^1$), a $C_2$-$C_{12}$ alkenyl group, a substituted $C_2$-$C_{12}$ alkynyl group having at least one substituent selected from the group consisting of substituents ($b^1$) or a group of formula B-$R^6$, in which:
- B represents a single bond a $C_1$-$C_6$ alkylene group, —$CH_2$—O—, —$CH(CH_3)$—O—, —$CH_2$—S—, —$CH_2$—O—$CH_2$—, or a $C_2$-$C_6$ alkylene group in which at least one of the carbon-carbon single bonds is replaced by a carbon-carbon double bond;
- $R^6$ represents a $C_3$-$C_{10}$ cycloalkyl group, a substituted $C_3$-$C_{10}$ cycloalkyl group having at least one substituent selected from the group consisting of $C_1$-$C_6$ alkyl groups, an aryl group or a heterocyclic group;
- A represents a group of formula —$CH_2CH_2$—, —CH=CH—, —C≡C—, —O—$CH_2$— or —S—CH—;
- m is 2 or 3; and
- n is an integer from 2 to [5] 3;

substituents (a)
$C_1$—$C_4$ alkyl, acetyl, trifluoroacetyl, benzoyl, methanesulfonyl, ethanesulfonyl, benzenesulfonyl, p-toluenesulfonyl, phenyl and tolyl groups;

substituents ($b^1$)
halogen atoms and $C_1$-$C_4$ alkoxy groups;

said protected groups of a protected hydroxymethylcarbonyl, protected hydroxymethyl and protected hydroxy groups are selected from the group consisting of benzyl, p-nitrobenzyl, p-methoxybenzyl, 2-tetrahydropyranyl, 2-tetrahydrofuranyl, 4-methoxytetrahydropyran-4-yl, 2-tetrahydrothiopyranyl, methoxymethyl, methylthiomethyl, ethoxymethyl, benzyloxymethyl, 1-methoxyethyl, 1-ethoxyethyl, tri-($C_1$-$C_4$ alkyl)silyl, diaryl($C_1$-$C_4$ alkyl)sylyl and trityl groups;

said aryl groups and the aromatic parts of said aromatic carboxylic acyl and arylsulfonyl groups being $C_6$-$C_{12}$ carbocyclic aryl groups which are unsubstituted or have at least one substituents selected from the group consisting of hydroxy groups, $C_1$-$C_4$ alkyl groups, $C_1$-$C_4$ alkoxy groups, $C_1$-$C_4$ alkylthio groups, halogen atoms, aryl groups (provided that the aryl substituents is not itself substituted by an aryl group), trifluoromethyl groups, amino groups and $C_2$-$C_5$ aliphatic carboxylic acylamino groups;

said heterocylic groups are groups selected from the group consisting of tetrahydrofuryl, tetrahydropyranyl, tetrahydrothienyl, pyrrolidinyl, piperidyl, morpholinyl, furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl groups;

and pharmaceutically acceptable salts and esters thereof.

2. The compound as claimed in claim 1, wherein said esters are selected from the group consisting of:
$C_1$-$C_{10}$ alkyl esters; $C_3$-$C_7$ cycloalkyl esters; $C_1$-$C_3$ alkyl-phenyl esters; $C_1$-$C_3$ alkyl-phenyl esters having halogen, $C_1$-$C_4$ alkyl, $C_1$-$C_4$ alkoxy or trifluoromethyl substituent(s) on the phenyl ring; phenyl esters; phenyl esters having $C_1$-$C_4$ alkyl, benzoyl amino or $C_2$-$C_5$ aliphatic acyl amino substituent(s) on the phenyl ring; naphthyl esters; naphthyl esters having $C_1$-$C_4$ alkyl, benzoyl amino or $C_2$-$C_5$ aliphatic acyl amino substituent(s) on the naphthyl ring; benzhydryl ester; phenacyl ester and geranyl esters.

3. The compound as claimed in claim 1, wherein said esters are $C_1$—$C_{10}$ alkyl esters.

4. The compound as claimed in claim 1 wherein:
- $R^1$ represents a carboxy group, a carbamoyl group, a carbamoyl group having one or two substituents selected from the group consisting of $C_1$-$C_4$ alkyl groups. phenyl groups and methanesulfonyl groups, a hydroxymethylcarbonyl group or a hydroxymethyl group;
- $R^1$ and $R^3$ are the same and each represents a hydrogen atom;
- $R^5$ represents a $C_3$-$C_{10}$ alkyl group which is unsubstituted or has at least one substituent selected from the group consisting of fluorine atoms, chlorine atoms and $C_1$-$C_4$ alkoxy groups, a $C_5$-$C_{10}$ alkenyl group, a $C_5$-$C_{10}$ alkynyl group or a group of formula —B—$R^6$, in which:
- B represents a single bond, a $C_1$-$C_4$ alkylene group, —$CH_2$—O—, —$CH(CH_3)$—O—, —$CH_2$—S—or—$CH_2$—O—$CH_2$—; and
- $R^6$ represents a $C_3$-$C_{10}$ cycloalkyl group, a phenyl group which is unsubstituted or has at least one substituent selected from the group consisting of $C_1$-$C_4$ alkyl groups, $C_1$-$C_4$ alkoxy groups, $C_2$-$C_5$ aliphatic acylamino groups, trifluoromethyl groups and halogen atoms, or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl;

A represents a trans-vinylene group; and n is 2 or 3.

5. The compound as claimed in claim 1, wherein:

$R^1$ represents a carboxy group, a carbamoyl group, a carbamoyl group having one or two substituents selected from the group consisting of $C_1$-$C_4$ alkyl groups, phenyl groups and methanesulfonyl groups, a hydroxymethylcarbonyl group or a hydroxymethyl group;

$R^2$ and $R^3$ are the same and each represents a hydrogen atom;

$R^5$ represents a $C_5$-$C_{10}$ alkyl group, a $C_5$-$C_{10}$ alkenyl group, a $C_5$-$C_{10}$ alkynyl group or a group of formula —B—$R^6$, in which:

B represents a single bond, a $C_1$-$C_4$ alkylene group, —CH$_2$—O—, —CH(CH$_3$)—O—, —CH$_2$—S—or—CH$_2$—O—CH$_2$—; and $R^6$ represents a $C_3$-$C_6$ cycloalkyl group, a phenyl group which is unsubstituted or has at least one substituents selected from the group consisting of $C_1$-$C_4$ alkyl groups, $C_2$-$C_5$ aliphatic acylamino groups, trifluoromethyl groups and halogen atoms, or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl.

A represents a trans-vinylene group;

m is 3; and n is 2.

6. The compound as claimed in claim 1, wherein $R^1$ represents a carboxy group, a carbamoyl group, a carbamoyl group having one or two substituents selected from the group consisting of $C_1$-$C_4$ alkyl groups, phenyl groups and methanesulfonyl groups, a hydroxymethylcarbonyl group or a hydroxymethyl group.

7. The compound as claimed in claim 1, wherein $R^2$ and $R^3$ are the same and each represents a hydrogen atom.

8. The compound as claimed in claim 1, wherein $R^5$ represents a $C_3$-$C_{10}$ alkyl group which is unsubstituted or has at least one substituent selected from the group consisting of fluorine atoms, chlorine atoms and $C_1$-$C_4$ alkoxy groups, a $C_5$-$C_{10}$ alkenyl group, a $C_5$-$C_{10}$ alkynyl group or a group of formula —B—$R^6$, in which:

B represents a single bond, a $C_1$-$C_4$ alkylene group, —CH$_2$—O—, —CH(CH$_3$)—O—, —CH$_2$—S—or —CH$_2$—O—CH$_2$—; and $R^6$ represents a $C_3$-$C_{10}$ cycloalkyl group, a phenyl group which is unsubstituted or has at least one substituent selected from the group consisting of $C_1$-$C_4$ alkyl groups, $C_1$-$C_4$ alkoxy groups, $C_2$-$C_5$ aliphatic acylamino groups, trifluoromethyl groups and halogen atoms, or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl.

9. The compound as claimed in claim 1 wherein A represents a trans-vinylene group.

10. The compound as claimed in claim 1 wherein n is 2 or 3.

11. The compound as claimed in claim 1, wherein m is 3 and n is 2.

12. The compound as claimed in claim 1, wherein m is 2 and n is 3.

13. The compound as claimed in claim 4, wherein said esters are selected from the group consisting of:

$C_1$-$C_{10}$ alkyl esters; $C_3$-$C_7$ cycloalkyl esters; $C_1$-$C_3$ alkyl-phenyl esters; $C_1$-$C_3$ alkyl-phenyl esters having halogen, $C_1$-$C_4$ alkyl, $C_1$-$C_4$ alkoxy or trifluoromethyl substituent(s) on the phenyl ring; phenyl esters; phenyl esters having $C_1$-$C_4$ alkyl, benzoyl amino or $C_2$-$C_5$ aliphatic acyl amino substituents(s) on the phenyl ring; naphthyl esters; naphthyl esters having $C_1$-$C_4$ alkyl, benzoyl amino or $C_2$-$C_5$ aliphatic acyl amino substituent(s) on the naphthyl ring; benzhydryl ester; phenacyl ester and geranyl esters.

14. The compound as claimed in claim 1 wherein:

$R^1$ represents a carboxy group, a carbamoyl group, a carbamoyl group having one or two substituents selected from the group consisting of $C_1$-$C_4$ alkyl groups, phenyl groups and methanesulfonyl groups, a hydroxymethylcarbonyl group or a hydroxymethyl group;

$R^2$ and $R^3$ are the same and each represents a hydrogen atom;

$R^5$ represents a $C_3$-$C_{10}$ alkyl group which is unsubstituted or has at least one substituent selected from the group consisting of fluorine atoms, chlorine atoms and $C_1$-$C_4$ alkoxy groups, a $C_5$-$C_{10}$ alkenyl group, a $C_5$-$C_{10}$ alkynyl group or a group of formula —B—$R^6$, in which:

B represents a single bond, a $C_1$-$C_4$ alkylene group, —CH$_2$—O—, —CH(CH$_3$)—O—, —CH$_2$—S— or —CH$_2$—O—CH$_2$—; and $R^6$ represents a $C_3$-$C_{10}$ cycloalkyl group, a phenyl group which is unsubstituted or has at least one substituent selected from the group consisting of $C_1$-$C_4$ alkyl groups, $C_1$-$C_4$ alkoxy groups, $C_2$-$C_5$ aliphatic acylamino groups, trifluoromethyl groups and halogen atoms, or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl;

A represents a trans-vinylene group;

m is 3 and n is 2.

15. The compound as claimed in claim 1, wherein $R^1$ represents a carboxy group, a carbamoyl group, a carbamoyl group or a carbamoyl group having one substituent selected from the group consisting of $C_1$-$C_4$ alkyl groups, phenyl groups and methanesulfonyl groups.

16. The compound as claimed in claim 1 wherein $R^5$ represents a $C_5$-$C_{10}$ alkyl group, a $C_5$-$C_{10}$ alkenyl group, a $C_5$-$C_{10}$ alkynyl group or a group of formula —B—$R^6$, in which:

B represents a single bond, a $C_1$-$C_4$ alkylene group, —CH$_2$—O—, —CH(CH$_3$)—O—, —CH$_2$—S—or —CH$_2$—O—CH$_2$—; and $R^6$ represents a $C_3$-$C_6$ cycloalkyl group, a phenyl group which is unsubstituted or has at least one substituents selected from the group consisting of $C_1$-$C_4$ alkyl groups, $C_1$-$C_4$ alkoxy groups, $C_2$-$C_5$ aliphatic acylamino groups, trifluoromethyl groups and halogen atoms, or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl.

17. The compound as claimed in claim 1, wherein:
$R^1$ represents a carboxy group, a carbamoyl group or a carbamoyl group having one substituent selected from the group consisting of $C_1$–$C_4$ alkyl groups, phenyl groups and methanesulfonyl groups;
$R^2$ and $R^3$ are the same and each represents a hydrogen atom;
$R^5$ represents a $C_5$–$C_{10}$ alkyl group, a $C_5$–$C_{10}$ alkenyl group, a $C_5$–$C_{10}$ alkynyl group or a group of formula —B—$R^6$, in which:
B represents a single bond, a $C_1$–$C_4$ alkylene group, —$CH_2$—O—, —$CH(CH_3)$—O—, —$CH_2$—S— or —$CH_2$—O—$CH_2$—; and
$R^6$ represents a $C_3$—$C_6$ cycloalkyl group, a phenyl group which is unsubstituted or has at least one substituent selected from the group consisting of $C_1$–$C_4$ alkyl groups, $C_2$–$C_5$ aliphatic acylamino groups, trifluoromethyl groups and halogen atoms or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl.
A represents a trans-vinylene group; and
m is 3 and n is 2 or m is 2 and n is 3.

18. The compound as claimed in claim 5, wherein said esters are $C_1$–$C_{10}$ alkyl esters.

19. The compound as claimed in claim 1 wherein $R^1$ represents a carboxy group.

20. A compound as claimed in claim 1, wherein $R^5$ represents a $C_5$–$C_{10}$ alkyl group, a $C_5$–$C_{10}$ alkenyl group or a group of formula —B—$R^6$, in which:
B represents a single bond, a methylene group, an ethylene group or a group of formula —$CH_2$—O— or —$CH(CH_3)$—O—, and
$R^6$ represents a $C_3$–$C_6$ cycloalkyl group, a phenyl group, an indolyl group or a substituted phenyl group having at least one substituent selected from the group consisting of $C_1$–$C_4$ alkyl groups, $C_1$–$C_4$ alkoxy groups, halogen atoms and $C_2$–$C_5$ aliphatic carboxylic acylamino groups.

21. A compound &s claimed in claim 1, wherein
$R^1$ represents a carboxy group.
R2and $R^3$ are the same and each represents a hydrogen atom;
$R^5$ represents a $C_5$–$C_{10}$ alkyl group, a $C_5$–$C_{10}$ alkenyl group or a group of formula —B—$R^6$, in which:
B represents a single bond, a methylene group, an ethylene group or a group of formula —$CH_2$—O— or —$CH(CH_3)$—O—, and -CH(CH )-0-, and 2 $R^6$ represents a $C_3$–$C_6$ cycloalkyl group, a phenyl group, an indolyl group or a substituted phenyl group having at least one substituent selected from the group consisting of $C_1$–$C_4$ alkyl groups, $C_1$–$C_4$ alkoxy groups, halogen atoms and $C_2$—$C_5$ aliphatic carboxylic acylamino groups;
A represents a trans-vinylene group; and
m is 3 and n is 2or m is 2and n is 3.

22. The compound as claimed in claim 1, wherein:
$R^1$ represents a carboxy group;
R2and $R^3$ are the same and each represents a hydrogen atom;
$R^5$ represents a $C_5$–$C_{10}$ alkyl group, a $C_5$–$C_{10}$ alkenyl group or a group of formula —B—$R^6$, in which:
B represents a single bond, a methylene group, an ethylene group or a group of formula —$CH_2$—O— or —$CH(CH_3)$—O—, and $R^6$ represents a $C_3$–$C_6$ cycloalkyl group, a phenyl group, an indolyl group or a substituted phenyl group having at least one substituent selected from the group consisting of C - $C_4$ alkyl groups, C - C alkoxy groups, halogen atoms and C - C aliphatic carboxylic acylamino groups;
A represents a trans-vinylene group;
m is 3; and
n is 2.

23. The compound as claimed in claim 1, wherein $R^4$ represents a hydrogen atom.

24. The compound as claimed in claim 1, selected from the group consisting of 5-oxo-16-phenoxy-17,18,19,20tetranorprostaglandin $E_1$ and pharmaceutically acceptable salts and esters thereof.

25. A compound as claimed in claim 1 selected from the group consisting of 5-oxo-16,16-dimethylprostaglandin $E_1$ and its methyl ester and pharmaceutically acceptable salts thereof.

26. The compound as claimed in claim 1, selected from the group consisting of 5-oxo-17-methylprostaglandin $E_1$ and its methyl ester and pharmaceutically acceptable salts thereof.

27. The compound as claimed in claim 1 selected from the group consisting of 5-oxo-16-phenoxy-17,18,19,20tetranorprostaglandin $E_1$ and its methyl ester and pharmaceutically acceptable salts thereof.

28. A compound as claimed in claim 1, selected from the group consisting of 5-oxo-16-(p-chlorophenoxy)17,18,19,20-tetranorprostaglandin $E_1$ and its methyl ester and pharmaceutically acceptable salts thereof.

29. A compound as claimed in claim 1 selected from the group consisting of 5-oxo-16-(m-chlorophenoxy)17,18,19,20-tetranorprostaglandin $E_1$ and its methyl ester and pharmaceutically acceptable salts thereof.

30. The compound as claimed in claim 1, selected from the group consisting of 5-oxo-16-(p-fluorophenoxy)17,18,19,20-tetranorprostaglandin $E_1$ and its methyl ester and pharmaceutically acceptable salts thereof.

31. The compound as claimed in claim 1 selected from the group consisting of 5-oxo-16-(m-fluorophenoxy)17,18,19,20-tetranorprostaglandin $E_1$ and its methyl ester and pharmaceutically acceptable salts thereof.

32. The compound as claimed in claim 1, selected from the group consisting of 5-oxo-16-methyl-16-phenoxy17,18,19,20-tetranorprostaglandin $E_1$ and its methyl ester and pharmaceutically acceptable salts thereof.

33. The compound as claimed in claim 1 selected from the group consisting of 4-oxo-16,16-dimethylprostaglandin $E_1$ and its methyl ester and pharmaceutically acceptable salts thereof.

34. The compound as claimed in claim 1, selected from the group consisting of 4,9-dioxo-11α15α-dihydroxy16-phenoxy-17,18,19,20-tetranorprost-13(E)-enoic acid and its methyl ester and pharmaceutically acceptable salts thereof.

35. The compound as claimed in claim 1, selected from the group consisting of 4,9-dioxo-11α,15α-dihydroxy 16-p-chlorophenoxy-17,18,19,20-tetranorprost-13(E)enoic acid and its methyl ester and pharmaceutically acceptable salts thereof.

36. A pharmaceutical composition comprising an anti-ulcer effective amount of at least one anti-ulcer compound in admixture with a pharmaceutically acceptable carrier or diluent, wherein said anti-ulcer compound is selected from the group consisting of compounds of formula (I):

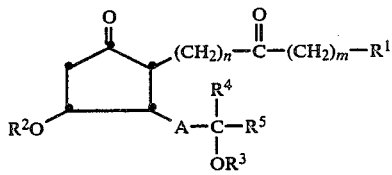

in which:
R$^1$ represents a carboxy group, a tetrazolyl group, a carbamoyl group, a substituted carbamoyl group having one or two substituents selected from the group consisting of substituents (a), a hydroxymethylcarbonyl group or a hydroxymethyl group;
R$^2$ and R$^3$ are hydrogen atoms;
R$^4$ represents a hydrogen atom or a C$_1$-C$_4$ alkyl group;
R$^5$ represents a C$_1$-C$_{12}$ alkyl group, a substituted C$_1$-C$_{12}$ alkyl group having at least one substituent selected from the group consisting of substituents (b), a C$_2$-C$_{12}$ aliphatic hydrocarbon group having at least one ethylenic double bond, a substituted C$_2$-C$_{12}$ aliphatic hydrocarbon group having at least one ethylenic double bond and having at least one substituent selected from the group consisting of substituents (b), a C$_2$-C$_{12}$ alkynyl group, a substituted C$_2$-C$_{12}$ alkynyl group having at least one substituent selected from the group consisting of substituents (b) or a group of formula —B—R$^6$, in which:
B represents a single bond, a C$_1$-C$_6$ alkylene group, —CH$_2$—O—, —CH(CH$_3$)—O—, —CH$_2$—S—, —CH$_2$—O—Ch$_2$—, or a C$_2$-C$_6$ alkylene group in which at least one of the carbon-carbon single bonds is replaced by a carbon-carbon double bond; and
R$^6$ represents a C$_3$-C$_{10}$ cycloalkyl group, a substituted C$_3$-C$_{10}$ cycloalkyl group having at least one substituent selected from the group consisting of C$_1$-C$_6$ alkyl groups, an aryl group, or a heterocyclic group;
A represents a group of formula —CH$_2$CH$_2$—, —CH=CH—, —C≡C—, —O—CH$_2$—or —S—CH$_2$—;
m is 2 or 3; and
n is an integer from 2 to 3;
substituents (a)
C$_1$-C$_4$ alkyl, acetyl, trifluoroacetyl, benzoyl, methanesulfonyl, ethanesulfonyl, benzenesulfonyl, p-toluenesulfonyl, phenyl and tolyl groups;
substituents (b)
halogen atoms, C$_1$-C$_4$ alkoxy groups, aliphatic carboxylic acyl groups, aromatic carboxylic acyl groups and groups of formula —OR$^7$ where R$^7$ represents a hydrogen atom, a C$_2$-C$_5$ aliphatic carboxylic acyl group, an aromatic carboxylic acyl group, an aralkyl group in which the alkyl part is C$_1$-C$_4$, a heterocyclic group, an alkoxyalkyl group in which the alkoxy and alkyl parts are both C$_1$-C$_4$, an alkylthioalkyl group in which each alkyl part is C$_1$-C$_4$, an aralkyloxymethyl group in which the alkyl part is C$_1$-C$_4$, a tri-(C$_1$-C$_4$ alkyl) silyl group or a diaryl (C$_1$-C$_4$ alkyl) silyl group;
said aryl groups and the aromatic parts of said aromatic carboxylic acyl, arylsulfonyl, aralkyl and aralkyloxymethyl groups being C$_6$-C$_{12}$ carbocyclic aryl groups which are unsubstituted or have at least one substituent selected from the group consisting of substituents (c);
substituents (c):
hydroxy groups, C$_1$-C$_6$ alkyl groups, C$_1$-C$_4$ alkoxy groups, C$_1$-C$_4$ alkylthio groups, C$_2$-C$_7$ aliphatic carboxylic acyl groups, C$_2$-C$_7$ aliphatic carboxylic acyloxy groups, aryl groups provided that the aryl substituents is not itself substituted by an aryl group, aromatic carboxylic acyl groups, aromatic carboxylic acyloxy groups, C$_2$-C$_7$ aliphatic carboxylic acylamino groups, aromatic carboxylic acylamino groups, heterocyclic-carbonyl groups, arylalkenoyl groups in which the alkenoyl part is C$_3$-C$_7$, trifluoromethyl groups, halogen atoms, nitro groups, cyano groups, amino groups, C$_1$-C$_4$ alkylamino groups, dialkylamino groups in which each alkyl part is C$_1$-C$_4$, carbamoyl groups, alkylcarbamoyl groups in which the alkyl part is C$_1$-C$_4$, dialkylcarbamoyl groups in which each alkyl part is C$_1$-C$_4$, alkoxycarbonyloxy groups in which the alkoxy part is C$_1$-C$_4$, heterocyclic groups, carboxy groups, said aryl groups and the aromatic parts of said aromatic acyl, acyloxy and acylamino groups being C$_6$-C$_{10}$ carbocyclic aryl groups which are unsubstituted or have at least one substituent selected from the group consisting of C$_1$-C$_4$ alkyl groups, C$_1$-C$_4$ alkoxy groups, hydroxy groups and halogen atoms;
said heterocyclic groups and heterocyclic part of heterocyclic carbonyl groups are groups selected from the group consisting of tetrahydrofuranyl, tetrahydropyranyl, tetrahydrothienyl, pyrrolidinyl, piperidyl, morpholinyl, furyl, thienyl, pyrrolyl, imidazolyl, oxazolyl, thiazolyl, isoxazolyl, pyridyl, indolyl, 3H-indolyl, isoindolyl, purinyl, quinolyl, and isoquinolyl groups;
and pharmaceutically acceptable salts and esters thereof.

37. The composition as claimed in claim 36, wherein:
R$^1$ represents a carboxy group, a carbamoyl group, a carbamoyl group having one or two substituents selected from the group consisting of C$_1$-C$_4$ alkyl groups, substituted C$_1$-C$_4$ alkyl groups having at least one substituent selected from the group consisting of substituents (a$^1$), phenyl groups and methanesulfonyl groups, a hydroxymethylcarbonyl group or a hydroxymethyl group;
R$^5$ represents a C$_3$-C$_{10}$ alkyl group which is unsubstituted or has at least one substituent selected from the group consisting of fluorine atoms, chlorine atoms and C$_1$-C$_4$ alkoxy groups, a C$_5$-C$_{10}$ alkenyl group, a C$_5$-C$_{10}$ alkynyl group or a group of formula —B—R$^6$, in which:
B represents a single bond, a C$_1$-C$_4$ alkylene group, —CH$_2$—O—, —CH(CH$_3$)—O—, —CH$_2$—S—or —CH$_2$—O—CH$_2$—; and
R$^6$ represents a C$_3$-C$_{10}$ cycloalkyl group, a phenyl group which is unsubstituted or has at least one substituent selected from the group consisting of C$_1$-C$_4$ alkyl groups, C$_1$-C$_4$ alkoxy groups, C$_2$-C$_5$ aliphatic acylamino groups, trifluoromethyl groups and halogen atoms, or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl;
A represents a trans-vinylene group; and
m is 2 or 3 and n is 2 or 3.

38. The composition as claimed in claim 36, wherein:
$R^1$ represents a carboxy group, a carbamoyl group or a carbamoyl group having one substituent selected from the group consisting of $C_1-C_4$ $C_1-C_4$ alkyl groups, substituted $C_1-C_4$ alkyl groups having at least one substituent selected from the group consisting of substituents ($a^1$), phenyl groups and methanesulfonyl groups;
$R^5$ represents a $C_5-C_{10}$ alkyl group, a $C_5-C_{10}$ alkenyl group, a $C_5-C_{10}$ alkynyl group or a group of formula —B—$R^6$, in which:
  B represents a single bond, a $C_1-C_4$ alkylene group, —$CH_2$—O—, —$CH(CH_3)$—O—, —$CH_2$—S— or —$CH_2$—O—$CH_2$—; and
  $R^6$ represents a $C_3-C_6$ cycloalkyl group, a phenyl group which is unsubstituted or has at least one substituent selected from the group consisting of $C_1-C_4$ alkyl groups, $C_2-C_5$ aliphatic acylamino groups, trifluoromethyl groups and halogen atoms, or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl;
A represents a trans-vinylene group; and
m is 3 and n is 2 or m is 2 and n is 3.

39. The composition as claimed in claim 36, wherein:
$R^1$ represents a carboxy group.
$R^5$ represents a $C_5-C_{10}$ alkyl group, a $C_5-C_{10}$ alkenyl group or a group of formula —B—$R^6$, in which:
  B represents a single bond, a methylene group, an ethylene group or a group of formula —$CH_2$—O— or —$CH(CH_3)$—O—, and
  $R^6$ represents a $C_3-C_6$ cycloalkyl group, a phenyl group, an indolyl group or a substituted phenyl group having at least one substituent selected from the group consisting of $C_1-C_4$ alkyl groups, $C_1-C_4$ alkoxy groups, halogen atoms and $C_2-C_5$ aliphatic carboxylic acylamino groups;
A represents a trans-vinylene group; and m is 3 and n is 2 or m is 2 and n is 3.

40. The composition as claimed in claim 36, wherein:
$R^1$ represents a carboxy group;
$R^5$ represents a $C_5-C_{10}$ alkyl group, a $C_5-C_{10}$ alkenyl group or a group of formula —B—$R^6$, in which:
  B represents a single bond, a methylene group an ethylene group or a group of formula —$CH_2$—O— or —$CH(CH_3)$—O—, and
  $R^6$ represents a $C_3-C_6$ cycloalkyl group, a phenyl group, an indolyl group or a substituted phenyl group having at least one substituent selected from the group consisting of $C_1-C_4$ alkyl groups, $C_1-C_4$ alkoxy groups, halogen atoms and $C_2-C_5$ aliphatic carboxylic acylamino groups;
A represents a trans-vinylene group;
m is 3; and
n is 2.

41. The composition as claimed in claim 36, wherein the anti-ulcer compound is selected from the group consisting of:
5-oxo-16,16-dimethylprostaglandin $E_1$ and its methyl ester;
5-oxo-16,16-dimerhylprostaglandin $E_1$ and its methyl
5-oxo-17-methylprostaglandin $E_1$ and its methyl ester;
5-oxo-16-phenoxy-17,18,19,20-tetranorprostaglandin E and its methyl ester;
5-oxo-16-(p-chlorophenoxy)-17,18,19,20-tetranorprostaglandin1and in $E_1$ and its methyl ester;
5-oxo-16-(m-chlorophenoxy)-17,18,19,20-tetranorprostaglandin $E_1$ and its methyl ester;
5-oxo-16-(p-fluorophenoxy)-17,18,19,20-tetranorprostaglandin $E_1$ and its methyl ester;
5-oxo-16-(m-fluorophenoxy)-17,18,19,20-tetranorprostaglandin $E_1$ and its methyl ester;
5-oxo-16-methyl-16-phenoxy-17,18,19,20-tetranorprostaglandin $E_1$ and irs methyl ester;
5-oxo-16,16-dimethylprostaglandin $E_1$ and its methyl ester;
4,9-dioxo-11α,15α-dihydroxy-16-phenoxy-17,18,19,20-tetranorprost-13(E)-enoic acid and its methyl
4,9-dioxo-11α,15α-dihydroxy-16-p-chlorophenoxy17,18,19,20-tetranorprost-13(E)-enoic acid and its methyl ester;
and pharmaceutically acceptable salts thereof.

42. The composition as claimed in claim 36, wherein said esters are selected from the group consisting of: $C_1-C_{10}$ alkyl esters; $C_3-C_7$ cycloalkyl esters; $C_1-C_3$ alkyl-phenyl esters; C-$C_3$ alkyl-phenyl esters having halogen, $C_1-C_4$ alkyl, $C_1-C_4$ alkoxy or trifluoromethyl substituent(s) on the phenyl ring; phenyl esters; phenyl esters having $C_1-C_4$ alkyl, benzoyl amino or $C_2-C_5$ aliphatic acyl amino substituent(s) on the phenyl ring; naphthyl esters; naphthyl esters having $C_1-C_4$ alkyl, benzoyl amino or $C_2-C_5$ aliphatic acyl amino substituent(s) on the naphthyl ring; benzhydryl ester; phenacyl ester and geranyl esters.

43. A method of treating a mammal to relieve an ulcerative condition by administering thereto an effective amount of at least one anti-ulcer compound, wherein said anti-ulcer compound is selected from the group consisting of compounds of formula (I):

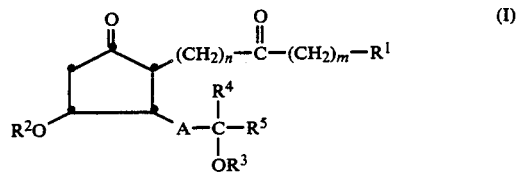

in which:
$R^1$ represents a carboxy group, a tetrazolyl group a carbamoyl group, a substituted carbamoyl group having one or two substituents selected from the group consisting of substituents (a), a hydroxymethylcarbonyl group or a hydroxymethyl group;
$R^2$ and $R^3$ are hydrogen atoms;
$R^4$ represents a hydrogen atom or a $C_1-C_4$ alkyl group;
$R^5$ represents a $C_1-C_{12}$ alkyl group, a substituted $C_1-C_{12}$ alkyl group having at least one substituent selected from the group consisting of substituents (b), a $C_2-C_{12}$ aliphatic hydrocarbon group having at least one ethylenic double bond, a substituted $C_2-C_{12}$ aliphatic hydrocarbon group having at least one ethylenic double bond and having at least one substituent selected from the group consisting of substituents (b), a $C_2-C_{12}$ alkynyl group, a substituent $C_2-C_{12}$ alkynyl group having at least one substituent selected from the group consisting of substituents (b) or a group of formula —B—$R^6$, in which:

B represents a single bond, a $C_1$-$C_6$ alkylene group, —$CH_2$—O—, —$CH(CH_3)$—O—, —$CH_2$—S—, —$CH_2$—O—$CH_2$—, or a $C_2$-$C_6$ alkylene group in which at least one of the carbon-carbon single bonds is replaced by a carbon-carbon double bond; and $R^6$ represents a $C_3$-$C_{10}$ cycloalkyl group, a substituted $C_3$-$C_{10}$ cycloalkyl group having at least one substituent selected from the group consisting of $C_1$-$C_6$ alkyl groups, an aryl group, or a heterocyclic group;

A represents a group of formula —$CH_2CH_2$—, —CH=CH—, —C≡C—, —O—$CH_2$— or —S—$CH_2$—;

m is 2 or 3 and n is an integer from 2 to 3;

substituents (a)

$C_1$-$C_4$ alkyl, acetyl, trifluoroacetyl, benzoyl, methanesulfonyl, ethanesulfonyl, benzenesulfonyl, p-toluenesulfonyl, phenyl and tolyl groups;

substituents (b)

halogen atoms, $C_1$-$C_4$ alkoxy groups, aliphatic carboxylic acyl groups, aromatic carboxylic acyl groups and groups of formula —$OR^7$ where $R^7$ represents a hydrogen atom, a $C_2$-$C_5$ aliphatic carboxylic acyl group, an aromatic carboxylic acyl group, an aralkyl group in which the alkyl part is $C_1$-$C_4$, a heterocyclic group, an alkoxyalkyl group in which the alkoxy and alkyl parts are both $C_1$-$C_4$, an alkylthioalkyl group in which each alkyl part is $C_1$-$C_4$, an aralkyloxymethyl group in which the alkyl part is $C_1$-$C_4$, a tri-($C_1$-$C_4$ alkyl) silyl group or a diaryl ($C_1$-$C_4$ alkyl) silyl group; said aryl groups and the aromatic parts of said aromatic carboxylic acyl, arylsulfonyl, aralkyl and aralkyloxymethyl groups being $C_6$-$C_{12}$ carbocyclic aryl groups which are unsubstituted or have at least one substituent selected from the group consisting of substituents (c):

substituents (c):

hydroxy groups, $C_1$-$C_6$ alkyl groups, $C_1$-$C_4$ alkoxy groups, $C_1$-$C_4$ alkylthio groups, $C_2$-$C_7$ aliphatic carboxylic acyl groups, $C_2$-$C_7$ aliphatic carboxylic acyloxy groups, aryl groups provided that the aryl substituents is not itself substituted by an aryl group, aromatic carboxylic acyl groups, aromatic carboxylic acyloxy groups, $C_2$-$C_7$ aliphatic carboxylic acylamino groups, aromatic carboxylic acylamino groups, heterocyclic-carbonyl groups, arylalkenoyl groups in which the alkenoyl part is $C_3$-$C_7$, trifluoromethyl groups, halogen atoms, nitro groups, cyano groups, amino groups, $C_1$-$C_4$ alkylamino groups, dialkylamino groups in which each alkyl part is $C_1$-$C_4$, carbamoyl groups, alkylcarbamoyl groups in which the alkyl part is $C_1$-$C_4$, dialkylcarbamoyl groups in which each alkyl part is $C_1$-$C_4$, alkoxycarbonyloxy groups in which the alkoxy part is $C_1$-$C_4$, heterocyclic groups, carboxy groups, said aryl groups and the aromatic parts of said aromatic acyl, acyloxy and acylamino groups being $C_6$-$C_{10}$ carbocyclic aryl groups which are unsubstituted or have at least one substituent selected from the group consisting of $C_1$-$C_4$ alkyl groups, $C_1$-$C_4$ alkoxy groups, hydroxy groups and halogen atoms;

said heterocyclic groups and heterocyclic part of heterocyclic carbonyl groups are groups selected from the group consisting of tetrahydrofuranyl, tetrahydropyranyl, tetrahydrothienyl, pyrrolidinyl, piperidyl, morpholinyl, furyl, thienyl, pyrrolyl, imidazolyl, oxazolyl, thiazolyl, isoxazolyl, pyridyl, indolyl, 3H-indolyl, isoindolyl, purinyl, quinolyl, and isoquinolyl groups;

and pharmaceutically acceptable salts and esters thereof.

44. The method as claimed in claim 43, wherein:

$R^1$ represents a carboxy group, a carbamoyl group or a carbamoyl group having one substituent selected from the group consisting of $C_1$-$C_4$ alkyl groups, phenyl groups and methanesulfonyl groups;

$R^5$ represents a $C_5$-$C_{10}$ alkyl group, a $C_5$-$C_{10}$ alkenyl group, a $C_5$-$C_{10}$ alkynyl group or a group of formula —b—$R^6$, in which B represents a single bond, a $C_1$-$C_4$ alkylene group, —$CH_2$—O—, —$CH(CH_3)$—O—, —$CH_2$—S— or —$CH_2$—O—$CH_2$—; and $R^6$ represents a $C_3$-$C_6$ cycloalkyl group, a phenyl group which is unsubstituted or has at least one substituents selected from the group consisting of $C_1$-$C_4$ alkyl groups, $C_2$-$C_5$ aliphatic acylamino groups, trifluoromethyl groups and halogen atoms, or a heterocyclic group selected from the group consisting of furyl, thienyl, pyrrolyl, imidazolyl, oxazolyl, thiazolyl, isoxazolyl, pyridyl, indolyl, 3H-indolyl, isoindolyl, purinyl, quinolyl and isoquinolyl;

A represents a trans-vinylene group; and m is 3 and n is 2 or n is 2 and n is 3.

45. The method as claimed in claim 43, wherein:

$R^1$ represents a carboxy group;

$R^5$ represents a $C_5$-$C_{10}$ alkyl group, a $C_5$-$C_{10}$ alkenyl group or a group of formula —B—$R^6$, in which:

B represents a single bond, a methylene group, an ethylene group or a group of formula —$CH_2$—O— or —$CH(CH_3)$—O—, and $R^6$ represents a $C_3$-$C_6$ cycloalkyl group, a phenyl group, an indolyl group or a substituted phenyl group having at least one substituent selected from the group consisting of $C_1$-$C_4$ alkyl groups, $C_1$-$C_4$ alkoxy groups, halogen atoms and $C_2$-$C_5$ aliphatic carboxylic acylamino groups;

A represents a trans-vinylene group;

m is 3; and n is 2.

46. The method as claimed in claim 43, wherein the anti-ulcer compound is selected from the group consisting of:

5-oxo-16,16-dimethylprostaglandin $E_1$ and its methyl ester;

5-oxo-17-methylprostaglandin $E_1$ and its methyl ester;

5-oxo-16-phenoxy-17,18,19,20-tetranorprostaglandin E and its methyl ester;

5-oxo-16-(p-chlorophenoxy)-17,18,19,20-tetranorprostaglandin $E_1$ and its methyl ester;

5-oxo-16-(m-chlorophenoxy)-17,18,19,20-tetranorprostaglandin $E_1$ and its methyl ester;

5-oxo-16-(p-fluorophenoxy)-17,18,19,20-tetranorprostaglandin $E_1$ and its methyl ester;

5-oxo-16-(m-fluorophenoxy)-17,18,19,20-tetranorprostaglandin $E_1$ and its methyl ester;

5-oxo-16-methyl-16-phenoxy-17,18,19,20-tetranorprostaglandin $E_1$ and its methyl ester;

4-oxo-16,16-dimethylprostaglandin $E_1$ and its methyl ester;

4,9-dioxo-11α-dihydroxy-16-phenoxy-17,18,19,20-tetranorprost-13(E)-enoic acid and its methyl ester;

4,9-dioxo-11α,15α-dihydroxy-16-p-chlorophenoxy-17,18,19,20-tetranorprost-13(E)-enoic acid and its methyl ester;

and pharmaceutically acceptable salts thereof.

47. The method as claimed in claim 43, wherein said esters are selected from the group consisting of:
$C_1$–$C_{10}$ alkyl esters; $C_3$–$C_7$ cycloalkyl esters; $C_1$–$C_3$ alkyl-phenyl esters; $C_1$–$C_3$ alkyl-phenyl esters having halogen, $C_1$–$C_4$ alkyl, $C_1$–$C_4$ alkoxy or trifluoromethyl substituent(s) on the phenyl ring; phenyl esters; phenyl esters having $C_1$–$C_4$ alkyl, benzoyl amino or $C_2$–$C_5$ aliphatic acyl amino substituent(s) on the phenyl ring; naphthyl esters; naphthyl esters having $C_1$–$C_4$ alkyl, benzoyl amino or $C_2$–$C_5$ aliphatic acyl amino substituent(s) on the naphthyl ring; benzhydryl ester; phenacyl ester and geranyl esters.

* * * * *